US012611254B2

(12) United States Patent
Dressler et al.

(10) Patent No.: US 12,611,254 B2
(45) Date of Patent: Apr. 28, 2026

(54) APPARATUS, SYSTEM, AND METHOD FOR DETERMINING A POSITION OF A HIP PROSTHESIS IN A BONE OF A PATIENT

(71) Applicant: DEPUY IRELAND UNLIMITED COMPANY, Ringaskiddy (IE)

(72) Inventors: Matthew R. Dressler, Fort Wayne, IN (US); Chadd Clary, Highlands Ranch, CO (US); Clare K. Fitzpatrick, Boise, ID (US); Casey A. Myers, Denver, CO (US); Paul J. Rullkoetter, Lyons, CO (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 1086 days.

(21) Appl. No.: 17/566,773

(22) Filed: Dec. 31, 2021

(65) Prior Publication Data

US 2022/0202494 A1      Jun. 30, 2022

Related U.S. Application Data

(60) Provisional application No. 63/132,991, filed on Dec. 31, 2020.

(51) Int. Cl.
*A61B 34/10*        (2016.01)
*A61B 34/20*        (2016.01)
(Continued)

(52) U.S. Cl.
CPC .............. *A61B 34/10* (2016.02); *A61B 34/20* (2016.02); *A61F 2/34* (2013.01); *A61F 2/4607* (2013.01);
(Continued)

(58) Field of Classification Search
None
See application file for complete search history.

(56) References Cited

U.S. PATENT DOCUMENTS

| | | | |
|---|---|---|---|
| 5,715,836 A | 2/1998 | Kliegis et al. | |
| 5,995,738 A | 11/1999 | Digioia | |
| | (Continued) | | |

FOREIGN PATENT DOCUMENTS

| | | | |
|---|---|---|---|
| FR | 2932677 B1 | 6/2010 | |
| GB | 2588001 B | 10/2022 | |
| | (Continued) | | |

OTHER PUBLICATIONS

Miki, Hidenobu, et al. "Risk of edge-loading and prosthesis impingement due to posterior pelvic tilting after total hip arthroplasty." Clinical biomechanics 29.6 (2014): 607-613. (Year: 2014).*
(Continued)

*Primary Examiner* — Rehana Perveen
(74) *Attorney, Agent, or Firm* — Barnes & Thornburg LLP

(57)        ABSTRACT

An apparatus, system, and method for determining a position of a hip prosthesis in a bone of a patient includes determining a set of contact points between a femoral head of a femoral prosthesis and a cup liner of an acetabular cup to be implanted into a patient based on a mechanics model. The mechanics model is indicative of mechanical motion of a hip exhibited during performance of a set of ADL or at corresponding functional positions of the patient. In some embodiments, a mathematical model may be generated based on a plurality of sets of contact points determined using the mechanics model and subsequently used to determine a resultant set of contact points.

20 Claims, 40 Drawing Sheets

(51) Int. Cl.

| | |
|---|---|
| *A61F 2/34* | (2006.01) |
| *A61F 2/46* | (2006.01) |
| *G16H 20/40* | (2018.01) |
| *G16H 30/40* | (2018.01) |
| *A61B 90/00* | (2016.01) |
| *A61F 2/36* | (2006.01) |

(52) U.S. Cl.
CPC ............. *G16H 20/40* (2018.01); *G16H 30/40* (2018.01); *A61B 2034/104* (2016.02); *A61B 2034/2065* (2016.02); *A61B 2090/374* (2016.02); *A61B 2090/3762* (2016.02); *A61F 2002/3611* (2013.01); *A61F 2002/4658* (2013.01); *A61F 2002/4668* (2013.01)

(56) References Cited

U.S. PATENT DOCUMENTS

| | | | |
|---|---|---|---|
| 6,205,411 | B1 | 3/2001 | DiGioia, III et al. |
| 6,597,818 | B2 | 7/2003 | Kumar et al. |
| 8,160,345 | B2 | 4/2012 | Pavlovskaia et al. |
| 9,248,002 | B2 | 2/2016 | Mccarthy |
| 9,603,711 | B2 | 3/2017 | Bojarski et al. |
| 9,662,228 | B2 | 5/2017 | Mccarthy |
| 9,687,259 | B2 | 6/2017 | Pavlovskaia et al. |
| 9,913,691 | B2 | 3/2018 | Brooks |
| 10,182,871 | B2 | 1/2019 | Wollowick et al. |
| 10,321,961 | B2 | 6/2019 | Mccarthy et al. |
| 10,433,914 | B2 | 10/2019 | Wollowick et al. |
| 10,500,067 | B2 | 12/2019 | Mccarthy |
| 10,595,943 | B2 | 3/2020 | Barsoum et al. |
| 10,610,305 | B2 | 4/2020 | Wollowick et al. |
| 10,687,856 | B2 | 6/2020 | Park et al. |
| 10,758,198 | B2 | 9/2020 | Wollowick et al. |
| 10,765,384 | B2 | 9/2020 | Wollowick et al. |
| 10,959,782 | B2 | 3/2021 | Wollowick et al. |
| 11,071,592 | B2 | 7/2021 | Mcguan et al. |
| 11,107,586 | B1 | 8/2021 | DeCook et al. |
| 11,147,626 | B2 | 10/2021 | Murphy et al. |
| 11,241,287 | B2 | 2/2022 | Boettner |
| 11,318,025 | B2 | 5/2022 | Schipper et al. |
| 11,337,760 | B2 | 5/2022 | Veilleux et al. |
| 11,337,762 | B2 | 5/2022 | Duxbury et al. |
| 11,439,467 | B1 * | 9/2022 | Park ..................... A61B 34/10 |
| 11,534,127 | B2 | 12/2022 | Wollowick et al. |
| 11,642,174 | B2 | 5/2023 | Wollowick et al. |
| 11,737,893 | B2 | 8/2023 | Schipper et al. |
| 12,198,812 | B2 | 1/2025 | DeCook et al. |
| 2002/0055692 | A1 | 5/2002 | Tanaka et al. |
| 2003/0176860 | A1 | 9/2003 | Shimura |
| 2004/0087852 | A1 | 5/2004 | Chen et al. |
| 2004/0117028 | A1 | 6/2004 | Iversen |
| 2004/0171924 | A1 | 9/2004 | Mire et al. |
| 2005/0054917 | A1 | 3/2005 | Kitson |
| 2005/0203384 | A1 | 9/2005 | Sati et al. |
| 2006/0095047 | A1 | 5/2006 | de la Barrera |
| 2006/0293614 | A1 | 12/2006 | Radinsky et al. |
| 2008/0021299 | A1 | 1/2008 | Meulink |
| 2008/0027312 | A1 | 1/2008 | Dick |
| 2008/0056552 | A1 | 3/2008 | Muller |
| 2008/0075348 | A1 | 3/2008 | Rappaport et al. |
| 2008/0120262 | A1 | 5/2008 | Habets et al. |
| 2008/0146969 | A1 | 6/2008 | Kurtz |
| 2008/0255584 | A1 | 10/2008 | Beverland et al. |
| 2009/0089034 | A1 | 4/2009 | Penney et al. |
| 2009/0316967 | A1 | 12/2009 | Dardenne et al. |
| 2010/0030231 | A1 | 2/2010 | Nitzan et al. |
| 2010/0086181 | A1 | 4/2010 | Zug et al. |
| 2010/0197639 | A1 | 8/2010 | Lang et al. |
| 2011/0093087 | A1 | 4/2011 | Mcmahon et al. |
| 2011/0313424 | A1 | 12/2011 | Bono et al. |
| 2012/0016269 | A1 | 1/2012 | de la Barrera |
| 2012/0116533 | A1 | 5/2012 | Forsell |
| 2012/0157887 | A1 | 6/2012 | Fanson et al. |
| 2012/0194505 | A1 | 8/2012 | Beck |

| | | | |
|---|---|---|---|
| 2012/0209394 | A1 | 8/2012 | Bojarski et al. |
| 2012/0230573 | A1 | 9/2012 | Ito et al. |
| 2013/0046310 | A1 | 2/2013 | Ranawat et al. |
| 2013/0053858 | A1 | 2/2013 | Penenberg |
| 2013/0053859 | A1 | 2/2013 | Penenberg |
| 2013/0072821 | A1 | 3/2013 | Odermatt et al. |
| 2013/0304429 | A1 | 11/2013 | Haimerl |
| 2014/0093154 | A1 | 4/2014 | Penenberg |
| 2014/0378828 | A1 | 12/2014 | Penenberg et al. |
| 2015/0088145 | A1 | 3/2015 | McCarthy |
| 2015/0088146 | A1 | 3/2015 | McCarthy |
| 2015/0117608 | A1 | 4/2015 | Lytle et al. |
| 2015/0150523 | A1 | 6/2015 | Sirpad et al. |
| 2015/0227679 | A1 | 8/2015 | Kamer et al. |
| 2015/0238271 | A1 | 8/2015 | Wollowick et al. |
| 2015/0257846 | A1 | 9/2015 | Kubiak et al. |
| 2015/0272695 | A1 | 10/2015 | Kubiak et al. |
| 2016/0100909 | A1 | 4/2016 | Wollowick et al. |
| 2016/0128654 | A1 | 5/2016 | Wollowick et al. |
| 2016/0203608 | A1 | 7/2016 | Izmirli et al. |
| 2016/0225192 | A1 | 8/2016 | Jones et al. |
| 2017/0042619 | A1 | 2/2017 | Brooks |
| 2017/0128135 | A1 | 5/2017 | McCarthy et al. |
| 2017/0143433 | A1 | 5/2017 | Fanson et al. |
| 2017/0165008 | A1 | 6/2017 | Finley |
| 2017/0202682 | A1 | 7/2017 | McCarthy |
| 2017/0215967 | A1 | 8/2017 | Spath |
| 2017/0224418 | A1 | 8/2017 | Boettner et al. |
| 2017/0258526 | A1 | 9/2017 | Lang |
| 2017/0333137 | A1 | 11/2017 | Roessler |
| 2018/0161101 | A1 | 6/2018 | Barsoum |
| 2018/0199995 | A1 | 7/2018 | Odermatt et al. |
| 2018/0263697 | A1 | 9/2018 | Eskesen et al. |
| 2018/0263699 | A1 | 9/2018 | Murphy et al. |
| 2019/0090962 | A1 | 3/2019 | Boettner |
| 2019/0298452 | A1 | 10/2019 | Veilleux et al. |
| 2019/0350728 | A1 | 11/2019 | van der Walt et al. |
| 2019/0385303 | A1 | 12/2019 | Petersen et al. |
| 2020/0205900 | A1 | 7/2020 | Buckland et al. |
| 2020/0246079 | A1 | 8/2020 | Shevlev et al. |
| 2020/0323648 | A1 | 10/2020 | Samuelson et al. |
| 2020/0323649 | A1 * | 10/2020 | Schipper ............... A61B 34/10 |
| 2020/0405398 | A1 | 12/2020 | Amanatullah |
| 2021/0220054 | A1 | 7/2021 | Parker et al. |
| 2021/0322148 | A1 | 10/2021 | Mitra et al. |
| 2022/0000562 | A1 | 1/2022 | Murphy, M.D. et al. |
| 2022/0008131 | A1 | 1/2022 | Sculco et al. |
| 2022/0039869 | A1 | 2/2022 | Dees, Jr. |
| 2022/0117663 | A1 | 4/2022 | Mcguan et al. |
| 2022/0125515 | A1 | 4/2022 | Mcguan et al. |
| 2022/0148454 | A1 | 5/2022 | Jaramaz et al. |
| 2022/0148739 | A1 | 5/2022 | Farley et al. |
| 2022/0202503 | A1 | 6/2022 | Dressler et al. |
| 2022/0249248 | A1 | 8/2022 | Schipper et al. |
| 2022/0323159 | A1 | 10/2022 | Boettner et al. |
| 2023/0000556 | A1 | 1/2023 | Duxbury et al. |
| 2023/0181257 | A1 | 6/2023 | McGuan et al. |
| 2023/0277331 | A1 | 9/2023 | Beck et al. |
| 2025/0107904 | A1 | 4/2025 | Hunt et al. |
| 2025/0149183 | A1 | 5/2025 | DeCook et al. |

FOREIGN PATENT DOCUMENTS

| | | | |
|---|---|---|---|
| JP | 2004105551 A | 4/2004 | |
| JP | 2005185767 A | 7/2005 | |
| JP | 2007151742 A | 6/2007 | |
| JP | 2009136384 A | 6/2009 | |
| JP | 2012532665 A | 12/2012 | |
| WO | 2007009263 A1 | 1/2007 | |
| WO | 2009108683 A1 | 9/2009 | |
| WO | 2013049534 A1 | 4/2013 | |
| WO | 2013175471 A1 | 11/2013 | |
| WO | 2014025305 A1 | 2/2014 | |
| WO | 2014069553 A1 | 5/2014 | |
| WO | 2016180438 A1 | 11/2016 | |
| WO | 2017106858 A1 | 6/2017 | |
| WO | 2018162322 A1 | 9/2018 | |
| WO | 2019068194 A1 | 4/2019 | |
| WO | WO-2019191722 A1 * | 10/2019 | ............... A61F 2/34 |

(56) References Cited

FOREIGN PATENT DOCUMENTS

| | | | | | |
|---|---|---|---|---|---|
| WO | 2019241516 | A1 | 12/2019 | | |
| WO | 2020/102886 | A1 | 5/2020 | | |
| WO | 2020163314 | A1 | 8/2020 | | |
| WO | 2020163316 | A1 | 8/2020 | | |
| WO | 2020163317 | A1 | 8/2020 | | |
| WO | 2020163318 | A1 | 8/2020 | | |
| WO | 2020163324 | A1 | 8/2020 | | |
| WO | 2020163328 | A1 | 8/2020 | | |
| WO | 2020163330 | A1 | 8/2020 | | |
| WO | 2020163352 | A1 | 8/2020 | | |
| WO | 2020163355 | A1 | 8/2020 | | |
| WO | WO-2020163358 | A1 * | 8/2020 | .............. | G06N 5/01 |
| WO | 2021262539 | A1 | 12/2021 | | |
| WO | 2023044138 | A1 | 3/2023 | | |

OTHER PUBLICATIONS

Luthringer, Tyler A., and Jonathan M. Vigdorchik. "A preoperative workup of a "hip-spine" total hip arthroplasty patient: a simplified approach to a complex problem." The Journal of arthroplasty 34.7 (2019): S57-S70. (Year: 2019).*

Pedersen DR, Brown TD, Maxian TA, Callaghan JJ. Temporal and spatial distributions of directional counterface motion at the acetabular bearing surface in total hip arthroplasty. Iowa Orthop J. 1998;18:43-53. (Year: 1998).*

Henebry A, Gaskill T. The Effect of Pelvic Tilt on Radiographic Markers of Acetabular Coverage. The American Journal of Sports Medicine. 2013;41(11):2599-2603. (Year: 2013).*

Pierrepont, Jim, et al. "The effect of seated pelvic tilt on posterior edge-loading in total hip arthroplasty: a finite element investigation." Proceedings of the Institution of Mechanical Engineers, Part H: Journal of Engineering in Medicine 232.3 (2018): 241-248. (Year: 2018).*

International Search Report for Application No. PCT/EP2021/087907, May 3, 2022, 16 pages.

Miki Hidenobou et al., "Risk of edge loading and prosthesis impingement due to posterior pelvic tilting after after total hip arthroplasty," Clinical Biomechanics (May 2014), 29:4, 607-613.

Thomas D. Brown, John J. Callaghan, "Impingement in total hip replacement: mechanisms and consequences," Current Orthopaedics (2008), 22, 376-391.

Myers et al., "Effect of intraoperative treatment options on hip joint stability following total hip arthroplasty," J Orthop Res. (2022), 40, 604-613.

Gibbons et al., "Development of a statistical shape-function model of the implanted knee for real-time prediction of joint mechanics," Journal of Biomechanics, 2019, pp. 55-63.

Zhu et al., "Quantification of Pelvic Tilt in Total Hip Arthroplasty," Clinical Orthopaedics and Related Research, Aug. 28, 2009, pp. 571-575, vol. 468(2), Springer.

Ezquerra et al., "Range of Movement for Impingement and Dislocation Avoidance in Total Hip Replacement Predicted by Finite Element Model," J. Med. Biol. Eng., Jan. 21, 2017, pp. 26-34, vol. 37, Springer.

Mahboba et al., "Improving of artificial hip joint design by studying multiple angles of articulation between femoral head and acetabular liner," International Journal of Energy and Environment, Jul. 31, 2019, pp. 195-210, vol. 10(4), International Energy & Environment Foundation.

Alvarez et al., "Fluoroscopic Imaging of Acetabular Cup Position During THA Through a Direct Anterior Approach," Orthopedics, Oct. 2013, pp. 776-777, vol. 36, No. 10.

Alvarez, "Fluoroscopic Imaging of Acetabular Cup Position During THA Through a Direct Anterior Approach," Orthopedics, Jan. 2014, p. 12, vol. 37, No. 1.

Babisch et al., "The Rationale for Tilt-Adjusted Acetabular Cup Navigation," The Journal of Bone & Joint Surgery, Feb. 2008, pp. 357-365, vol. 90-A, No. 2.

Bachhal et al., "A new method of measuring acetabular cup anteversion on simulated radiographs," International Orthopaedics (SICOT), May 31, 2012, pp. 1813-1818, vol. 36, Springer.

Bergmann et al., "Hip contact forces and gait patterns from routine activities," Journal of Biomechanics, Jul. 2001, pp. 859-871, vol. 34(7), Elsevier Science Ltd.

Bergmann et al., "Standardized Loads Acting in Hip Implants," PLoS ONE, May 19, 2016, 23 pages, vol. 11(5).

Blondel et al., "Sacro-femoral-pubic angle: a coronal parameter to estimate pelvic tilt," European Spine Journal, Nov. 24, 2011, pp. 719-724, vol. 21, Springer-Verlag.

Buckland et al., "Sagittal pelvic orientation: a comparison of two methods of measurement," Bulletin of the Hospital for Joint Diseases 2017, pp. 234-240, vol. 75(4).

Chevillotte et al., "Variability in Hip Range of Motion on Clinical Examination," The Journal of Arthroplasty, Aug. 2009, pp. 693-697, vol. 24(5), Elsevier, Inc.

Cuptimize, Inc., Traditional 510(k) Application for Cuptimize Software, submitted confidentially to the U.S. Food and Drug Administration on Dec. 14, 2020, 215 pages (partially redacted).

Depuy Orthopaedics, Inc., Excerpts from Traditional 510(k) Application for DePuy CUPTIMIZE Advanced, submitted confidentially to the U.S. Food and Drug Administration on May 24, 2023, 22 pages.

Depuy Synthes Products, Inc., Corrected Request for Supplemental Examination of U.S. Pat. No. 11,107,586, assigned Conrol U.S. Appl. No. 96/050,073, filed Dec. 24, 2024, 106 pages.

Depuy Synthes Products, Inc., Request for Supplemental Examination of U.S. Pat. No. 11,107,586, assigned Conrol U.S. Appl. No. 96/050,073, filed Dec. 6, 2024, 81 pages.

Depuy Synthes Products, Inc., Response to Non-Final Office Action in Control No. U.S. Appl. No. 96/050,073, filed Jul. 9, 2025, 14 pages.

Eftekhary et al., "A systematic approach to the hip-spine relationship and its applications to total hip arthroplasty," The Bone & Joint Journal, Jul. 2019, pp. 808-816, vol. 101-B, No. 7.

Esposito et al., "Biplanar Low-Dose Radiography Is Accurate for Measuring Combined Anteversion After Total Hip Arthroplasty," HSS Journal, Feb. 5, 2019, pp. 23-29, vol. 16, No. 1, Springer Nature.

European Patent Office, Communication with Extended European Search Report for European Patent Application No. 21828607.8, Jul. 2, 2024, 12 pages.

European Patent Office, International Search Report and Written Opinion for International Application No. PCT/ EP2024/076483, Feb. 24, 2025, 24 pages.

Goodell et al., "Computer Navigation vs. Conventional Overlay Methods in Direct Anterior Total Hip Arthroplasty: A Single Surgeon Experience," Cureus, Oct. 4, 2022, 10 pages, vol. 14(10).

Heckmann et al., "Late Dislocation Following Total Hip Arthroplasty: Spinopelvic Imbalance as a Causative Factor," Journal of Bone and Joint Surgery, Nov. 7, 2018, pp. 1845-1853, vol. 100-A, The Journal of Bone and Joint Surgery, Incorporated.

Hofmann et al., "Minimizing Leg-Length Inequality in Total Hip Arthroplasty: Use of Preoperative Templating and an Intraoperative X-Ray," The American Journal of Orthopedics, Jan. 2008, pp. 18-23, vol. 37(1).

Imai et al., "Correlation of tilt of the anterior pelvic plane angle with anatomical pelvic tilt and morphological configuration of the acetabulum in patients with developmental dysplasia of the hip: a cross-sectional study," Journal of Orthopaedic Surgery and Research, Oct. 17, 2019, 7 pages, vol. 14, No. 323, Springer Nature.

Inaba et al., "Preoperative planning for implant placement with consideration of pelvic tilt in total hip arthroplasty: posoperative efficacy evaluation," BMC Musculoskeletal Disorders, Jul. 13, 2016, 7 pages, vol. 17, No. 280, CrossMark.

Jaramaz et al., "CupAlign: Computer-Assisted Postoperative Radiographic Measurement of Acetabular Components Following Total Hip Arthroplasty," Medical Image Computing and Computer Assisted Intervention (MICCAI), 1999, pp. 876-882, Springer-Verlag.

Jointpoint, Inc., JointPoint User Guide Version 3.4, Oct. 14, 2018, 92 pages.

(56) References Cited

OTHER PUBLICATIONS

Kleeman-Forsthuber et al., "Reliability of Spinopelvic Measurements That May Influence the Cup Position in Total Hip Arthroplasty," The Journal of Arthroplasty, Jun. 24, 2020, pp. 3758-3764, vol. 35, Elsevier Inc.

Labronici et al., "Positioning of the acetabular component in cemented prostheses—radiograph calculation," Revista Brasileira de Ortopedia (English Edition), 2013, pp. 62-68, vol. 48(1), Elsevier Editora Ltda.

Larose et al., "Post-Operative Measurement of Acetabular Cup Position Using X-ray/CT Registration," Medical Image Computing and Computer-Assisted Intervention (MICCAI), 2000, pp. 1104-1113, Springer-Verlag.

Lewinnek et al., "Dislocations after total hip-replacement arthroplasties," The Journal of Bone and Joint Surgery, Mar. 1978, pp. 217-220, vol. 60-A(2).

Liaw et al., "A New Tool for Measuring Cup Orientation in Total Hip Arthroplasties from Plain Radiographs," Clinical Orthopaedics and Related Research, Oct. 2006, pp. 134-139, vol. 451, Lippincott Wiliams & Wilkins.

Lo Re et al., "Sacro-Femoral-Pubic Angle and Acetabular Cup Anteversion in Total Hip Arthroplasty," EC Orthopaedics, May 31, 2019, pp. 429-437, vol. 10(6).

Lu et al., "Reliability and Validity of Measuring Acetabular Component Orientation by Plain Anteroposterior Radiographs," Clinical Orthopaedics and Related Research, May 4, 2013, pp. 2987-2994, vol. 471, Springer.

Maratt et al., "Pelvic tilt in patients undergoing total hip arthroplasty: when does it matter?" Author Manuscript, 2014, 15 pages, Elsevier Inc.

Matta et al., "Single-Incision Anterior Approach for Total Hip Arthroplasty on an Orthopaedic Table," Clinical Orthopaedics and Related Research, Dec. 2005, pp. 115-124, vol. 441, Lippincott Williams & Wilkins.

Mccarthy et al., "The Effect of Pelvic Tilt and Femoral Head Size on Hip Range-of-Motion to Impingement," The Journal of Arthroplasty, Jun. 15, 2017, pp. 3544-3549, vol. 32, Elsevier, Inc.

Murphy et al., "The Safe Zone Range for Cup Anteversion Is Narrower Than for Inclination in THA," Clinical Orthopaedics and Related Research, Jan. 17, 2018, pp. 325-335, vol. 476, No. 2, Wolters Kluwer.

Murray, "The definition and measurement of acetabular orientation," The Journal of Bone and Joint Surgery, 1993, pp. 228-232, vol. 75-B.

Myers et al., "Spinopelvic Mobility in THA and Lumbar Fusion Patients Across a Range of Common Functional X-ray Positions," Annual Meeting of Orthopaedic Research Society, Feb. 2022, Tampa Bay, FL.

Penney et al., "Postoperative Calculation of Acetabular Cop Position Using 2-D-3-D Registration," IEEE Transactions on Biomedical Engineering, Jul. 2007, pp. 1342-1348, vol. 54(7), IEEE.

Philippot et al., "Pelvic Balance in Sagittal and Lewinnek Reference Planes in the Standing, Supine and Sitting Positions," Orthopaedics & Traumatology: Surgery & Research, 2009, pp. 70-76, vol. 95, Elsevier Masson.

Pierrepont et al., "Patient-Specific Component Alignment in Total Hip Arthroplasty," Reconstructive Review, Dec. 2016, pp. 27-33, vol. 6(4), Joint Implant Surgery & Research Foundation.

Pierrepont et al., "Variation in functional pelvic tilt in patients undergoing total hip arthroplasty," The Bone & Joint Journal, Feb. 2017, pp. 184-191, vol. 99-B.

Pierrepont, Patient-Specific Component Alignment in Total Hip Arthroplasty, Jun. 2017, 321 pages.

Ragsdale et al., "Pelvic Tilt Evaluation From Frontal Radiographs: The Validity, Interobserver Reliability and Intraobserver Reproducibility of the Sacro-Femoral-Pubic Parameter," The Journal of Arthroplasty, Nov. 23, 2016, pp. 1665-1669, vol. 32, Elsevier Inc.

Tsukamoto et al., "Proposal of accurate cup placement procedure during total hip arthroplasty based on pelvic tilt discrepancies in the lateral position," Scientific Reports, Jul. 6, 2021, 9 pages, vol. 11, No. 13870, Springer Nature.

United States Patent & Trademark Office, International Search Report and Written Opinion for International Application No. PCT/US2021/038006, Sep. 29, 2021, 9 pages.

United States Patent & Trademark Office, Office Action in Ex Parte Reexamination Control U.S. Appl. No. 96/050,073, filed May 9, 2025, 43 pages.

United States Patent & Trademark Office, Reasons for Substantial New Question of Patentability Determination in Control U.S. Appl. No. 96/050,073, filed Feb. 14, 2025, 37 pages.

Vigdorchik et al., "2021 Otto Aufranc Award: A simple Hip-Spine Classification for total hip arthroplasty," The Bone & Joint Journal, Jul. 2021, pp. 17-24, vol. 103-B, No. 7.

Vigdorchik et al., "Prevalence of Risk Factors for Adverse Spinopelvic Mobility Among Patients Undergoing Total Hip Arthroplasty," The Journal of Arthroplasty, Jul. 2021, pp. 2371-2378, vol. 36(7), Elsevier Inc.

* cited by examiner

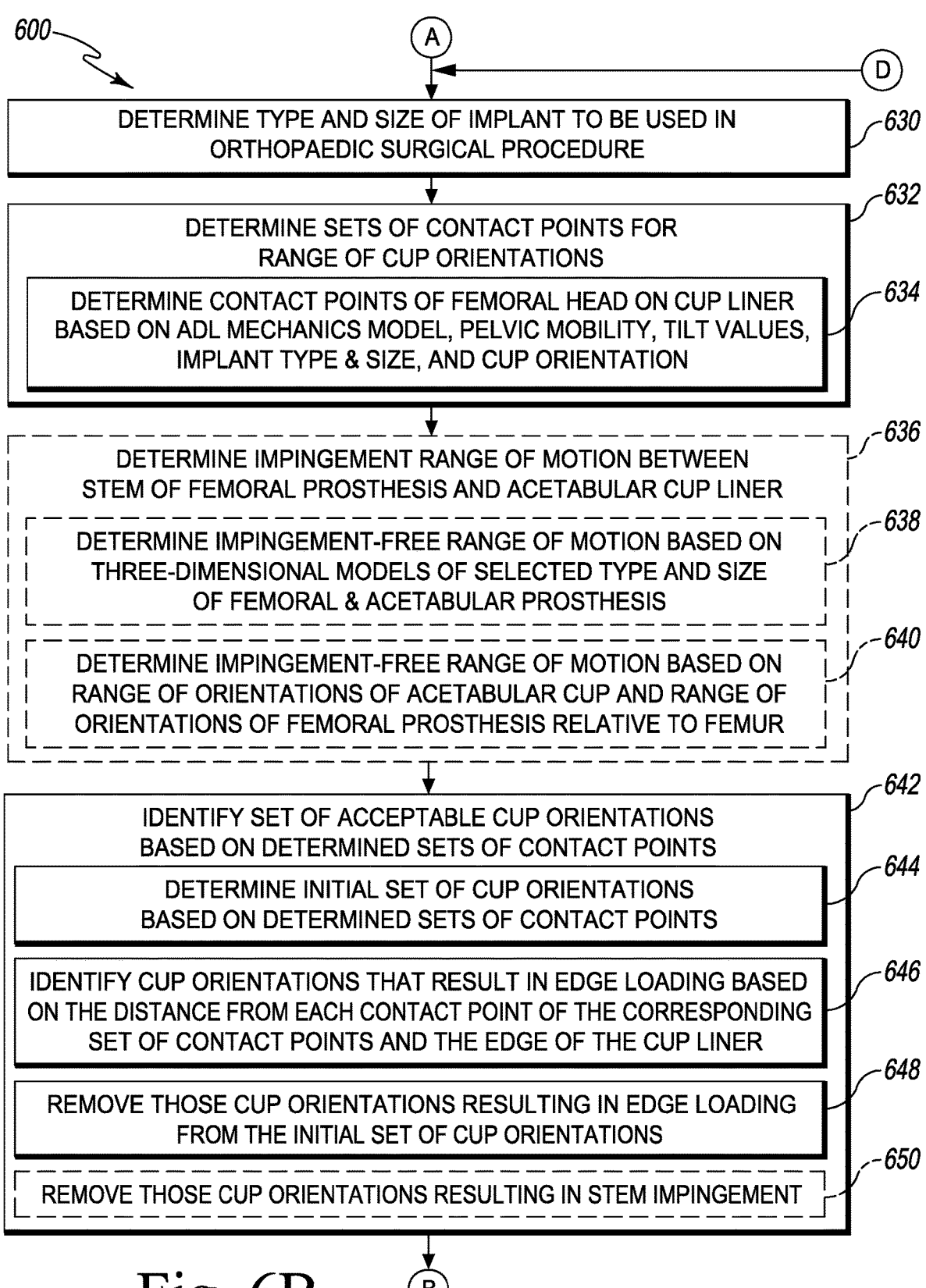

600

Ⓐ

Ⓓ

DETERMINE TYPE AND SIZE OF IMPLANT TO BE USED IN
ORTHOPAEDIC SURGICAL PROCEDURE 　 630

DETERMINE SETS OF CONTACT POINTS FOR
RANGE OF CUP ORIENTATIONS 　 632

DETERMINE CONTACT POINTS OF FEMORAL HEAD ON CUP LINER
BASED ON ADL MECHANICS MODEL, PELVIC MOBILITY, TILT VALUES,
IMPLANT TYPE & SIZE, AND CUP ORIENTATION 　 634

DETERMINE IMPINGEMENT RANGE OF MOTION BETWEEN
STEM OF FEMORAL PROSTHESIS AND ACETABULAR CUP LINER 　 636

DETERMINE IMPINGEMENT-FREE RANGE OF MOTION BASED ON
THREE-DIMENSIONAL MODELS OF SELECTED TYPE AND SIZE
OF FEMORAL & ACETABULAR PROSTHESIS 　 638

DETERMINE IMPINGEMENT-FREE RANGE OF MOTION BASED ON
RANGE OF ORIENTATIONS OF ACETABULAR CUP AND RANGE OF
ORIENTATIONS OF FEMORAL PROSTHESIS RELATIVE TO FEMUR 　 640

IDENTIFY SET OF ACCEPTABLE CUP ORIENTATIONS
BASED ON DETERMINED SETS OF CONTACT POINTS 　 642

DETERMINE INITIAL SET OF CUP ORIENTATIONS
BASED ON DETERMINED SETS OF CONTACT POINTS 　 644

IDENTIFY CUP ORIENTATIONS THAT RESULT IN EDGE LOADING BASED
ON THE DISTANCE FROM EACH CONTACT POINT OF THE CORRESPONDING
SET OF CONTACT POINTS AND THE EDGE OF THE CUP LINER 　 646

REMOVE THOSE CUP ORIENTATIONS RESULTING IN EDGE LOADING
FROM THE INITIAL SET OF CUP ORIENTATIONS 　 648

REMOVE THOSE CUP ORIENTATIONS RESULTING IN STEM IMPINGEMENT 　 650

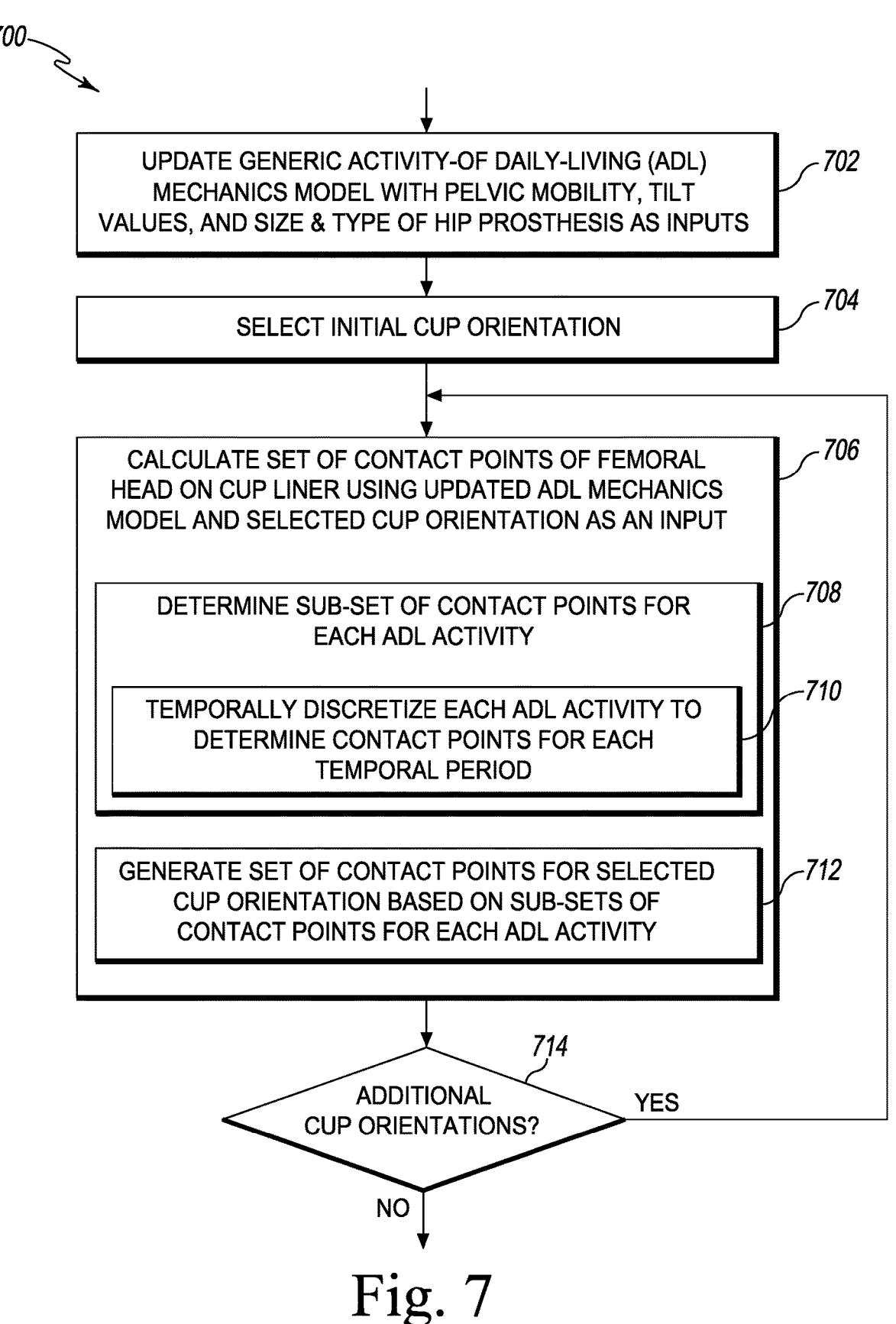

700

UPDATE GENERIC ACTIVITY-OF DAILY-LIVING (ADL) MECHANICS MODEL WITH PELVIC MOBILITY, TILT VALUES, AND SIZE & TYPE OF HIP PROSTHESIS AS INPUTS                    702

SELECT INITIAL CUP ORIENTATION                    704

CALCULATE SET OF CONTACT POINTS OF FEMORAL HEAD ON CUP LINER USING UPDATED ADL MECHANICS MODEL AND SELECTED CUP ORIENTATION AS AN INPUT                    706

DETERMINE SUB-SET OF CONTACT POINTS FOR EACH ADL ACTIVITY                    708

TEMPORALLY DISCRETIZE EACH ADL ACTIVITY TO DETERMINE CONTACT POINTS FOR EACH TEMPORAL PERIOD                    710

GENERATE SET OF CONTACT POINTS FOR SELECTED CUP ORIENTATION BASED ON SUB-SETS OF CONTACT POINTS FOR EACH ADL ACTIVITY                    712

ADDITIONAL CUP ORIENTATIONS?                    714

YES

Figure 8A:
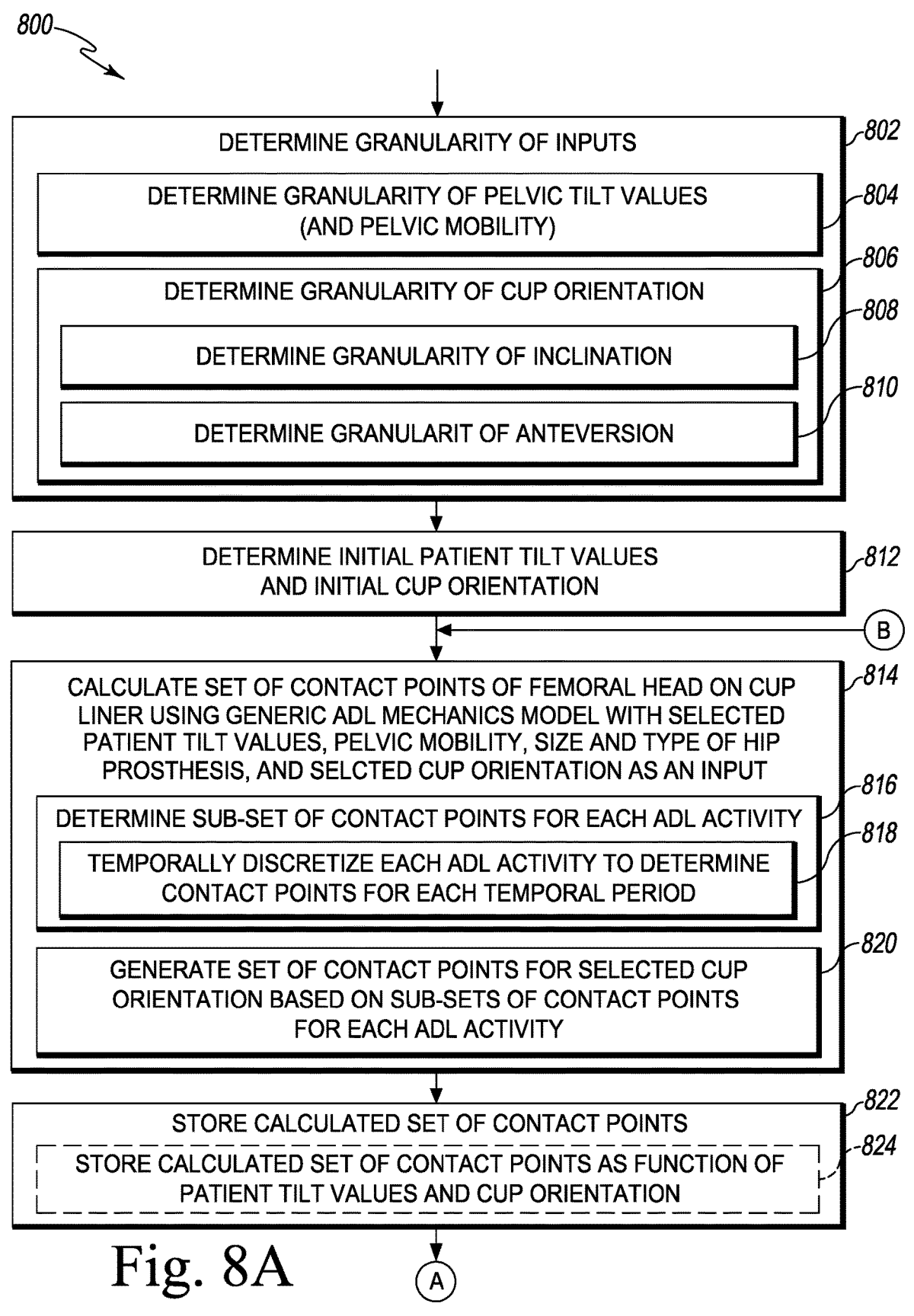

DETERMINE GRANULARITY OF INPUTS — *802*

DETERMINE GRANULARITY OF PELVIC TILT VALUES (AND PELVIC MOBILITY) — *804*

— *806*

DETERMINE GRANULARITY OF CUP ORIENTATION — *808*

DETERMINE GRANULARITY OF INCLINATION

— *810*

DETERMINE GRANULARIT OF ANTEVERSION

DETERMINE INITIAL PATIENT TILT VALUES AND INITIAL CUP ORIENTATION — *812*

(B)

CALCULATE SET OF CONTACT POINTS OF FEMORAL HEAD ON CUP LINER USING GENERIC ADL MECHANICS MODEL WITH SELECTED PATIENT TILT VALUES, PELVIC MOBILITY, SIZE AND TYPE OF HIP PROSTHESIS, AND SELCTED CUP ORIENTATION AS AN INPUT — *814*

— *816*

DETERMINE SUB-SET OF CONTACT POINTS FOR EACH ADL ACTIVITY — *818*

TEMPORALLY DISCRETIZE EACH ADL ACTIVITY TO DETERMINE CONTACT POINTS FOR EACH TEMPORAL PERIOD

— *820*

GENERATE SET OF CONTACT POINTS FOR SELECTED CUP ORIENTATION BASED ON SUB-SETS OF CONTACT POINTS FOR EACH ADL ACTIVITY

STORE CALCULATED SET OF CONTACT POINTS — *822*

— *824*

STORE CALCULATED SET OF CONTACT POINTS AS FUNCTION OF PATIENT TILT VALUES AND CUP ORIENTATION

Fig. 8A (A)

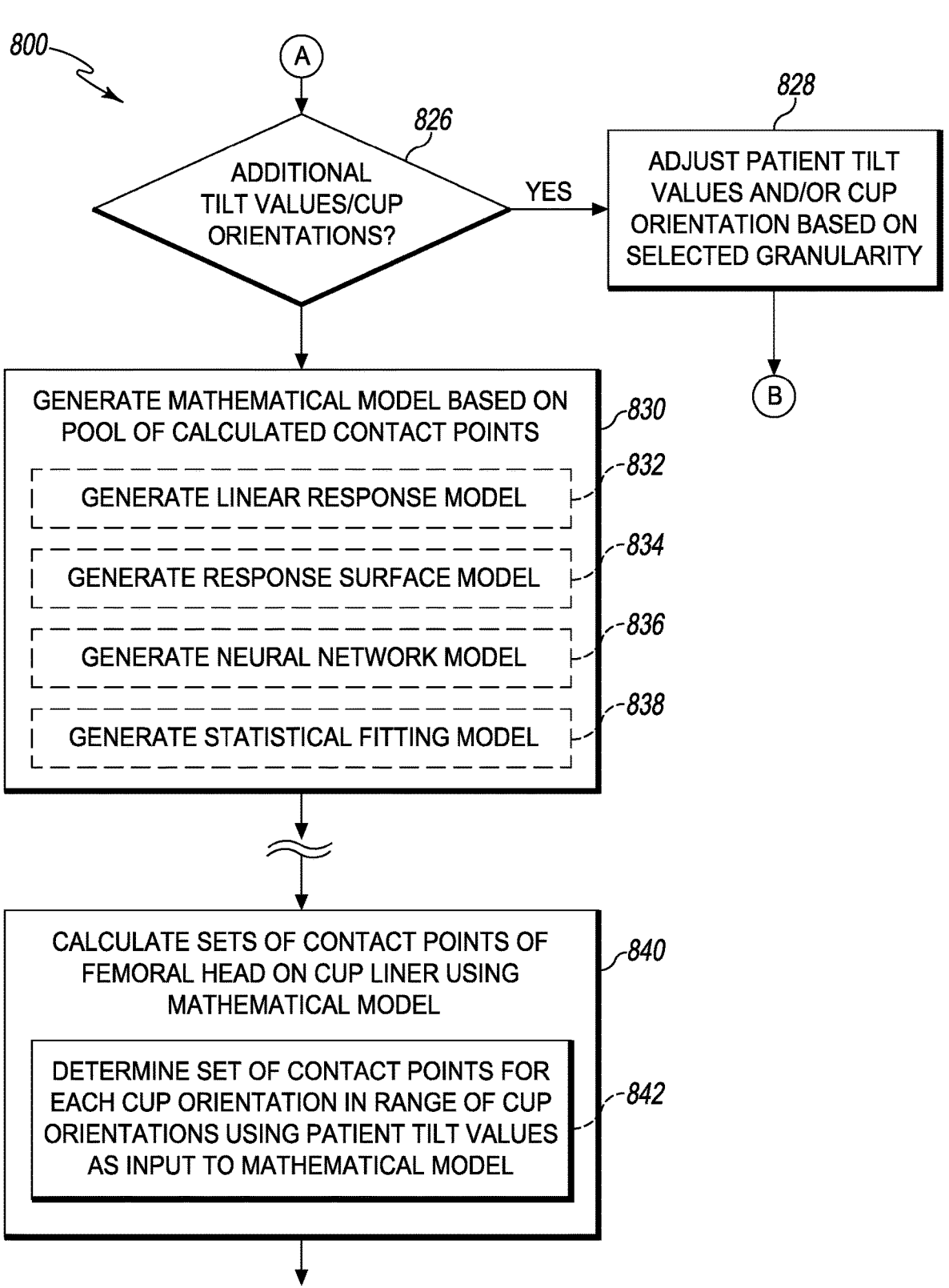

*800*

Ⓐ

*826*

ADDITIONAL
TILT VALUES/CUP
ORIENTATIONS?

YES →

*828*

ADJUST PATIENT TILT
VALUES AND/OR CUP
ORIENTATION BASED ON
SELECTED GRANULARITY

Ⓑ

GENERATE MATHEMATICAL MODEL BASED ON
POOL OF CALCULATED CONTACT POINTS          *830*

GENERATE LINEAR RESPONSE MODEL          *832*

GENERATE RESPONSE SURFACE MODEL          *834*

GENERATE NEURAL NETWORK MODEL          *836*

GENERATE STATISTICAL FITTING MODEL          *838*

CALCULATE SETS OF CONTACT POINTS OF
FEMORAL HEAD ON CUP LINER USING
MATHEMATICAL MODEL          *840*

DETERMINE SET OF CONTACT POINTS FOR
EACH CUP ORIENTATION IN RANGE OF CUP
ORIENTATIONS USING PATIENT TILT VALUES
AS INPUT TO MATHEMATICAL MODEL          *842*

Fig. 8B

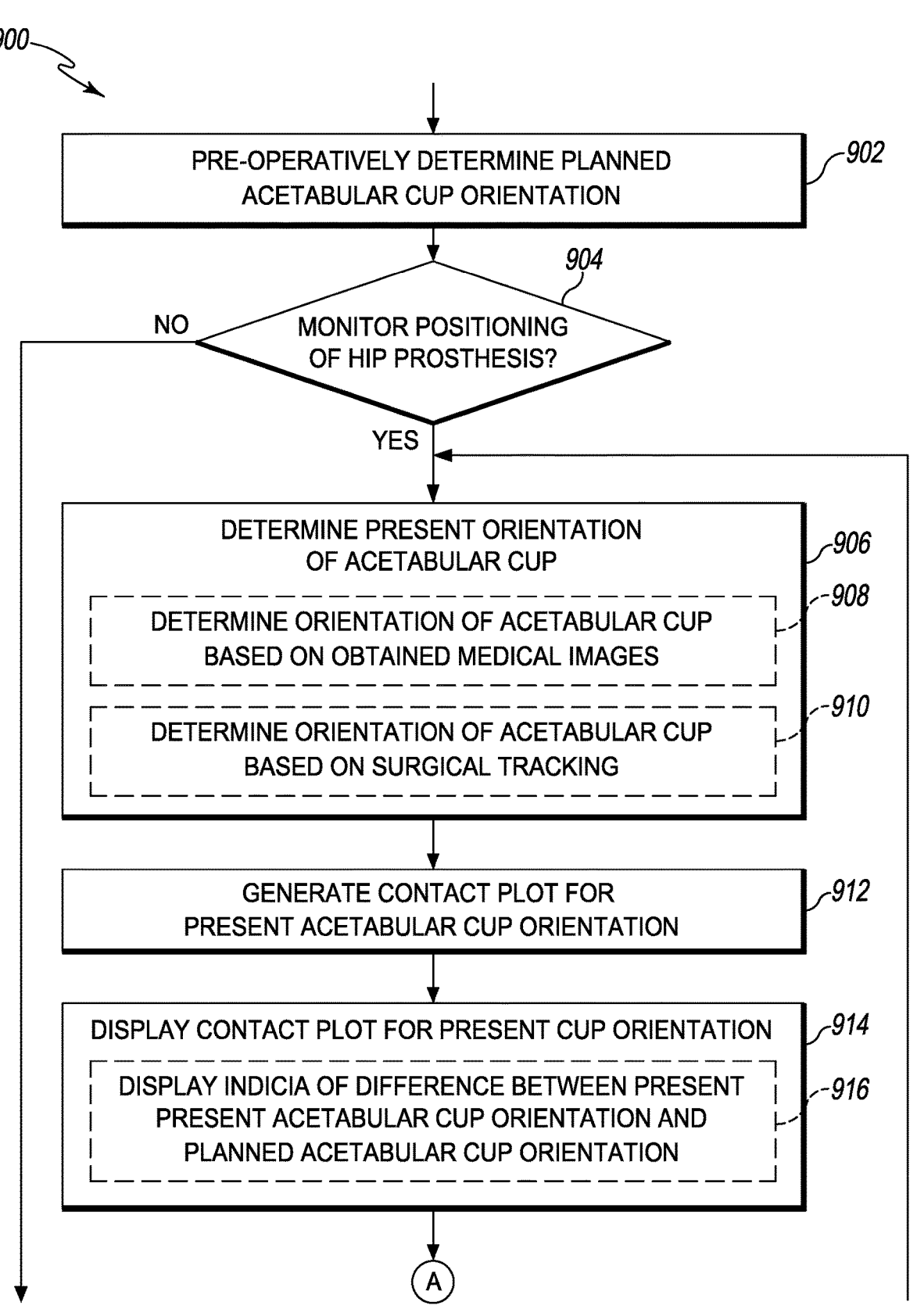

900

PRE-OPERATIVELY DETERMINE PLANNED
ACETABULAR CUP ORIENTATION ──902

MONITOR POSITIONING
OF HIP PROSTHESIS? ──904

NO

YES

DETERMINE PRESENT ORIENTATION
OF ACETABULAR CUP ──906

DETERMINE ORIENTATION OF ACETABULAR CUP
BASED ON OBTAINED MEDICAL IMAGES ──908

DETERMINE ORIENTATION OF ACETABULAR CUP
BASED ON SURGICAL TRACKING ──910

GENERATE CONTACT PLOT FOR
PRESENT ACETABULAR CUP ORIENTATION ──912

DISPLAY CONTACT PLOT FOR PRESENT CUP ORIENTATION ──914

DISPLAY INDICIA OF DIFFERENCE BETWEEN PRESENT
PRESENT ACETABULAR CUP ORIENTATION AND
PLANNED ACETABULAR CUP ORIENTATION ──916

WALK

1204

STEP DOWN

1206

SIT-TO STAND

Figure 21A:
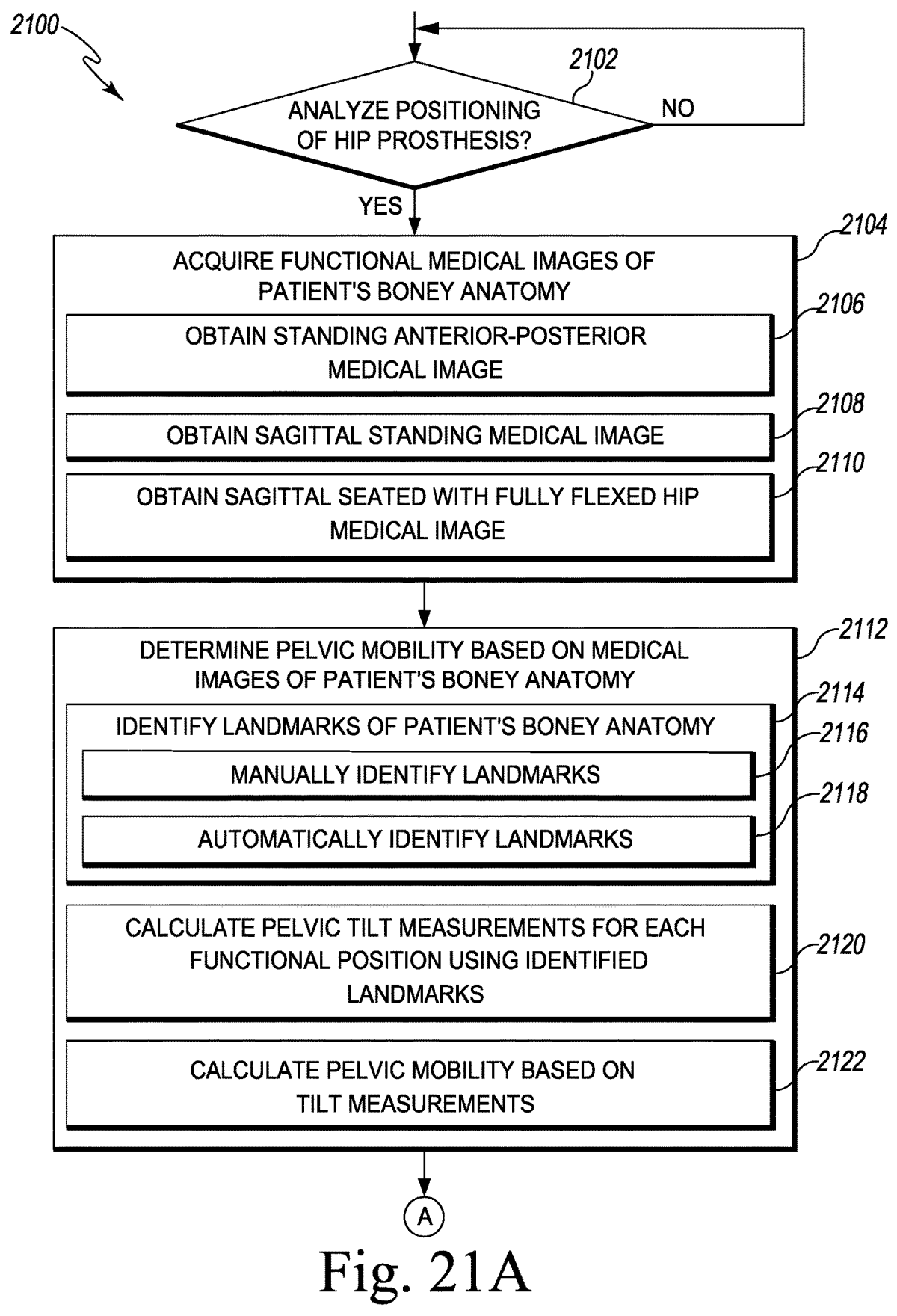

2100

2102

ANALYZE POSITIONING OF HIP PROSTHESIS? — NO

YES

ACQUIRE FUNCTIONAL MEDICAL IMAGES OF PATIENT'S BONEY ANATOMY — 2104

OBTAIN STANDING ANTERIOR-POSTERIOR MEDICAL IMAGE — 2106

OBTAIN SAGITTAL STANDING MEDICAL IMAGE — 2108

OBTAIN SAGITTAL SEATED WITH FULLY FLEXED HIP MEDICAL IMAGE — 2110

DETERMINE PELVIC MOBILITY BASED ON MEDICAL IMAGES OF PATIENT'S BONEY ANATOMY — 2112

IDENTIFY LANDMARKS OF PATIENT'S BONEY ANATOMY — 2114

MANUALLY IDENTIFY LANDMARKS — 2116

AUTOMATICALLY IDENTIFY LANDMARKS — 2118

CALCULATE PELVIC TILT MEASUREMENTS FOR EACH FUNCTIONAL POSITION USING IDENTIFIED LANDMARKS — 2120

CALCULATE PELVIC MOBILITY BASED ON TILT MEASUREMENTS — 2122

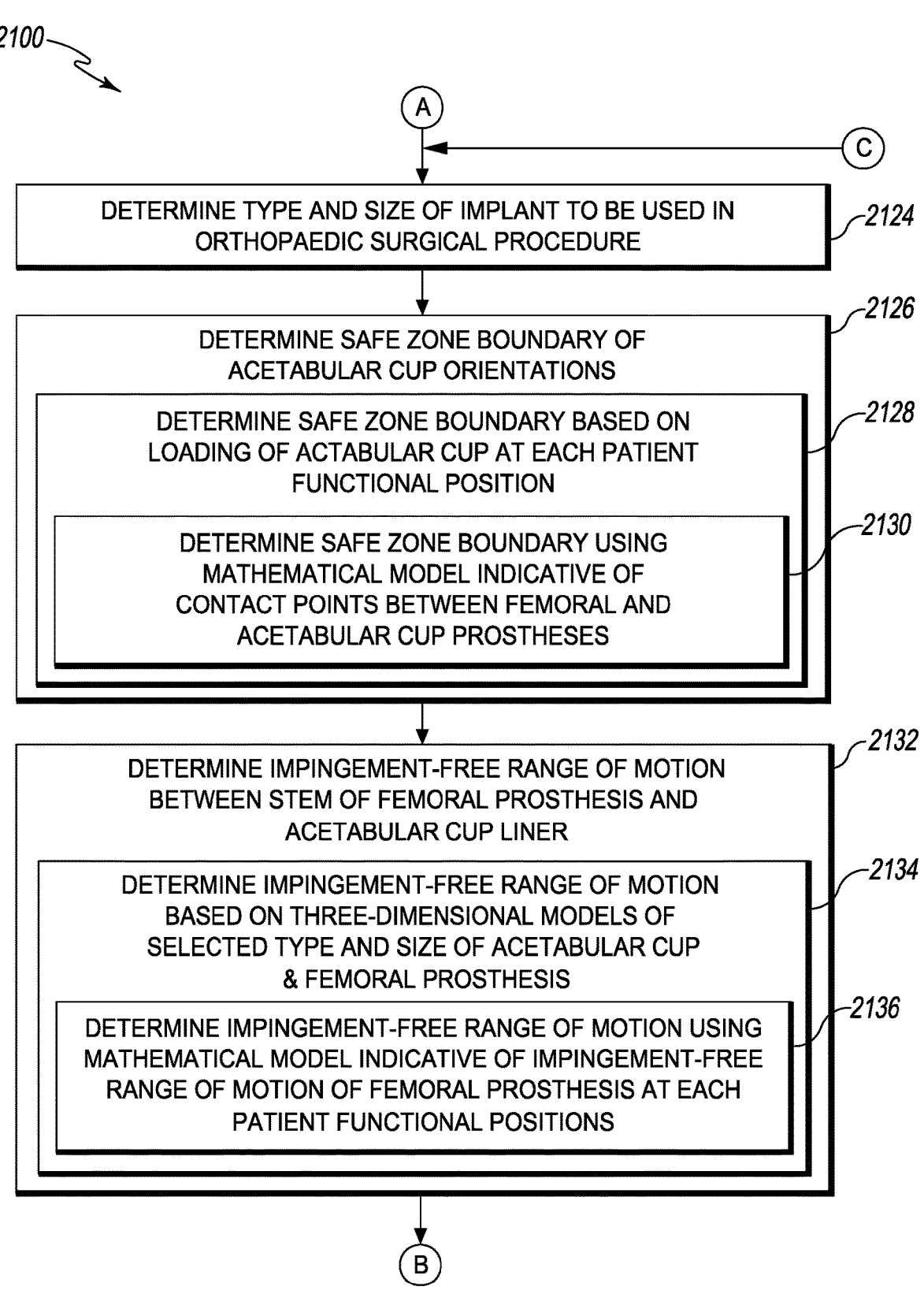

2100

Ⓐ           Ⓒ

DETERMINE TYPE AND SIZE OF IMPLANT TO BE USED IN ORTHOPAEDIC SURGICAL PROCEDURE — 2124

DETERMINE SAFE ZONE BOUNDARY OF ACETABULAR CUP ORIENTATIONS — 2126

DETERMINE SAFE ZONE BOUNDARY BASED ON LOADING OF ACTABULAR CUP AT EACH PATIENT FUNCTIONAL POSITION — 2128

DETERMINE SAFE ZONE BOUNDARY USING MATHEMATICAL MODEL INDICATIVE OF CONTACT POINTS BETWEEN FEMORAL AND ACETABULAR CUP PROSTHESES — 2130

DETERMINE IMPINGEMENT-FREE RANGE OF MOTION BETWEEN STEM OF FEMORAL PROSTHESIS AND ACETABULAR CUP LINER — 2132

DETERMINE IMPINGEMENT-FREE RANGE OF MOTION BASED ON THREE-DIMENSIONAL MODELS OF SELECTED TYPE AND SIZE OF ACETABULAR CUP & FEMORAL PROSTHESIS — 2134

DETERMINE IMPINGEMENT-FREE RANGE OF MOTION USING MATHEMATICAL MODEL INDICATIVE OF IMPINGEMENT-FREE RANGE OF MOTION OF FEMORAL PROSTHESIS AT EACH PATIENT FUNCTIONAL POSITIONS — 2136

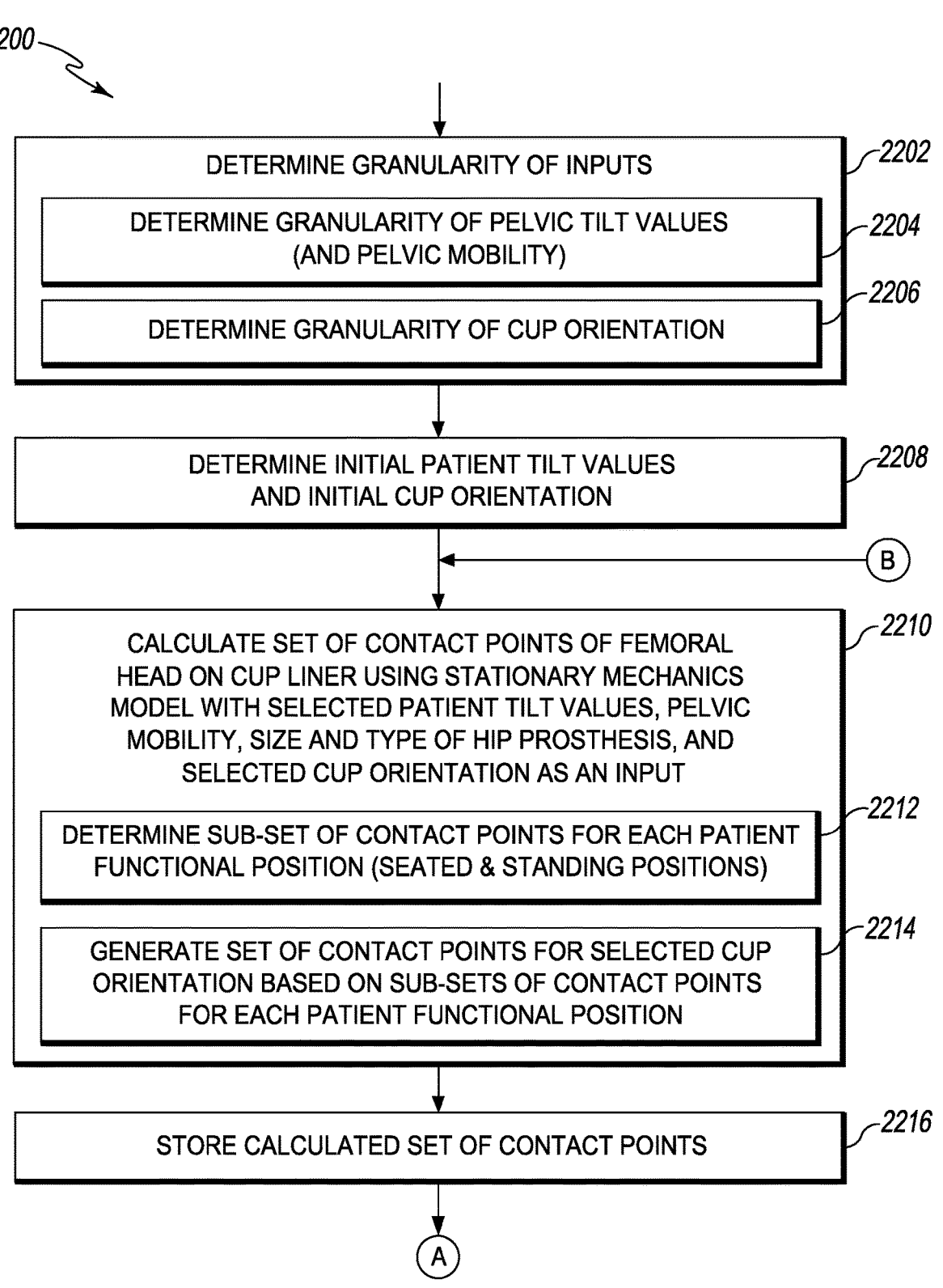

*2202*
DETERMINE GRANULARITY OF INPUTS

*2204*
DETERMINE GRANULARITY OF PELVIC TILT VALUES
(AND PELVIC MOBILITY)

*2206*
DETERMINE GRANULARITY OF CUP ORIENTATION

*2208*
DETERMINE INITIAL PATIENT TILT VALUES
AND INITIAL CUP ORIENTATION

Ⓑ

*2210*
CALCULATE SET OF CONTACT POINTS OF FEMORAL
HEAD ON CUP LINER USING STATIONARY MECHANICS
MODEL WITH SELECTED PATIENT TILT VALUES, PELVIC
MOBILITY, SIZE AND TYPE OF HIP PROSTHESIS, AND
SELECTED CUP ORIENTATION AS AN INPUT

*2212*
DETERMINE SUB-SET OF CONTACT POINTS FOR EACH PATIENT
FUNCTIONAL POSITION (SEATED & STANDING POSITIONS)

*2214*
GENERATE SET OF CONTACT POINTS FOR SELECTED CUP
ORIENTATION BASED ON SUB-SETS OF CONTACT POINTS
FOR EACH PATIENT FUNCTIONAL POSITION

*2216*
STORE CALCULATED SET OF CONTACT POINTS

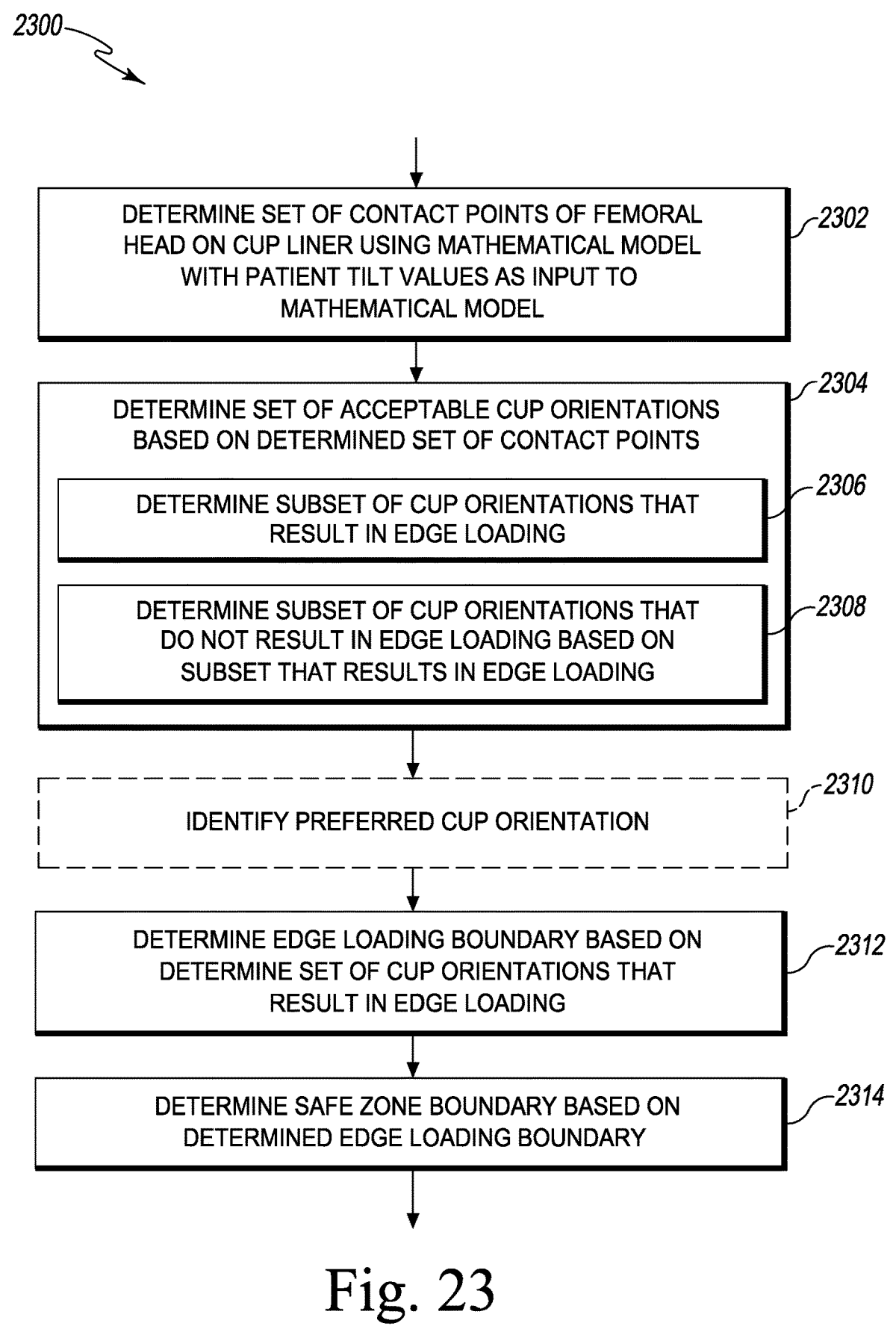

```
          │
          ▼
┌─────────────────────────────────────────┐
│ DETERMINE SET OF CONTACT POINTS OF       │──2302
│ FEMORAL HEAD ON CUP LINER USING          │
│ MATHEMATICAL MODEL WITH PATIENT TILT     │
│ VALUES AS INPUT TO MATHEMATICAL MODEL    │
└─────────────────────────────────────────┘
          │
          ▼
┌─────────────────────────────────────────┐──2304
│ DETERMINE SET OF ACCEPTABLE CUP          │
│ ORIENTATIONS BASED ON DETERMINED SET     │
│ OF CONTACT POINTS                        │
│  ┌───────────────────────────────────┐  │──2306
│  │ DETERMINE SUBSET OF CUP           │  │
│  │ ORIENTATIONS THAT RESULT IN       │  │
│  │ EDGE LOADING                      │  │
│  └───────────────────────────────────┘  │
│  ┌───────────────────────────────────┐  │──2308
│  │ DETERMINE SUBSET OF CUP           │  │
│  │ ORIENTATIONS THAT DO NOT RESULT   │  │
│  │ IN EDGE LOADING BASED ON SUBSET   │  │
│  │ THAT RESULTS IN EDGE LOADING      │  │
│  └───────────────────────────────────┘  │
└─────────────────────────────────────────┘
          │
          ▼
┌─ ─ ─ ─ ─ ─ ─ ─ ─ ─ ─ ─ ─ ─ ─ ─ ─ ─ ─ ─ ┐──2310
│                                          │
│     IDENTIFY PREFERRED CUP ORIENTATION   │
│                                          │
└─ ─ ─ ─ ─ ─ ─ ─ ─ ─ ─ ─ ─ ─ ─ ─ ─ ─ ─ ─ ┘
          │
          ▼
┌─────────────────────────────────────────┐
│ DETERMINE EDGE LOADING BOUNDARY BASED    │──2312
│ ON DETERMINE SET OF CUP ORIENTATIONS     │
│ THAT RESULT IN EDGE LOADING              │
└─────────────────────────────────────────┘
          │
          ▼
┌─────────────────────────────────────────┐
│ DETERMINE SAFE ZONE BOUNDARY BASED ON    │──2314
│ DETERMINED EDGE LOADING BOUNDARY         │
└─────────────────────────────────────────┘
          │
          ▼
```

Fig. 23

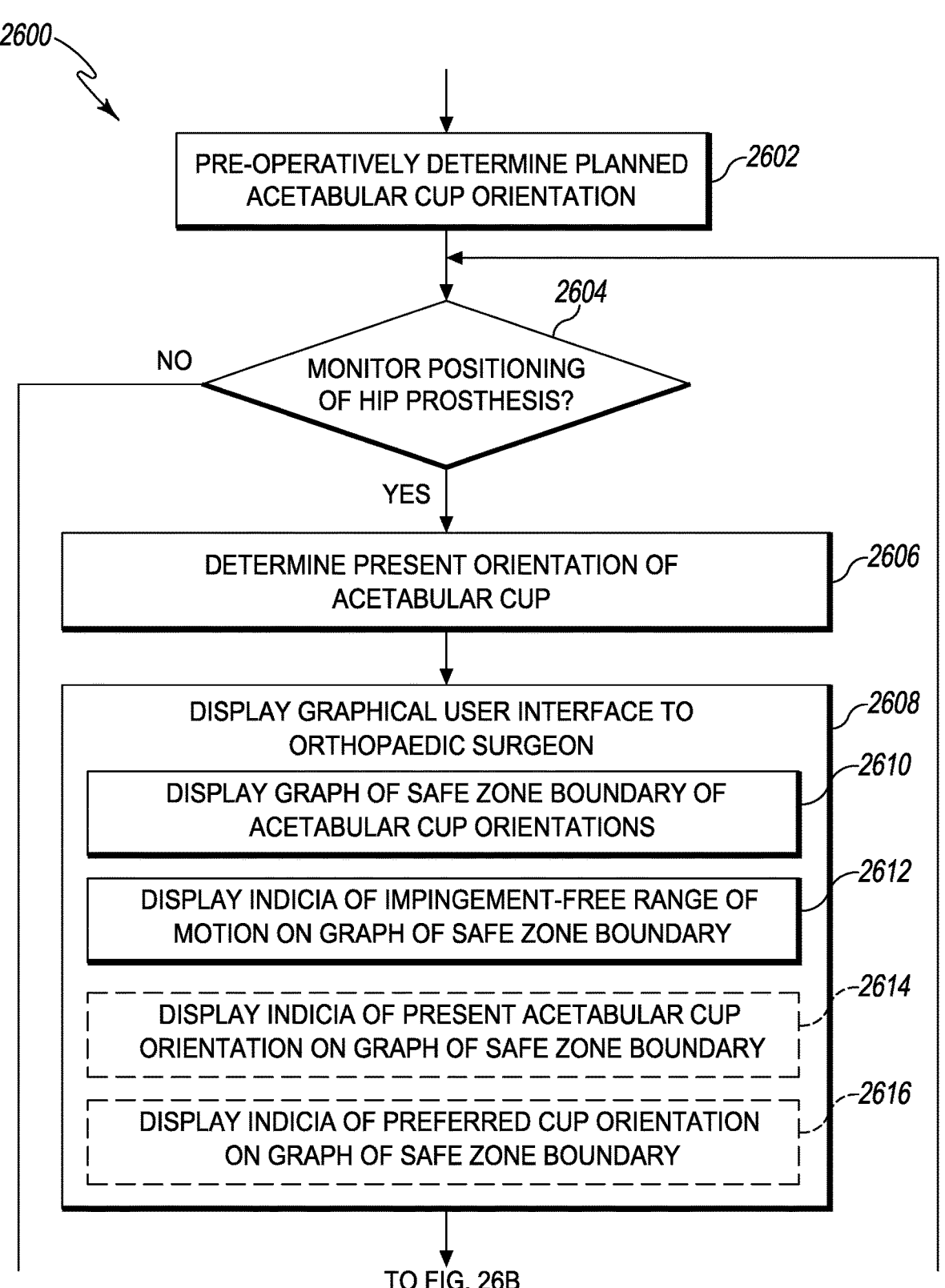

*2600*

PRE-OPERATIVELY DETERMINE PLANNED ACETABULAR CUP ORIENTATION ⟋*2602*

*2604*

NO ◄─── MONITOR POSITIONING OF HIP PROSTHESIS?

YES

DETERMINE PRESENT ORIENTATION OF ACETABULAR CUP ⟋*2606*

DISPLAY GRAPHICAL USER INTERFACE TO ORTHOPAEDIC SURGEON ⟋*2608*

DISPLAY GRAPH OF SAFE ZONE BOUNDARY OF ACETABULAR CUP ORIENTATIONS ⟋*2610*

DISPLAY INDICIA OF IMPINGEMENT-FREE RANGE OF MOTION ON GRAPH OF SAFE ZONE BOUNDARY ⟋*2612*

DISPLAY INDICIA OF PRESENT ACETABULAR CUP ORIENTATION ON GRAPH OF SAFE ZONE BOUNDARY ⟋*2614*

DISPLAY INDICIA OF PREFERRED CUP ORIENTATION ON GRAPH OF SAFE ZONE BOUNDARY ⟋*2616*

APPARATUS, SYSTEM, AND METHOD FOR DETERMINING A POSITION OF A HIP PROSTHESIS IN A BONE OF A PATIENT

CROSS-REFERENCE TO RELATED APPLICATIONS

This application claims priority under 35 U.S.C. § 119(e) to U.S. Provisional Patent Application No. 63/132,991, entitled "APPARATUS, SYSTEM, AND METHOD FOR DETERMINING A POSITION OF A HIP PROSTHESIS IN A BONE OF A PATIENT," which was filed on Dec. 31, 2020, which is incorporated by reference in its entirety.

TECHNICAL FIELD

The present disclosure relates generally to computer-assisted surgery systems for use in the performance of orthopaedic procedures, and more particularly to technologies for determining a position of a hip prosthesis in a bone of a patient.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral component prosthesis. The acetabular prosthetic component is implanted into the patient's acetabulum and generally includes an outer shell configured to engage the acetabulum and an inner bearing or cup liner coupled to the shell. The femoral component prosthesis is implanted into the patient's femur and generally includes a stem component embedded into the medullary canal the femur and a femoral head component. The femoral head component is configured to engage the cup liner of the acetabular to form a ball and socket joint that approximates the natural hip joint.

Typically, an orthopaedic surgeon may perform some amount of pre-operative planning to, for example, determine a positioning of the hip prosthesis. Such pre-operative planning may be performed manually by the orthopaedic surgeon based on an examination of the patient and/or pre-operative medical images of the patient's boney anatomy. However, such pre-operative planning is typically unable to provide the orthopaedic surgeon with an understanding of the patent hip mechanics, and thereby performance of the hip prosthesis, that may result from the planned positioning of the hip prosthesis.

SUMMARY

According to an aspect of the present disclosure, a system for determining a position of a hip prosthesis in an acetabulum of a patient, the system comprising one or more processors and one or more memory communicatively coupled to the one or more processors. The one or more memory may include instructions that, in response to execution by the one or more processors, cause the system to acquire a set of medical images of a hip of the patient; determine pelvic tilt measurements of a pelvis of the patient based on the set of medical images, wherein each pelvic tilt measurement is indicative of a range of motion of the hip of the patient when the hip is placed in a corresponding functional position; determine a type and size of a femoral prosthesis and an acetabular cup of the hip prosthesis; determine a set of contact points between a femoral head of the femoral prosthesis and a cup liner of the acetabular cup based on a generic activities-of-daily-living (ADLs) mechanics model using the type and size of the femoral prosthesis and the acetabular cup, the pelvic tilt measurements, and an orientation of the acetabular cup relative to the acetabulum of the patient shown in the set of medical images as inputs to the generic ADL mechanics model, wherein the generic ADL mechanics model is indicative of mechanical motion of a hip exhibited during performance of a set of ADL; and generate a contact plot based on the set of contact points. The contact plot may include indicia for each contact point in the set of contact points; and display the contact plot on a display.

According to another aspect of the disclosure, a method for determining a position of a hip prosthesis in an acetabulum of a patient may include acquiring, by a computer system, a set of medical images of a hip of the patient; determining, by the computer system, pelvic tilt measurements of a pelvis of the patient based on the set of medical images, wherein each pelvic tilt measurement is indicative of a range of motion of the hip of the patient when the hip is placed in a corresponding functional position; determining, by the computer system, a type and size of a femoral prosthesis and an acetabular cup of the hip prosthesis; determining, by the computer system, a set of contact points between a femoral head of the femoral prosthesis and a cup liner of the acetabular cup based on a generic activities-of-daily-living (ADL) mechanics model using the type and size of the femoral prosthesis and the acetabular cup, the pelvic tilt measurements, and an orientation of the acetabular cup relative to the acetabulum of the patient shown in the set of medical images as inputs to the generic ADL mechanics model, wherein the generic ADL mechanics model is indicative of mechanical motion of a hip exhibited during performance of a set of ADL; generating, by the computer system, a contact plot based on the set of contact points, wherein the contact plot includes an indicia for each contact point in the set of contact points; and displaying, by the computer system, the contact plot on a display.

According to yet a further aspect of the disclosure, one or more non-transitory, machine-readable storage media comprising a plurality of instructions stored thereon that, in response to execution, cause a computer system to determine pelvic tilt measurements of a hip of the patient based on a set of medical images of the hip, wherein each pelvic tilt measurement is indicative of a range of motion of the hip of the patient when the hip is placed in a corresponding functional position; determine a set of contact points between a femoral head of a femoral prosthesis and a cup liner of an acetabular cup based on a generic activities-of-daily-living (ADL) mechanics model using a type and a size of the femoral prosthesis, a type and a size of the acetabular cup, the pelvic tilt measurements, and an orientation of the acetabular cup relative to an acetabulum of the patient shown in the set of medical images as inputs to the generic ADL mechanics model, wherein the generic ADL mechanics model is indicative of mechanical motion of a hip exhibited during performance of a set of ADL; generate a contact plot based on the set of contact points, wherein the contact plot includes an indicia for each contact point in the set of contact points; and display the contact plot on a display.

According to yet another aspect of the present disclosure, a system for determining a position of a hip prosthesis in an acetabulum of a patient may include one or more processors and one or more memory communicatively coupled to the one or more processors. The one or more memory may include instructions that, in response to execution by the one or more processors, cause the system to determine pelvic tilt measurements of a hip of the patient based on a set of medical images of the hip, wherein each pelvic tilt measurement is indicative of a range of motion of the hip of the patient when the hip is placed in a corresponding functional position; determine a plurality of sets of contact points between a femoral head of a femoral prosthesis and a cup liner of an acetabular cup based on a generic activities-of-daily-living (ADL) mechanics model using a type and a size of the femoral prosthesis, a type and a size of the acetabular cup, the pelvic tilt measurements, and a plurality of orientations of the acetabular cup relative to the acetabulum of the patient as inputs to the ADL mechanics model, wherein each set of contact points of the plurality of sets of contact points corresponds to a different orientation of the acetabular cup of the plurality of orientations of the acetabular cup used as an input to the generic ADL mechanics model; generate a contact plot for each set of contact points of the plurality of contact points, wherein each contact plot includes an indicia for each contact point in the corresponding set of contact points; pre-operatively identify a planned orientation of the acetabular cup relative to the acetabulum of the patient based on the contact plots; determine, intra-operatively during the performance of an orthopaedic surgical procedure on the hip of the patient, a present orientation of the acetabular cup relative to the acetabulum of the patient; determine another set of contact points between the femoral head of the femoral prosthesis and the cup liner of the acetabular cup based on the generic ADL mechanics model using the type and the size of the femoral prosthesis, the type and the size of the acetabular cup, the pelvic tilt measurements, and the present orientation of the acetabular cup relative to the acetabulum of the patient as inputs to the ADL mechanics model; generate another contact plot for the another set of contact points, wherein the another contact plot includes an indicia for each contact point in the another set of contact point; and display the another contact plot on a display.

According to yet another aspect of the present disclosure, a method for determining a position of a hip prosthesis in an acetabulum of a patient may include determining, by a computer system, pelvic tilt measurements of a hip of the patient based on a set of medical images of the hip, wherein each pelvic tilt measurement is indicative of a range of motion of the hip of the patient when the hip is placed in a corresponding functional position; determining, by the computer system, a plurality of sets of contact points between a femoral head of a femoral prosthesis and a cup liner of an acetabular cup based on a generic activities-of-daily-living (ADL) mechanics model using a type and a size of the femoral prosthesis, a type and a size of the acetabular cup, the pelvic tilt measurements, and a plurality of orientations of the acetabular cup relative to the acetabulum of the patient as inputs to the ADL mechanics model, wherein each set of contact points of the plurality of sets of contact points corresponds to a different orientation of the acetabular cup of the plurality of orientations of the acetabular cup used as an input to the generic ADL mechanics model; generating, by the computer system, a contact plot for each set of contact points of the plurality of contact points, wherein each contact plot includes an indicia for each contact point in the corresponding set of contact points; pre-operatively identifying, by the computer system, a planned orientation of the acetabular cup relative to the acetabulum of the patient based on the contact plots; determining, by the computer system and intra-operatively during the performance of an orthopaedic surgical procedure on the hip of the patient, a present orientation of the acetabular cup relative to the acetabulum of the patient; determining, by the computer system, another set of contact points between the femoral head of the femoral prosthesis and the cup liner of the acetabular cup based on the generic ADL mechanics model using the type and the size of the femoral prosthesis, the type and the size of the acetabular cup, the pelvic tilt measurements, and the present orientation of the acetabular cup relative to the acetabulum of the patient as inputs to the ADL mechanics model; generating, by the computer system, another contact plot for the another set of contact points, wherein the another contact plot includes an indicia for each contact point in the another set of contact point; and displaying, by the computer system, the another contact plot on a display.

According to yet another aspect of the present disclosure, one or more non-transitory, machine-readable storage media may include a plurality of instructions stored thereon that, in response to execution, cause a computer system to determine pelvic tilt measurements of a hip of the patient based on a set of medical images of the hip, wherein each pelvic tilt measurement is indicative of a range of motion of the hip of the patient when the hip is placed in a corresponding functional position; determine a plurality of sets of contact points between a femoral head of a femoral prosthesis and a cup liner of an acetabular cup based on a generic activities-of-daily-living (ADL) mechanics model using a type and a size of the femoral prosthesis, a type and a size of the acetabular cup, the pelvic tilt measurements, and a plurality of orientations of the acetabular cup relative to the acetabulum of the patient as inputs to the ADL mechanics model, wherein each set of contact points of the plurality of sets of contact points corresponds to a different orientation of the acetabular cup of the plurality of orientations of the acetabular cup used as an input to the generic ADL mechanics model; generate a contact plot for each set of contact points of the plurality of contact points, wherein each contact plot includes an indicia for each contact point in the corresponding set of contact points; pre-operatively identify a planned orientation of the acetabular cup relative to the acetabulum of the patient based on the contact plots; determine, intra-operatively during the performance of an orthopaedic surgical procedure on the hip of the patient, a present orientation of the acetabular cup relative to the acetabulum of the patient; determine another set of contact points between the femoral head of the femoral prosthesis and the cup liner of the acetabular cup based on the generic ADL mechanics model using the type and the size of the femoral prosthesis, the type and the size of the acetabular cup, the pelvic tilt measurements, and the present orientation of the acetabular cup relative to the acetabulum of the patient as inputs to the ADL mechanics model; generate another contact plot for the another set of contact points, wherein the another contact plot includes an indicia for each contact point in the another set of contact point; and display the another contact plot on a display.

According to yet a further aspect of the present disclosure, a method of performing an orthopaedic surgical procedure on a hip of a patient to implant a hip prosthesis having a femoral prosthesis and an acetabular cup may include operating, pre-operatively to the orthopaedic surgical procedure, a computer system to determine a plurality of sets of contact points between a femoral head of the femoral prosthesis and a cup liner of the acetabular cup based on a generic activities-of-daily-living (ADL) mechanics model using a type and a size of the femoral prosthesis, a type and a size of the acetabular cup, pelvic tilt measurements of the patient, and a plurality of orientations of the acetabular cup relative to the acetabulum of the patient as inputs to the ADL mechanics model, wherein the generic ADL mechanics model is indicative of mechanical motion of a hip exhibited during performance of a set of ADL and wherein each set of contact points of the plurality of sets of contact points corresponds to a different orientation of the acetabular cup of the plurality of orientations of the acetabular cup used as an input to the generic ADL mechanics model and (ii) display a contact plot on a display for each set of contact points, wherein each contact plot includes indicia for each contact point in each corresponding set of contact points; selecting, pre-operatively, an orientation for the acetabular cup relative to the acetabulum of the patient based on the contact plots displayed on the display; and performing the orthopaedic surgical procedure on the hip of a patient using the selected orientation for the acetabular cup to implant the acetabular cup in the acetabulum of the patient.

According to another aspect of the present disclosure, a system for determining a position of a hip prosthesis in an acetabulum of a patient may include one or more processors and one or more memory communicatively coupled to the one or more processors. The one or more memory may include instructions that, in response to execution by the one or more processors, cause the system to acquire a set of medical images of a hip of the patient, wherein the set of medical images includes medical images of the patient positioned in a corresponding functional position; determine pelvic tilt measurements of a pelvis of the patient based on the set of medical images, wherein each pelvic tilt measurement is indicative of a range of motion of the hip of the patient when the hip is placed in a corresponding functional position; determine a type and size of a femoral prosthesis and an acetabular cup of the hip prosthesis; determine a safe zone boundary that defines a set of orientations of the acetabular cup, relative to the acetabulum of the patient shown in the set of medical images, that do not result in edge loading of the acetabular cup by the femoral prosthesis based on a first mathematical model of contact points between a femoral head of the femoral prosthesis and a cup liner of the acetabular cup for each of the functional positions of the patient using the type and size of the femoral prosthesis and the acetabular cup and the pelvic tilt measurements as inputs to the first mathematical model; and display a graph of the safe zone boundary on a display.

According to a further aspect of the present disclosure, a method for determining a position of a hip prosthesis in an acetabulum of a patient may include acquiring, by a computer system, a set of medical images of a hip of the patient, wherein the set of medical images includes medical images of the patient positioned in a corresponding functional position; determining, by the computer system, pelvic tilt measurements of a pelvis of the patient based on the set of medical images, wherein each pelvic tilt measurement is indicative of a range of motion of the hip of the patient when the hip is placed in a corresponding functional position; determining, by the computer system, a type and size of a femoral prosthesis and an acetabular cup of the hip prosthesis; determining, by the computer system, a safe zone boundary that defines a set of orientations of the acetabular cup, relative to the acetabulum of the patient shown in the set of medical images, that do not result in edge loading of the acetabular cup by the femoral prosthesis based on a first mathematical model of contact points between a femoral head of the femoral prosthesis and a cup liner of the acetabular cup for each of the functional positions of the patient using the type and size of the femoral prosthesis and the acetabular cup and the pelvic tilt measurements as inputs to the first mathematical model; and determining, by the computer system, the safe zone boundary on a display of the computer system.

According to yet a further aspect of the present disclosure, one or more non-transitory, machine-readable storage media comprising a plurality of instructions stored thereon that, in response to execution, cause a computer system to acquire a set of medical images of a hip of the patient, wherein the set of medical images includes medical images of the patient positioned in a corresponding functional position; determine pelvic tilt measurements of a pelvis of the patient based on the set of medical images, wherein each pelvic tilt measurement is indicative of a range of motion of the hip of the patient when the hip is placed in a corresponding functional position; determine a type and size of a femoral prosthesis and an acetabular cup of the hip prosthesis; determine a safe zone boundary that defines a set of orientations of the acetabular cup, relative to the acetabulum of the patient shown in the set of medical images, that do not result in edge loading of the acetabular cup by the femoral prosthesis based on a first mathematical model of contact points between a femoral head of the femoral prosthesis and a cup liner of the acetabular cup for each of the functional positions of the patient using the type and size of the femoral prosthesis and the acetabular cup and the pelvic tilt measurements as inputs to the first mathematical model; and display a graph of the safe zone boundary on a display.

According to another aspect of the present disclosure, a system for determining a position of a hip prosthesis in an acetabulum of a patient may include one or more processors and one or more memory communicatively coupled to the one or more processors. The one or more memory may include instructions that, in response to execution by the one or more processors, cause the system to determine pelvic tilt measurements of a hip of the patient based on a set of medical images of the hip, wherein each pelvic tilt measurement is indicative of a range of motion of the hip of the patient when the hip is placed in a corresponding functional position; determine a type and size of a femoral prosthesis and an acetabular cup of the hip prosthesis; determine a safe zone boundary that defines a set of orientations of an acetabular cup of the hip prosthesis, relative to the acetabulum of the patient shown in the set of medical images, that do not result in edge loading of the acetabular cup by the femoral prosthesis based on a first mathematical model of contact points between a femoral head of the femoral prosthesis and a cup liner of the acetabular cup for each of the functional positions of the patient using the type and size of the femoral prosthesis and the acetabular cup and the pelvic tilt measurements as inputs to the first mathematical model; display a graph of the safe zone boundary on a display; determine, intra-operatively during the performance of an orthopaedic surgical procedure on the hip of the patient, a present orientation of the acetabular cup relative to the acetabulum of the patient; and display indicia of the present orientation on the graph of the safe zone boundary on the display.

According to a further aspect of the present disclosure, a method for determining a position of a hip prosthesis in an acetabulum of a patient may include determining, by a computer system, pelvic tilt measurements of a hip of the patient based on a set of medical images of the hip, wherein each pelvic tilt measurement is indicative of a range of motion of the hip of the patient when the hip is placed in a corresponding functional position; determining, by the computer system, a type and size of a femoral prosthesis and an acetabular cup of the hip prosthesis; determining, by the computer system, a safe zone boundary that defines a set of orientations of an acetabular cup of the hip prosthesis, relative to the acetabulum of the patient shown in the set of medical images, that do not result in edge loading of the acetabular cup by the femoral prosthesis based on a first mathematical model of contact points between a femoral head of the femoral prosthesis and a cup liner of the acetabular cup for each of the functional positions of the patient using the type and size of the femoral prosthesis and the acetabular cup and the pelvic tilt measurements as inputs to the first mathematical model; displaying, by the computer system, a graph of the safe zone boundary on a display of the computer system; determining, by the computer system and intra-operatively during the performance of an orthopaedic surgical procedure on the hip of the patient, a present orientation of the acetabular cup relative to the acetabulum of the patient; and displaying, by the computer system, indicia of the present orientation on the graph of the safe zone boundary on the display.

According to yet a further aspect of the present disclosure, one or more non-transitory, machine-readable storage media comprising a plurality of instructions stored thereon that, in response to execution, cause a computer system to determine pelvic tilt measurements of a hip of the patient based on a set of medical images of the hip, wherein each pelvic tilt measurement is indicative of a range of motion of the hip of the patient when the hip is placed in a corresponding functional position; determine a type and size of a femoral prosthesis and an acetabular cup of the hip prosthesis; determine a safe zone boundary that defines a set of orientations of an acetabular cup of the hip prosthesis, relative to the acetabulum of the patient shown in the set of medical images, that do not result in edge loading of the acetabular cup by the femoral prosthesis based on a first mathematical model of contact points between a femoral head of the femoral prosthesis and a cup liner of the acetabular cup for each of the functional positions of the patient using the type and size of the femoral prosthesis and the acetabular cup and the pelvic tilt measurements as inputs to the first mathematical model; display a graph of the safe zone boundary on a display; determine, intra-operatively during the performance of an orthopaedic surgical procedure on the hip of the patient, a present orientation of the acetabular cup relative to the acetabulum of the patient; and display indicia of the present orientation on the graph of the safe zone boundary on the display.

According to a yet another aspect of the present disclosure, a method of performing an orthopaedic surgical procedure on a hip of a patient to implant a hip prosthesis having a femoral prosthesis and an acetabular cup may include operating, pre-operatively to the orthopaedic surgical procedure, a computer system to (i) determine a safe zone boundary that defines a set of orientations of an acetabular cup, relative to an acetabulum of the patient, that do not result in edge loading of the acetabular cup by the femoral prosthesis based on a first mathematical model of contact points between a femoral head of the femoral prosthesis and a cup liner of the acetabular cup for each functional position of set of functional positions of the patient using a type and a size of the femoral prosthesis and the acetabular cup and pelvic tilt measurements of the hip of the patient as inputs to the first mathematical model and (ii) display a graph of the safe zone boundary on a display;

selecting, pre-operatively, an orientation for the acetabular cup relative to the acetabulum of the patient based on the graph of the safe zone boundary displayed on the display; and performing the orthopaedic surgical procedure on the hip of a patient using the selected orientation for the acetabular cup to implant the acetabular cup in the acetabulum of the patient.

BRIEF DESCRIPTION OF THE DRAWINGS

The detailed description particularly refers to the following figures, in which:

FIGS. 6A-6D are flow chart diagrams of a method for determining a positioning of the hip prosthesis of FIG. 1 in a bone of a patient, which may be executed by the computer system of FIG. 4 or 5;

FIG. 7 is a flow chart diagram of an embodiment of a method for determining one or more sets of contact points between the femoral prosthesis and the acetabular cup of the hip prosthesis of FIG. 1, which may be executed during the performance of the method of FIGS. 6A-6D;

FIGS. 8A-8B is a flow chart diagram of another embodiment of a method for determining one or more sets of contact points between the femoral prosthesis and the acetabular cup of the hip prosthesis of FIG. 1 based on the determination of a mathematical model, which may be executed during the performance of the method of FIGS. 6A-6D;

FIGS. 9A-9B is a flow chart diagram of a method for intra-operatively monitoring the positioning of the hip prosthesis of FIG. 1 during the performance of an orthopaedic surgical procedure to implant the hip prosthesis into a bone of the patient;

FIGS. 21A-21C are flow chart diagrams of another embodiment of a method for determining a positioning of the hip prosthesis of FIG. 1 in a bone of a patient, which may be executed by the computer system of FIG. 4 or 5;

FIGS. 22A-22B are flow chart diagrams of an embodiment of a method for generating a mathematical model indicative of loading on the acetabular cup at particular patient functional positions using a stationary mechanics model;

FIG. 23 is a flow chart diagram of an embodiment of a method for determining a safe zone boundary of acetabular cup orientations using the mathematical model generated by the method of FIGS. 22A-22B;

FIGS. 26A-26B are a flow chart diagram of another embodiment of a method for intra-operatively monitoring the positioning of the hip prosthesis of FIG. 1 during the performance of an orthopaedic surgical procedure to implant the hip prosthesis into a bone of the patient;

DETAILED DESCRIPTION OF THE DRAWINGS

Figure 1:
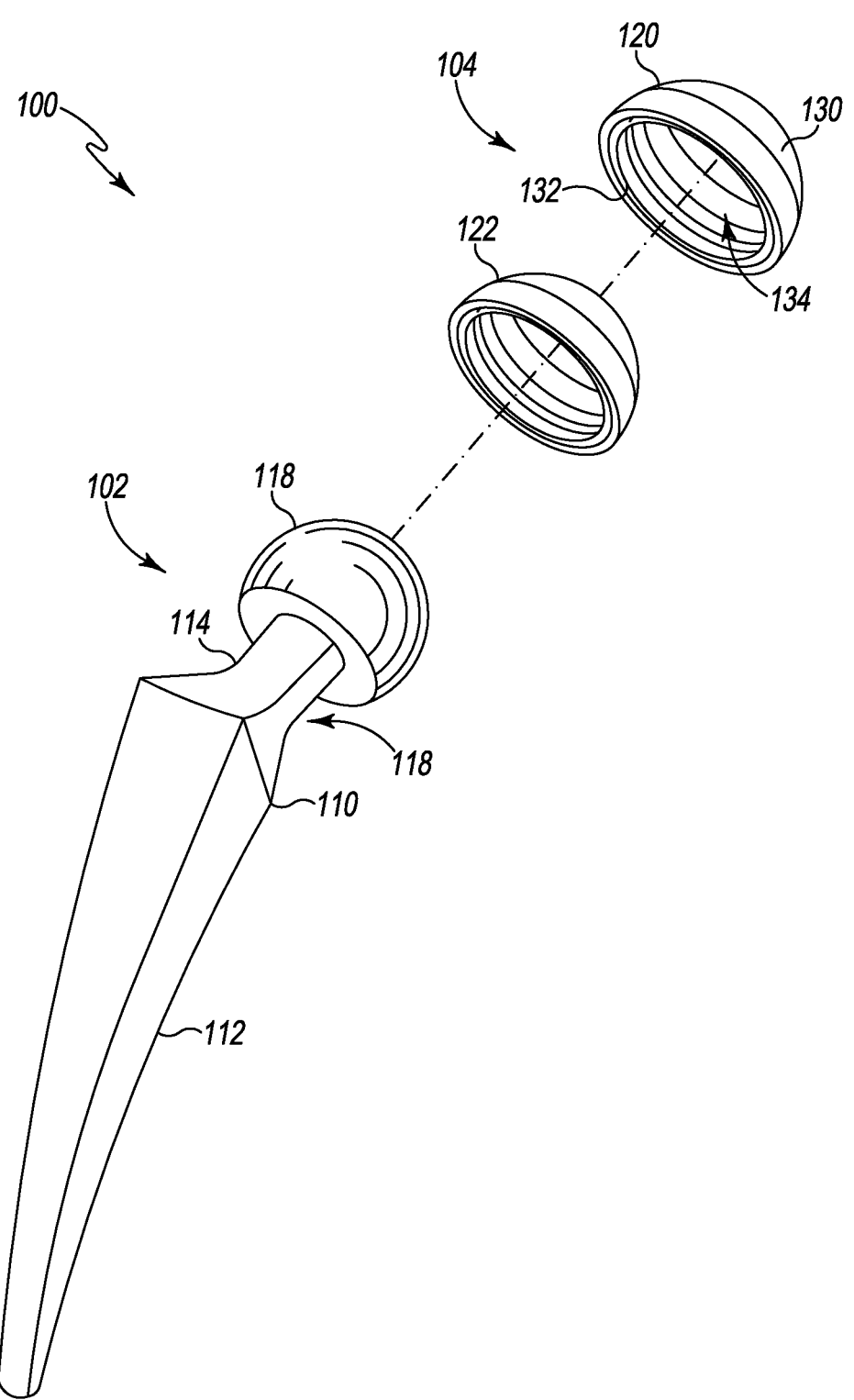
FIG. 1 is an exploded, perspective view of an embodiment of a hip prosthesis including a femoral prosthesis and an acetabular cup.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative hip orthopaedic prosthesis 100 includes a femoral prosthesis 102 and an acetabular cup 104. In use, as discussed in more detail below, the hip orthopaedic prosthesis 100 is configured to replace a natural hip joint of the patient. To do so, the femoral prosthesis 102 is configured to be implanted in the proximal end of a surgically-prepared femur of a patient, and the acetabular cup 104 is configured to be implanted into a surgically-prepared acetabulum of the patient's pelvis. Once so implanted, the femoral prosthesis 102 is supported by the acetabular cup 104, and the femoral prosthesis 102 and the acetabular cup 104 cooperate to form a prosthetic hip joint for the patient.

The illustrative femoral prosthesis 102 includes a stem 110 having an elongated distal end 112 and a neck 114 located at a proximal end 116. The elongated distal end 112 is sized and shaped to be implanted into a medullary canal of the patient's femur to secure the femoral prosthesis 102 thereto. The femoral prosthesis 102 also includes a femoral head 118 secured to the neck 114 of the stem 110. The femoral head 118 is substantially spherical in shape and is configured to be received in the acetabular cup 104 to form an artificial ball-and-socket joint of the patient's hip. The stem 110 and the femoral head 118 may be separately formed from implant-grade metallic materials such as, for example, cobalt chromium. In some embodiments, the stem 110 may also include an outer coating, such as a Porocoat® outer coating, that facilitates bone ingrowth to permit the patient's bone to affix biologically to the stem 110 after implantation.

The acetabular cup 104 includes an acetabular shell 120 and an acetabular cup liner 122 configured to be received in the acetabular shell 120. The acetabular shell 120 has a generally hemispherical shape and includes a convex outer wall 130 and a concave inner wall 132 opposite the convex outer wall 130. The inner wall 132 defines a hemispherical recess 134 that is shaped and sized to receive the acetabular cup liner 122 to form the assembled acetabular cup 104.

The acetabular shell 120 may be formed from any suitable implant-grade metallic material such as, for example, cobalt chromium. Similar to the stem 110 of the femoral prosthesis 102, the outer wall 130 of the acetabular shell 120 may include an outer coating, such as a Porocoat® outer coating, that facilitates bone ingrowth to permit the patient's bone to affix biologically to the acetabular shell 120 after implantation. As discussed above, the acetabular cup liner 122 is configured to be received in the hemispherical recess 134 of the acetabular shell 120 and is illustratively formed from a polymeric material such as, for example, polyethylene. Of course, in other embodiments, the acetabular cup liner 122 may be formed from other materials, such as a ceramic material or the like.

Figure 2:
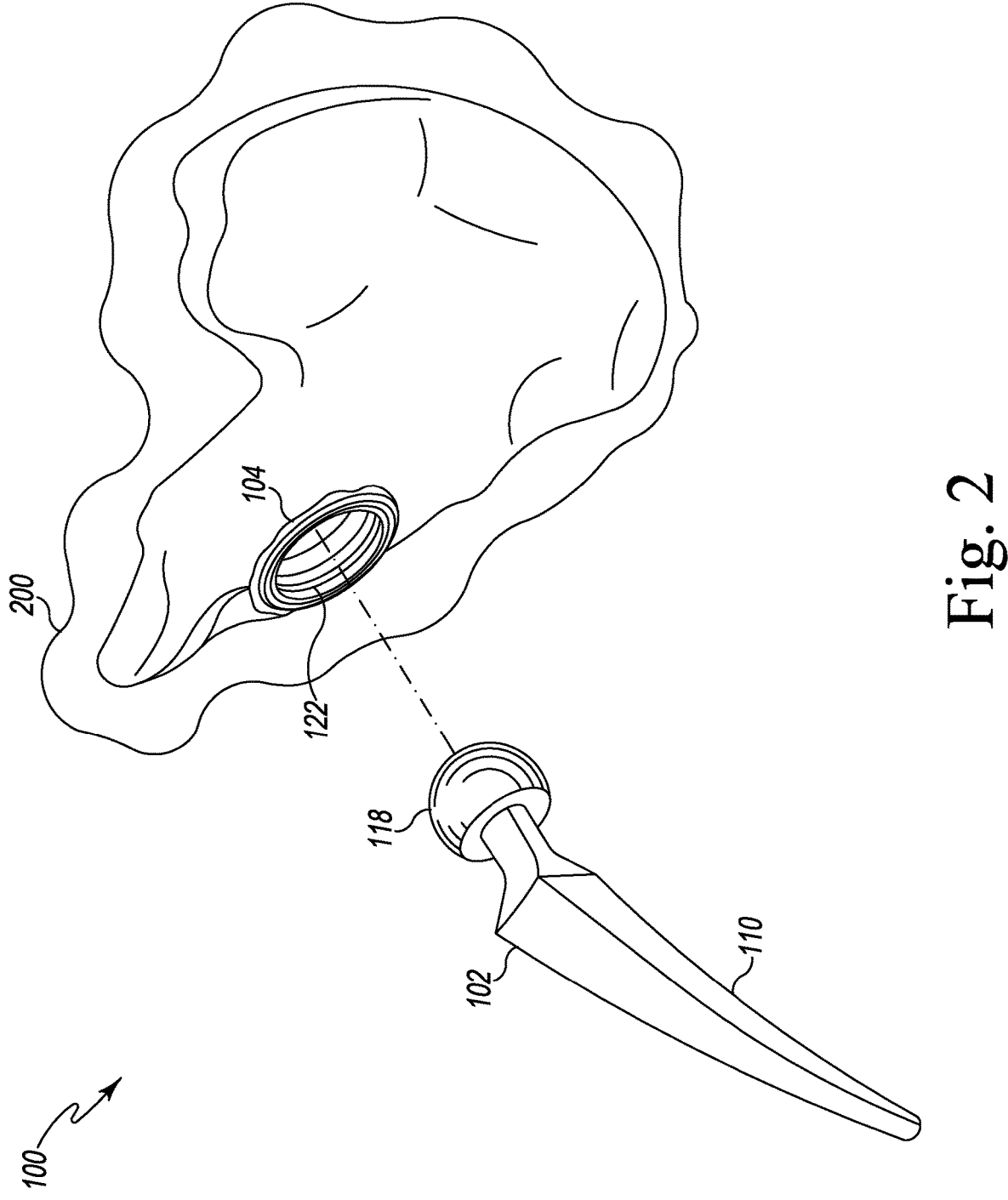
FIG. 2 is another perspective view of the hip prosthesis of FIG. 1 having the acetabular cup implanted into an acetabulum of a patient.

As shown in FIG. 2, during performance of the orthopaedic surgical procedure, an orthopaedic surgeon implants the acetabular cup 104 into an acetabulum 200 of the patient to replace the patient's natural "socket" of the patient's corresponding hip joint. In doing so, the orthopaedic surgeon may prepare the patent's acetabulum 200 (e.g., by reaming the acetabulum) and implant the acetabular shell 120 of the acetabular cup 104 into the surgically-prepared acetabulum 200 based on a pre-operative or intra-operative plan as discussed in more detail below. In doing so, the outer wall 130 of the acetabular shell 120 contacts or confronts the prepared bone of the patient's acetabulum 200. The orthopaedic surgeon may then insert the acetabular cup liner 122 into the hemispherical recess 134 of the acetabular shell 120 to form the implanted, assembled acetabular cup 104.

The orthopaedic surgeon also prepares the proximal end of the patient's femur (not shown) for implantation of the femoral prosthesis 102. Such surgical preparation may include resecting a portion of proximal end of the patient's femur (e.g., removing the natural femoral head of the patient's femur) and preparing the medullary canal of the patient's femur to receive the stem 110 of the femoral prosthesis 102.

Figure 3:
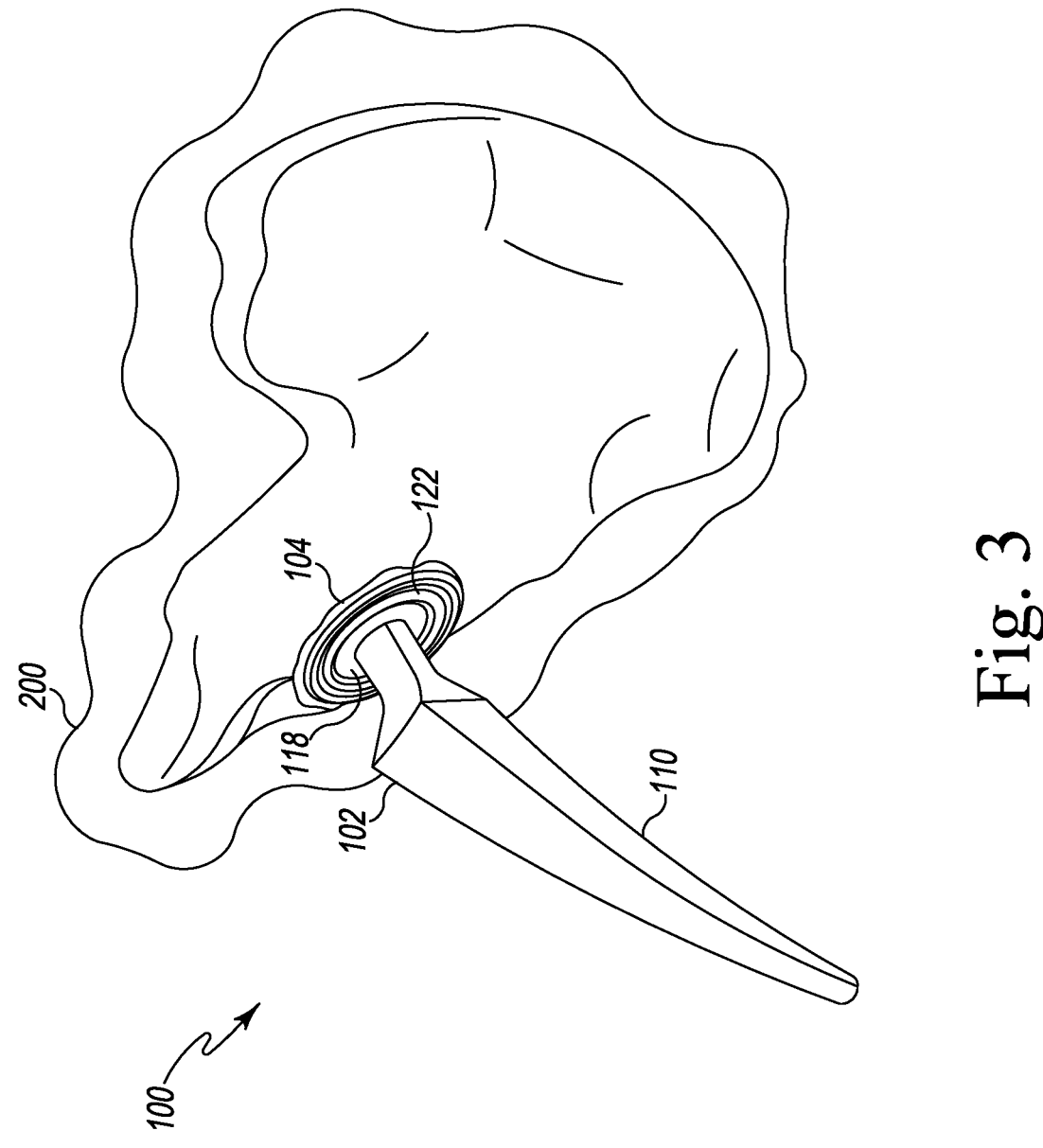
FIG. 3 is another perspective view of the hip prosthesis of FIG. 2 showing the femoral prosthesis engaged with the acetabular cup.

After the femoral prosthesis 102 and the acetabular cup 104 have been implanted into the corresponding bony anatomy of the patient, the orthopaedic surgeon may insert the femoral head 118 of the femoral prosthesis 102 into the acetabular cup liner 122 as shown in FIG. 3. In this way, the femoral prosthesis 102 and the acetabular cup 104 form a prosthetic hip joint for the patent. However, the functionally of the hip prosthesis 100 is dependent, at least in part, on the proper positioning of the acetabular cup 104 into the patient's acetabulum 200. That is, the orientation of the acetabular cup 104 relative to the patient's acetabulum 200 (i.e., the degree of anteversion and inclination) impacts the performance the hip prosthesis 100. For example, if the orientation of the acetabular cup 104 relative to the patient's acetabulum 200 is not properly chosen and subsequently achieved, the femoral prosthesis 102 may exhibit an amount of edge loading on the acetabular cup liner 122 of the acetabular cup 104. Such edge loading of the acetabular cup 104 can result in dislocation of the femoral prosthesis 102 from the acetabular cup 104 during normal activities of the patient. Accordingly, determination of a suitable orientation of the acetabular cup 104 having reduced or minimal edge loading of the acetabular cup liner 122 may improve the performance of the hip prosthesis 100 and reduce the likelihood of dislocation of the femoral prosthesis 102 from the acetabular cup 104.

Figure 4:
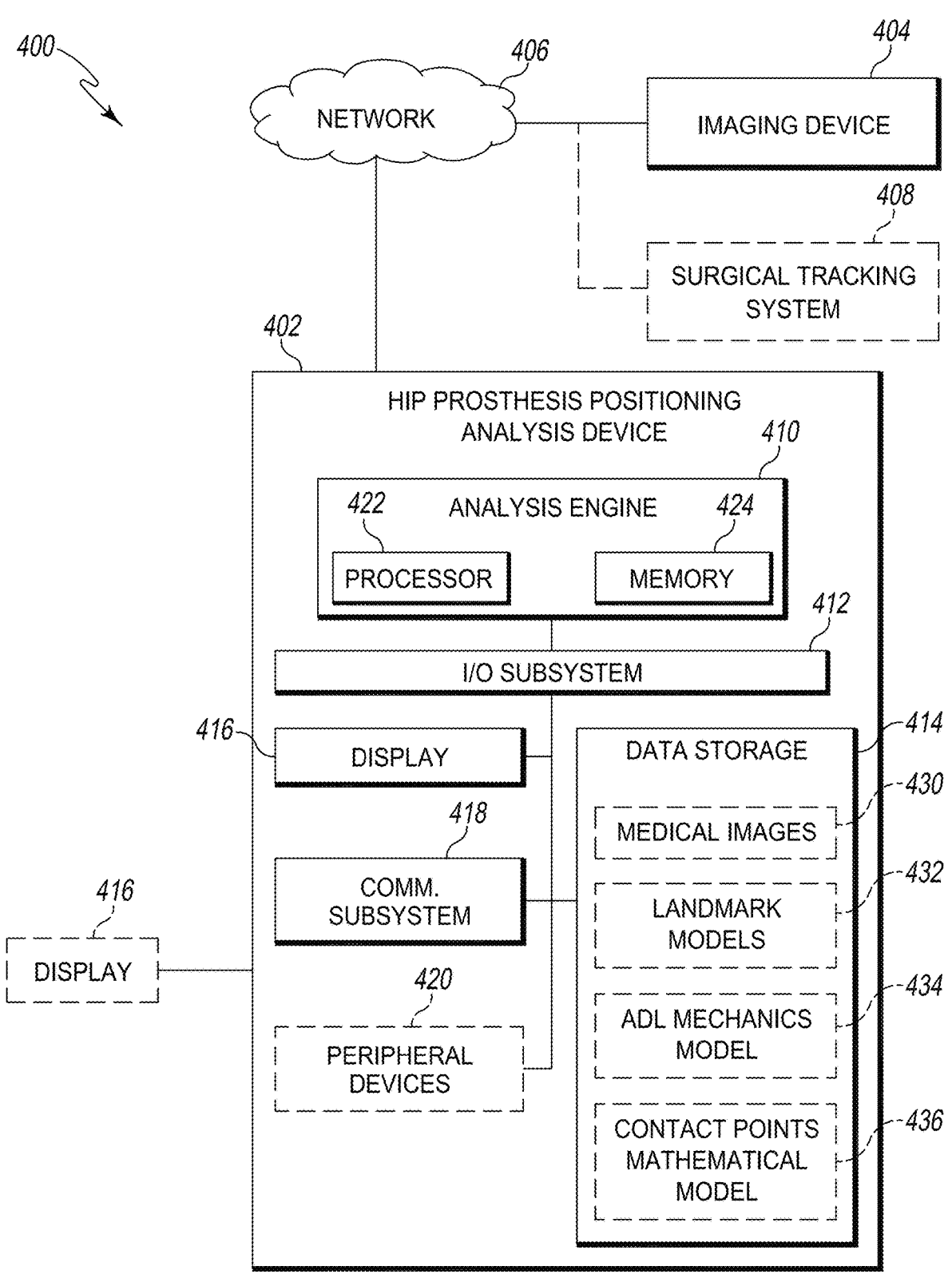
FIG. 4 is a block diagram of an embodiment of a computer system for determining a positioning of the hip prosthesis of FIG. 1 in a bone of a patient.

Referring now to FIG. 4, an illustrative computer system 400 for determining the positioning of a hip prosthesis, such as the hip prosthesis 100, includes a hip prosthesis positioning analysis device 402 and an imaging device 404 communicatively coupled to the analysis device 402 over a network 406. In use, as discussed in more detail below, an orthopedic surgeon may operate the analysis device 402 to determine, pre-operatively and/or intra-operatively, a planned or present orientation of the acetabular cup 104 relative to the patient's acetabulum 200. The orthopaedic surgeon may select or otherwise determine the planned/ present orientation based on graphical indications of predicted contact points between the femoral prosthesis 102 and the acetabular cup 104 when the patient performs particular activities-of-daily living (ADL), such as walking, stepping down, and a sit-to-stand motion. As discussed below, those graphical contact indicators may be determined based on a mechanical analysis of the patient's hip joint using a one or more models.

To do so, as discussed in more detail below, the analysis device 402 is configured to acquire or otherwise receive medical images of the patient's hip joint on which the orthopaedic surgery is to be performed from the imaging device 404 and determine pelvic tilt measurements of the patient's hip based on those medical images (e.g., via annotations from the orthopaedic surgeon or via machine learning techniques). Each pelvic tilt measurement is indicative of a range of motion of the patient's hip joint when the hip is placed in one of several corresponding functional positions (e.g., standing, seated, extended, etc.). The analysis device 402 determines or predicts one or more sets of contact points between the femoral head 118 of the femoral prosthesis 102 and the cup liner 122 of the acetabular cup 104 using an ADL mechanics model with the pelvic tilt measurements, the type and size of the hip prosthesis 100, and an orientation(s) of the acetabular cup 104 relative to the patient's acetabulum 200 as inputs to the ADL mechanics model. The ADL mechanics model is embodied as a patient-generic model, developed from the contact point data resulting from the analysis of a pool of test subjects and is indicative of the mechanical motion of a patient-generic (e.g., non-patient-specific or "averaged") hip that is exhibited during the performance of the activities-of-daily-living. It should be appreciated, as discussed in more detail below, the ADL mechanics model may also be indicative of other aspects of the hip joint, such as joint force, location of contact, and so forth.

After the set(s) of contact points have been generated, the analysis device 402 generates a contact plot for each set of contact points or a sub-set of the sets of contact points. For example, in some embodiments, the analysis device 402 may determine those sets of contact points that result in edge loading of the cup liner 122 based on the location of one or more contact points of the corresponding set of contact points relative to an edge of the cup liner 122 and only generate and/or show the corresponding contact plot for those sets of contact points that do not result in edge loading of the cup liner 122.

In some embodiments, the analysis device 402 may use the resultant set(s) of contact points of the ADL mechanics model to directly determine the corresponding contact plot. However, in other embodiments, the analysis device 402 is configured to compute a global pool of sets of contact points using the ADL mechanics model with a range of pelvic tilt values (i.e., not the pelvic tilt measurements of the specific patient), and a range of orientations of the acetabular cup 104 as inputs to the ADL mechanics model. The analysis device 402 may then use the resultant pool of sets of contact points as a data set to train or generate a mathematical model, such as linear response model, a surface model, a neural network, statistical fitting model, or other mathematical model, configured to model the pool of sets of contact points. In such cases, the developed mathematical model may then be used to generate sets of contact points using the patient's tilt measurements as input, along with a range of orientations of the acetabular cup 104, which can then be used to generate corresponding contact plots. Once so generated, the mathematical model increases the speed at which new sets of contact points are determined based on the patient title measurements and type and size of the femoral prosthesis 102 and the acetabular cup 104, which facilitates the use of the mathematical model intra-operatively wherein the speed of the calculation can be an important consideration in the orthopaedic surgical procedure as discussed in more detail below. For example, the mathematical model may be configured to produce the sets of contact points in a time period that is shorter than the time period required by the ADL mechanics model to produce the corresponding set of contact points. For example, mathematical model may produce the resultant set of contact points in less than five minutes, in less than three minutes, in less than one minute, in less than thirty seconds, in less than one second, and/or in less than one millisecond in some embodiments. As such, once the mathematical model is generated, the ADL mechanics model may not be needed to generate the set(s) of contact points going forward.

Regardless, each contact plot includes a contact indicator (e.g., a circle or dot) for each contact point in the corresponding set of contact points. As discussed in more detail below, each contact indicator includes an area that corresponds to the contact "patch" between the femoral head 118 and the cup liner 122 and, therefore, the combined areas of the set of contact indicators provides a composite contact area for the femoral head 118 and the cup liner 122. In this way, the contact plots provide a visualization to the orthopaedic surgeon of the set of contact points between the femoral head 118 and the cup liner 122 such that the surgeon may determine which set of contact points (and, therefore, which corresponding orientation of the acetabular cup 104) is most desirable based on the location, shape, and/or grouping of the associated, predicted contact points.

The hip prosthesis positioning analysis device 402 may be embodied as any type of computer or computation device capable of performing the functions described herein. For example, the analysis device 402 may be embodied as a desktop computer, a surgical navigation computer, a laptop computer, a tablet computer, a smartphone, a mobile computer, a smart device, a wearable computer system, or other computer or computer device. As shown in FIG. 4, the illustrative analysis device 402 includes an analysis engine 410, an input/output ("I/O") subsystem 412, a data storage 414, a display 416, a communication system 418 and, in some embodiments, one or more peripheral devices 420. Of course, the analysis device 402 may include additional or other components, such as those commonly found in a typical computer device, in other embodiments. Additionally, in some embodiments, one or more of the illustrative components may be incorporated in, or otherwise form a portion of, another component.

The analysis engine 410 may be embodied as any type of controller, functional block, digital logic, or other component, device, circuitry, or collection thereof capable of performing the functions described herein. In illustrative embodiment, the analysis engine 410 includes a processor 422 and a memory 424. The processor 422 may be embodied as any type of processor capable of performing the functions described herein. For example, the processor 422 may be embodied as a single or multi-core processor(s), digital signal processor, microcontroller, or other processor or processing/controlling circuit. Similarly, the memory 424 may be embodied as any type of volatile and/or non-volatile memory or data storage capable of performing the functions described herein. In operation, the memory 424 may store various data and software used during operation of the analysis device 402 such as operating systems, applications, executable software, programs, libraries, and drivers, which may be executed or otherwise used by the processor 422.

The analysis engine 410 is communicatively coupled to other components of the analysis device 402 via the I/O subsystem 412, which may be embodied as circuitry and/or components to facilitate input/output operations between the analysis engine 410 (e.g., the processor 422 and the memory 424) and the other components of the analysis device 402. For example, the I/O subsystem 412 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 412 may form a portion of a system-on-a-chip (SoC) and be incorporated, along with the analysis engine 410 (e.g., the processor 422 and the memory 424) and other components of the analysis engine 410, on a single integrated circuit chip. Additionally, in some embodiments, the memory 424, or portions of the memory 424, may be incorporated into the processor 422.

The data storage 414 may be embodied as any type of device or devices configured for short-term and/or long-term storage of data such as, for example, solid-state drives, hard disk drives, memory devices and circuits, memory cards, non-volatile flash memory, or other data storage devices. In the illustrative embodiment, the data storage 414 stores various data used by the analysis device 402 to perform the functions described herein. For example, the data storage 414 may store one or more medical images 430 of the patient. The medical images 430 may be generated by the imaging device 404 and transmitted to the analysis device 402 over the network 406 for local storage in the data storage 414. As discussed in more detail below, the medical images may be embodied as X-ray images, computed tomography (CT) images, magnetic resonance imaging (MRI) images, or other medical images of the patient's hip joint positioned in various functional positions.

The data storage 414 may also store one or more landmark models 432, which may be embodied as one or more mathematical models or algorithms (e.g., a machine learning algorithm) capable of analyzing the medical images 404 and determining associated anatomical landmarks. As discussed in more detail below, the analysis device 402 may determine the anatomical landmarks in an automated fashion using the landmark models 432 and/or determine the anatomical landmarks in a manual fashion based on annotations of the medical images received from the orthopaedic surgeon.

Additionally, the data storage 414 may store one or more ADL mechanics models 432. As discussed above and in more detail below, the ADL mechanics model(s) 432 is embodied as a mathematical model of a hip (e.g., a "patient-generic hip") that generates or predicts a set(s) of contact points between the femoral head 118 of the femoral prosthesis 102 and the cup liner 122 of the acetabular cup 104 that are produced when the hip is moved through corresponding activities-of-daily-living (e.g., walking, step down, sit-to-stand, etc.)

In some embodiments, the data storage 414 may further store a contact points mathematical model 436. As discussed above and in more detail below, the mathematical model 436 is a model of the sets of contact points between the femoral head 118 of the femoral prosthesis 102 and the cup liner 122 of the acetabular cup 104 produced by the generic ADL mechanics model 434 for a range of input variables (e.g., for a range of pelvic tilt measurements and a range of acetabular cup orientations). In this way, the mathematical model 436 may quickly generate a set of contact points for a range of orientations of the acetabular cup 104 relative to the patient's acetabulum 200 with the patient's pelvic tilt measurements as an input. In particular, the mathematical model may be configured to produce the set of contact points in a time period that is shorter than the time period required by the ADL mechanics model to produce the corresponding set of contact points.

The display 416 may be embodied as any type of display capable of displaying information to a user (e.g., the orthopaedic surgeon) of analysis device 402. For example, the display 416 may be embodied as a liquid crystal display (LCD), a light emitting diode (LED) display, an organic light emitting diode (OLED), a cathode ray tube (CRT) display, a plasma display, and/or other display device. In some embodiments, the display 416 may include a touchscreen, which may be configured to receive input from the orthopaedic surgeon based on a tactile interaction. Additionally, in some embodiments, the display 416 or a duplicate display 416 may be separate from the analysis device 402, but communicatively coupled thereto, as shown in FIG. 4 in dashed lines.

The communication subsystem 418 may be embodied as any type of communication circuit, device, or collection thereof, capable of enabling communications between the analysis device 402 and the imaging device 404 and/or other devices of the computer system 400. To do so, the communication subsystem 418 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The one or more peripheral device(s) 420 may include any number of additional peripheral or interface devices, such as other input/output devices, storage devices, and so forth. The particular devices included in the peripheral device(s) 420 may depend on, for example, the type and/or intended use of the analysis device 402.

The imaging device 404 may be embodied as any type of device or collection of devices capable of pre-operatively and/or intra-operatively generating medical images of the boney anatomy of the patient. In the illustrative embodiments, the imaging device 404 is embodied as an X-Ray imaging machine capable of generating two-dimensional medical images. However, in other embodies, the imaging device 404 may be embodied an imaging device capable of generating three-dimensional medical images, such as an MRI. In the illustrative embodiment, the imaging device 404 generates several images of the patient's hip joint while the hip joint is positioned in one of several functional positions including an anterior-posterior medical image, a sagittal-standing medical image, a seated-with-fully-flexed-hip medical image, and a sagittal-standing-with-contralateral-flexed-leg medical image. Of course, in other embodiments, the imaging device 404 may be configured to produce additional or other medical images of the patient's bony anatomy.

The network 406 may be embodied as any type of communication network capable of facilitating communication between the hip prosthesis positioning analysis device 402 and the imaging device 404 (and other components of the computer system 400). As such, the network 406 may include one or more networks, routers, switches, gateways, computers, and/or other intervening devices. For example, the network 406 may be embodied as or otherwise include one or more local or wide area networks, cellular networks, publicly available global networks (e.g., the Internet), an ad hoc network, a short-range communication network or link, or any combination thereof.

In some embodiments, the computer system 400 may also include a surgical tracking system 408. The surgical tracking system 408 may be embodied as any type of surgical tracking system, surgical navigation system, digital surgery system, or the like. For example, the surgical tracking system 408 may be embodied as a computer assisted ortho-paedic surgery (CAOS) system in some embodiments. As discussed in more detail below, the surgical tracking system 408 is configured to intra-operatively generate images of the acetabular cup 104 relative to the patient's acetabulum 200. For example, the computer system 400 may be configured to optically track markers attached to the patient's acetabulum 200 and the acetabular cup 104 to facilitate determination of the positioning (e.g., orientation) of the acetabular cup 104 relative to the patient's bony anatomy. In such embodiments, the tracking provided by the surgical tracking system 408 may replace intra-operative images produced by the imaging device 404 as discussed in more detail below.

Figure 5:
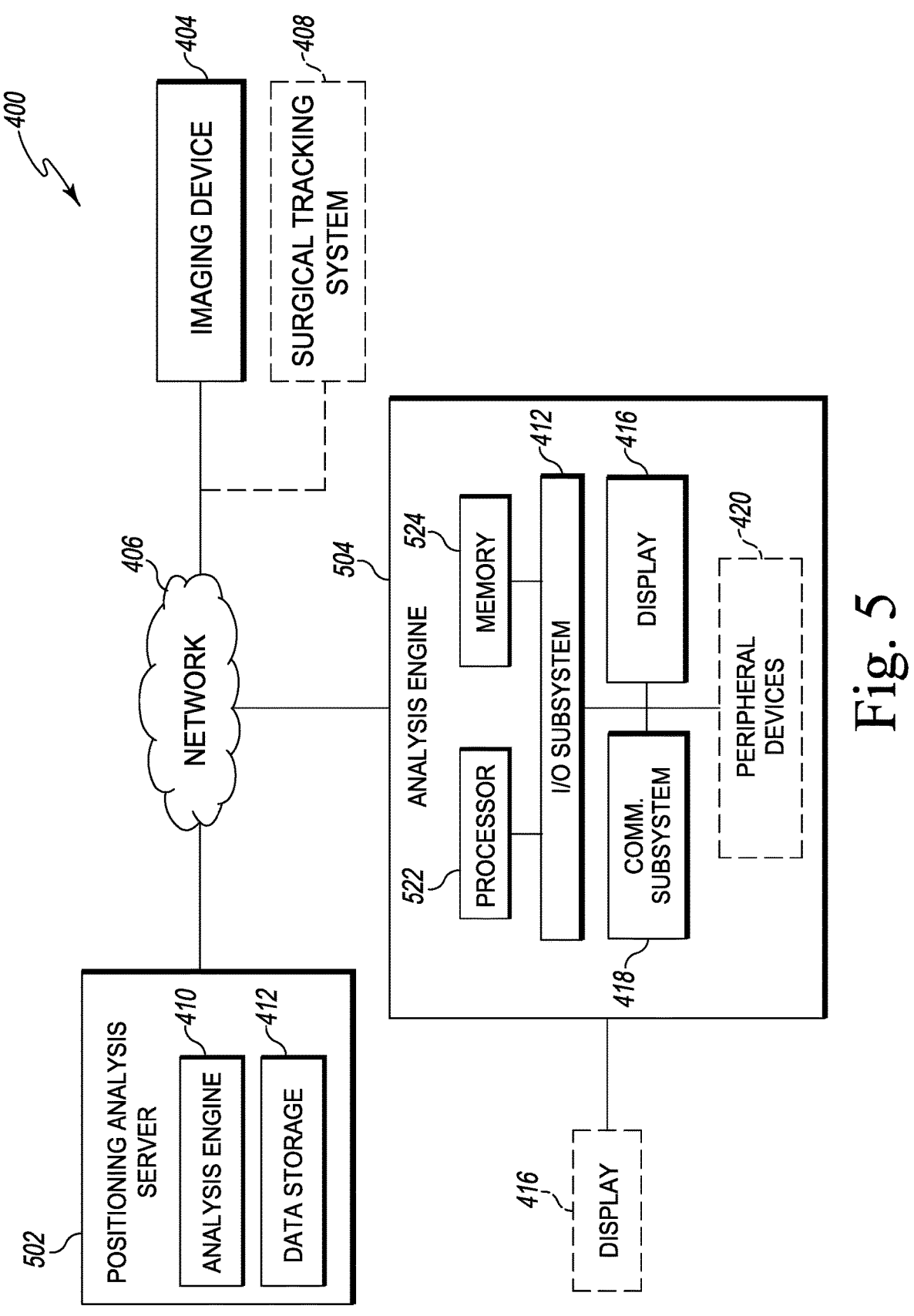
FIG. 5 is a block diagram of another embodiment of the computer system of FIG. 4.

Referring now to FIG. 5, in some embodiments the computer system 400 may implemented as a cloud-based system. In such embodiments, the computer system 400 may include a positioning analysis server 502, which is commu-nicatively coupled to a local computer device 504 via the network 406. The positioning analysis server 502 may be embodied as any type of computer or computation device capable of performing the functions described herein. For example, the positioning analysis server 502 may be embod-ied as a server, a rack-mounted computer, a network appli-ance, a desktop computer, a laptop computer, a tablet computer, or other computer or computer device.

As shown in FIG. 5, each of the analysis engine 410 and the data storage 412 is located on the positioning analysis server 502. As such, the positioning analysis server 502 is configured to perform substantially the same functions as described above and below in regard to the analysis device 402. For example, the positioning analysis server 502 is configured to acquire or otherwise receive the medical images of the patient's hip joint from the imaging device 404 and determine pelvic tilt measurements of the patient's hip based on those medical images. Additionally, the positioning analysis server 502 is configured to determine or predict one or more sets of contact points between the femoral head 118 of the femoral prosthesis 102 and the cup liner 122 of the acetabular cup 104 using the ADL mechanics model 434 (and/or the contact points mathematical model 434) and generate a contact plot for each set of contact points (or a sub-set of the sets of contact points) as discussed above. The positioning analysis server 502 may subsequently transmit the contact plots and/or sets of contact points to the local computer device 504.

The local computer device 504 may be embodied as any type of computer or computation device capable of perform-ing the functions described herein. For example, the local computer device 504 may be embodied as a desktop com-puter, a laptop computer, a tablet computer, a smartphone, a mobile computer, a smart device, a wearable computer system, or other computer or computer device. Illustratively the local computer device 504 includes a processor 522, a memory 520, the input/output ("I/O") subsystem 412, the display 416, the communication system 418 and, in some embodiments, the one or more peripheral devices 420.

The processor 522 may be similar to the processor 422 of the analysis device 402 described above and may be embod-ied as any type of processor capable of performing the functions described herein. For example, the processor 522 may be embodied as a single or multi-core processor(s), digital signal processor, microcontroller, or other processor or processing/controlling circuit. Similarly, the memory 524 may be similar to the memory 424 of the analysis device 402 described above and may be embodied as any type of volatile and/or non-volatile memory or data storage capable of performing the functions described herein. In operation, the memory 524 may store various data and software used during operation of the local computer device 504 such as operating systems, applications, executable software, pro-grams, libraries, and drivers.

Referring now to FIGS. 6A-6D, in use, the hip prosthesis positioning analysis device 402 (and/or the positioning analysis server 502 of FIG. 5) is configured to execute a method 600 for determining a positioning of the hip pros-thesis 100 in the boney anatomy of the patient. For example, the method 600, or portions thereof, may be embodied as a set of executable instructions stored on the analysis device 402 and executable by the analysis device 402. As such, it should be appreciated that the operations of the method 600 may be performed by one or more components of the analysis device 402 and/or devices communicatively coupled to the analysis device 402.

The method 600 begins with block 602 in which the analysis device 402 determines whether to analyze the positioning of the hip prosthesis 100 relative to the patient's boney anatomy (e.g., the orientation of the acetabular cup 104 relative to the patient's acetabulum 200). For example, the analysis device 402 may await instruction or input from the orthopaedic surgeon prior to begin the method 600.

If so, the method 600 advances to block 604 in which the analysis device 402 acquires or receives a set of medical images of the patient's hip joint on which the orthopaedic surgery is to be performed from the imaging device 404. The medical images are embodied as images of the patient's hip joint with the hip joint positioned in various functional positions. The analysis device 402 may receive any type and number of suitable medical images that facilitate the deter-mination of pelvic tilt measurements of the patient as discussed in more detail below. For example, as discussed above, the medical images are illustratively embodied as two-dimensional X-ray images, but may be embodied as other types of two-dimensional medical images and/or three-dimensional medical images in other embodiments.

Figure 11:
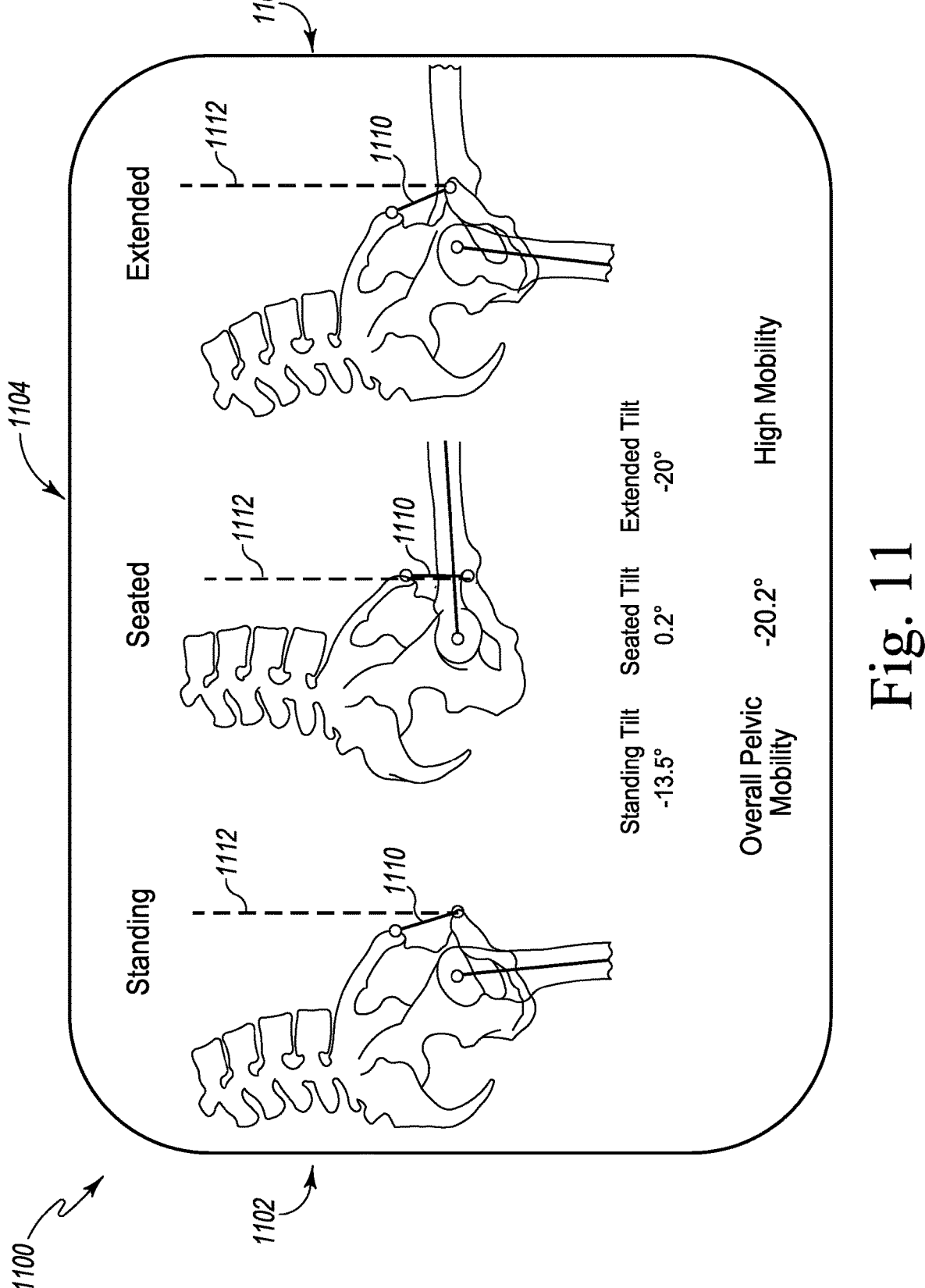
FIG. 11 is an illustrative screen image that may be displayed during the performance of the method of FIGS. 6A-6D showing medical images of the patient's hip joint and associated pelvic tilt measurements.

In the illustrative embodiment, the analysis device 402 receives four different medical images including a standing anterior-posterior medical image in block 606, a sagittal standing medical image in block 608, a sagittal seated-withfully-flexed-hip medical image in block 610 and a sagittal standing-with-contralateral-flexed-limb medical image in block 612. The anterior-posterior medical image may be embodied as a medical image of the patient's hip joint taken from a corona plane anterior to the patient while the patient is standing. Additionally, the sagittal standing medical image may be embodied as a medical image of the patient's hip joint taken from a sagittal plane of the patient while the patient is standing. An illustrative sagittal standing medical image 1102 is shown in FIG. 11. The sagittal seated-with-fully-flexed-hip medical image may be embodied as a medical image taken from a sagittal plane of the patient while the patient is in a seated position with the hip joint in full flexion (e.g., with the femur flexed about 90 degrees relative to the standing position). An illustrative sagittal seated-with-fully-flexed-hip medical image 1104 is shown in FIG. 11. And, the sagittal standing-with-contralateral-flexed-limb medical image may be embodied as a medical image taken from a sagittal plane of the patient while the patient is standing with the leg of the opposite hip joint from the hip joint on which the orthopaedic surgery is being performed positioned in flexion (e.g., with the opposite femur flexed about 90 degrees relative to the standing position). An illustrative sagittal standing-with-contralateral-flexed-limb medical image 1106 is shown in FIG. 11.

Figure 6A:
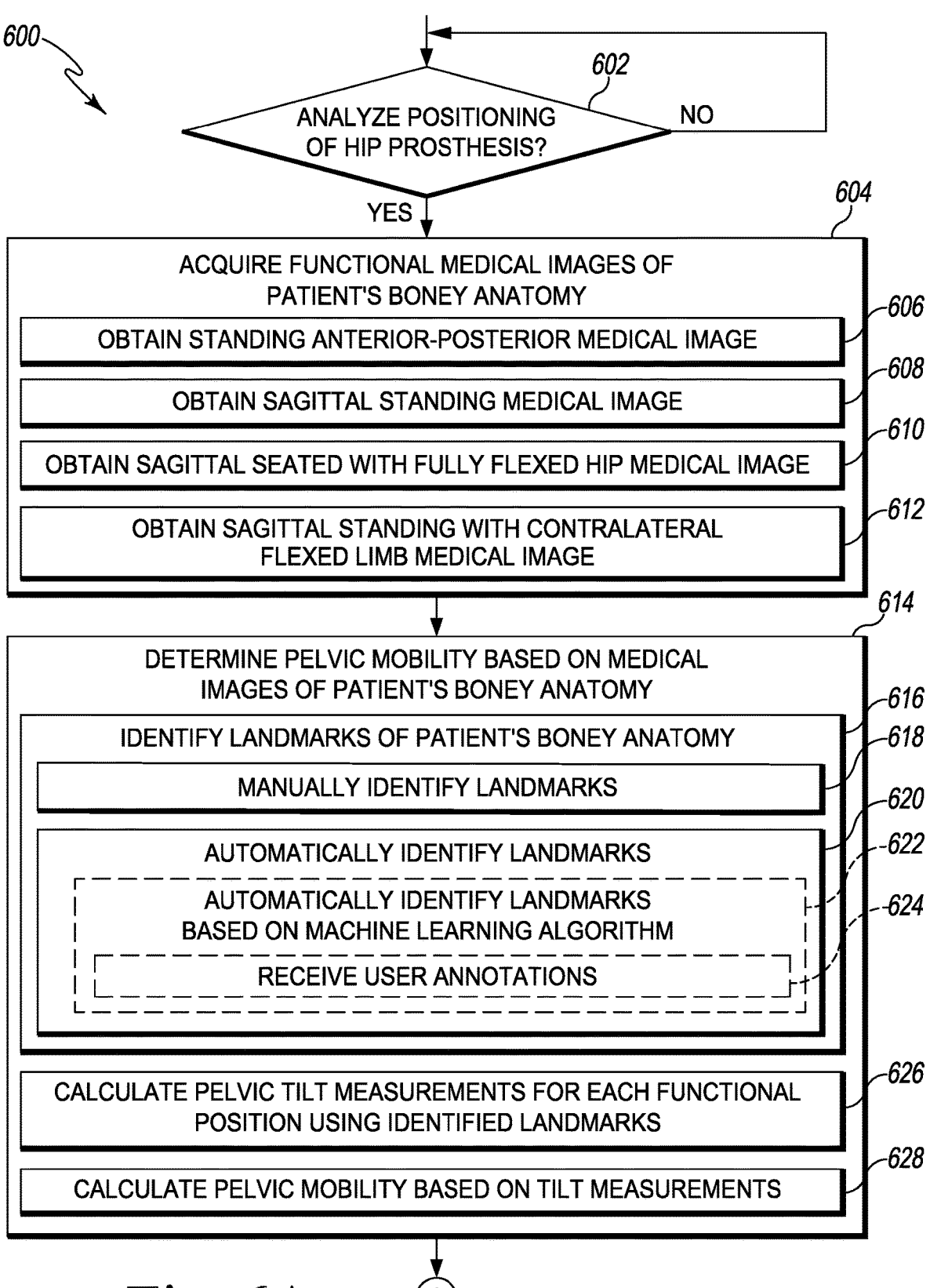

After the analysis device 402 acquires the medical images in block 604 of FIG. 6A, the analysis device 402 determines a pelvic mobility of the patient based on the received medical images in block 614. The pelvic mobility is indicative of a range of motion of the patient's pelvis and is determined based on pelvic tilt measurements of the patient. As such, the analysis device 402 initially determines the pelvic tilt measurements of the patient's hip from the medical images. To do so, in block 616, the analysis device 402 may identify particular anatomical landmarks of the patient's boney anatomy. In particular, the analysis device 402 identifies anatomical landmarks on the patient's relevant femur and acetabulum 200. The anatomical landmarks may be embodied as any anatomical landmark that facilitates or improves the determination of the pelvic tilt measurements of the patient. The particular landmarks used may depend on various factors such as the patient's bony anatomy, the size and type of hip prosthesis 100, and/or other factors. For example, in the illustrative embodiment, the identified anatomical landmarks includes the medial and lateral anterior superior iliac spine, the pubic symphysis, the center of the hip join, and the mid-point of the femoral shaft of the relevant femur.

Figure 10:
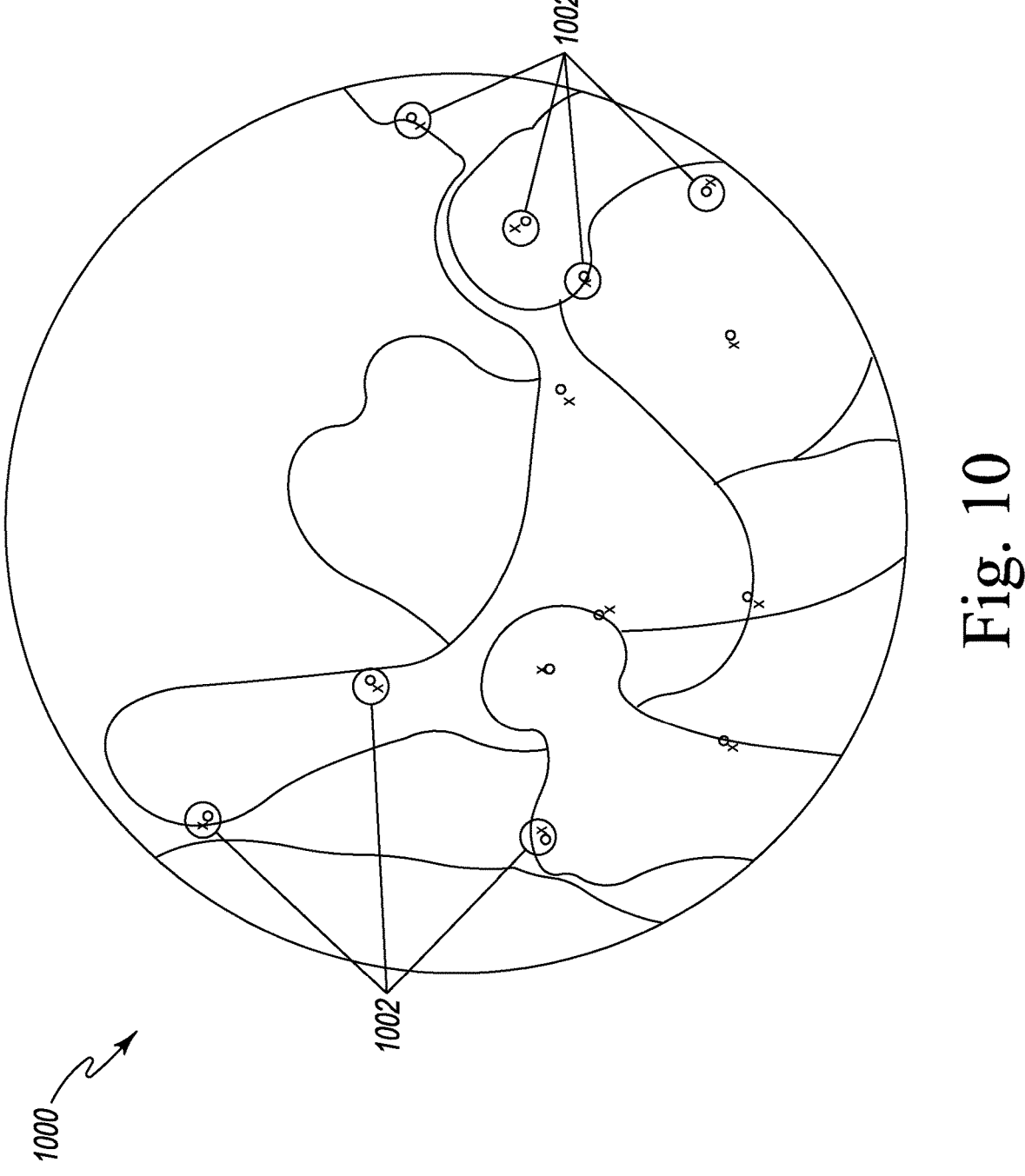
FIG. 10 is an illustrative medical image of the patient's hip joint that may be displayed during the performance of the method of FIGS. 6A-6D showing identified anatomical landmarks.

In some embodiments, the analysis device 402 may identify the relevant anatomical landmarks based on manually annotated medical images received from the orthopaedic surgeon in block 618. For example, as shown in FIG. 10, the orthopaedic surgeon may manually mark one or more medical images 1000 (e.g., one or more of the medical images received in block 604) with indicia 1002 of the anatomical landmarks, which are shown in FIG. 10 as "o". Additionally or alternatively, in other embodiments, the analysis device 402 may be configured to automatically and/or autonomously identify the anatomical landmarks on the patient's bony anatomy in the medical image(s) in block 620 of FIG. 6, which are shown in FIG. 10 as "x". As such, the autonomous identification may be in addition to or replace the manual annotations provided by the orthopaedic surgeon in block 618. For example, in some embodiments as shown in block 622, the analysis device 402 may utilize a machine-learning algorithm to identify the anatomical landmarks in the medical image(s). In such embodiments, the machine learning algorithm may undergo a training phase in block 624 in which the machine learning algorithm is supplied with a training set of manually annotated medical images of sample patients. In this way, the machine-learning algorithm is trained to identify the corresponding anatomical landmarks in new medical images such as the medical images of the present patient.

After the anatomical landmarks have been identified, in block 626, the analysis device 402 calculates the pelvic tilt measurements of the patient's hip based on the identified landmarks and using the medical images received in block 604. The pelvic tilt measurements are indicative of the size of an angle between the anterior pelvic plane (APP) of the patient relative to a vertical plane. For example, as shown in FIG. 11, the analysis device 402 may determine a standing pelvic tilt measurement based on the sagittal standing medical image 1102. The standing pelvic tilt measurement is a measurement of the angle between the patient's anterior pelvic plane 1110 and a reference vertical plane 1112 with the patient in a standing position. Additionally, the analysis device 402 may determine a seated pelvic tilt measurement based on the sagittal seated-with-fully-flexed-hip medical image 1104. The seated pelvic tilt measurement is a measurement of the angle the patient's anterior pelvic plane 1110 and the reference vertical plane 1112 with the patient in a seated position with the hip joint in full flexion. The analysis device 402 may also determine an extended pelvic tilt measurement based on the sagittal standing-with-contralateral-flexed-limb medical image 1106. The extended pelvic tilt measurement is a measurement of the angle between the patient's anterior pelvic plane 1110 and the reference vertical plane 1112 with the patient standing with the leg of the opposite hip joint positioned in flexion. Of course, in other embodiments, other methodologies, such as a method based on the spine axis of the patient, may be employed to determine the pelvic tilt of the patient's hip such that the orientation of the patient's pelvic in three-dimensional space can be understood.

Referring back to FIG. 6A, after the analysis device 402 has determined the various pelvic tilt measurements in block 626, the analysis device 402 determines the patient's pelvic mobility based on the pelvic tilt measurements in block 628. To do so, in the illustrative embodiment, the analysis device 402 is configured to subtract the extended pelvic tilt measurement from the seated pelvic title measurement. For example, as shown in FIG. 11, the patient's seated tilt measurement is 0.2 degrees and the patient's extended pelvic title measurement is −20 degrees, which results in a determined overall pelvic mobility of 20.2 degrees. Additionally, as shown in FIG. 11, the analysis device 402 may present the measured pelvic tilt measurements and the calculated pelvic mobility to the orthopaedic surgeon via a screen image 1100, which may be displayed to the surgeon on the display 416. Of course, in other embodiments, other differences or comparisons between pelvic tilt measurements may be used or considered in the determination of a pelvic mobility score for the patient and/or otherwise presented to the orthopaedic surgeon.

Referring back to FIG. 6A, after the analysis device 402 has determined the pelvic mobility of the patient's relevant hip joint, the method 600 advances to block 630 of FIG. 6B. In block 630, the analysis device 402 determines the type and size of the femoral prosthesis 102 and the acetabular cup 104 of the hip prosthesis 100 that is to be implanted into the patient. For example, the orthopaedic surgeon may select the type and size from a menu of available types and sizes or otherwise provide those selections to the analysis device 402.

In block 632, the analysis device 402 determines sets of contact points for a range of possible orientation of the acetabular cup 104 relative to the patient's acetabulum 200. As discussed previously, the contact points are the predicated location of contact between the femoral head 118 of the femoral prosthesis 102 on the cup liner 122 of the acetabular cup 104 when the patient performs particular corresponding activities-of-daily living (ADL), such as walking, stepping down, and a sit-to-stand motion. It should be appreciated that, in the illustrative embodiment, each determined "contact point" includes an area associated with it. That is, the contact points are embodied as areas or patches of contact between the femoral head 118 of the femoral prosthesis 102 on the cup liner 122 of the acetabular cup 104, rather than a single "point" of contact having no area.

In the illustrative embodiment as shown in block 634, the analysis device 402 determines the sets of contact points based on the patient-generic ADL mechanics model using the pelvic mobility determined in block 614, the pelvic tilt measurements determined in block 626, the type and size of the femoral prosthesis 102 and the acetabular cup 104, and the range of orientations of the acetabular cup 104 as inputs. It should be appreciated that, in other embodiments, additional or other types of inputs may be used.

As discussed above, the ADL mechanics model may be embodied as any type of model capable of generating data indicative of the loading (i.e., the set(s) of contact points) of the acetabular cup 104 by the femoral prosthesis 102 while the patient performs particular corresponding activities-of-daily living (ADL). For example, the ADL mechanics model may be embodied as a mathematical equation or set of equations having inputs (e.g., the pelvic tilt measurements, the type and size of the femoral prosthesis 102 and the acetabular cup 104, and the range of orientations of the acetabular cup 104) that define coefficients of the mathematical equation(s). In the illustrative embodiment, for example, the ADL mechanics model is based on the Hertzian contact model for sphere-on-sphere contact and enables calculations of contact area and contact stress between the femoral head 118 of the femoral prosthesis 102 and the cup liner 122 of the acetabular cup 104. In doing so, the ADL mechanics model may use, or otherwise rely on, several mathematical equations including:

$$a = \sqrt[3]{\frac{3F\left[\frac{1-v_1^2}{E_1} + \frac{1-v_2^2}{E_2}\right]}{4\left(\frac{1}{R_1} + \frac{1}{R_2}\right)}} \qquad \text{Equation (1)}$$

$$P_{max} = \frac{3F}{2\pi a^2} \qquad \text{Equation (2)}$$

In equation (1), the contact area, a, between the femoral head 118 of the femoral prosthesis 102 and the cup liner 122 of the acetabular cup 104 can be solved in which R1 is the radius of the "sphere" of the femoral head 118, R2 is the radius of the "sphere" of the cup liner 122, E1 is the moduli elasticity of the "sphere" of the femoral head 118, E2 is the moduli elasticity of the "sphere" of the cup liner 122, v1 and v2 are the Poisson's ratios, and F is the applied force. Similarly, in equation (2), the maximum contact pressure, Pmax, using the same variables as equation (1) defined above. It should be appreciated that modifications to equations (1) and (2) may be modified and/or other equations used in the ADL mechanics model to the loading (i.e., the set(s) of contact points) of the acetabular cup 104 by the femoral prosthesis 102.

As discussed above, the analysis device 402 may determine the sets of contact points for the present patient directly from the generic ADL mechanics model or from a contact points mathematical model that models the contact points generated by the ADL mechanics model. For example, as shown in FIG. 7, the analysis device 402 may execute a method 700 to determine the sets of contact points between the femoral prosthesis 102 and the acetabular cup 104 using the results of the ADL mechanics model directly. The method 700 begins with block 702 in which the patient-generic ADL mechanics model is updated with the pelvic mobility of the present patent as determined in block 614 and the pelvic tilt measurements as determined in block 626 of method 600. Because the pelvic mobility and the pelvic tilt measurements do not change in each iteration of the ADL mechanics model (unlike the orientation of the acetabular cup 104), the generic ADL mechanics model may be updated with those patient-specific measurements in some embodiments. Additionally, an initial orientation of the acetabular cup 104 relative to the patient's acetabulum 200 is determined in block 704. The initial orientation may be pre-set or selected by the orthopaedic surgeon.

Figure 12:
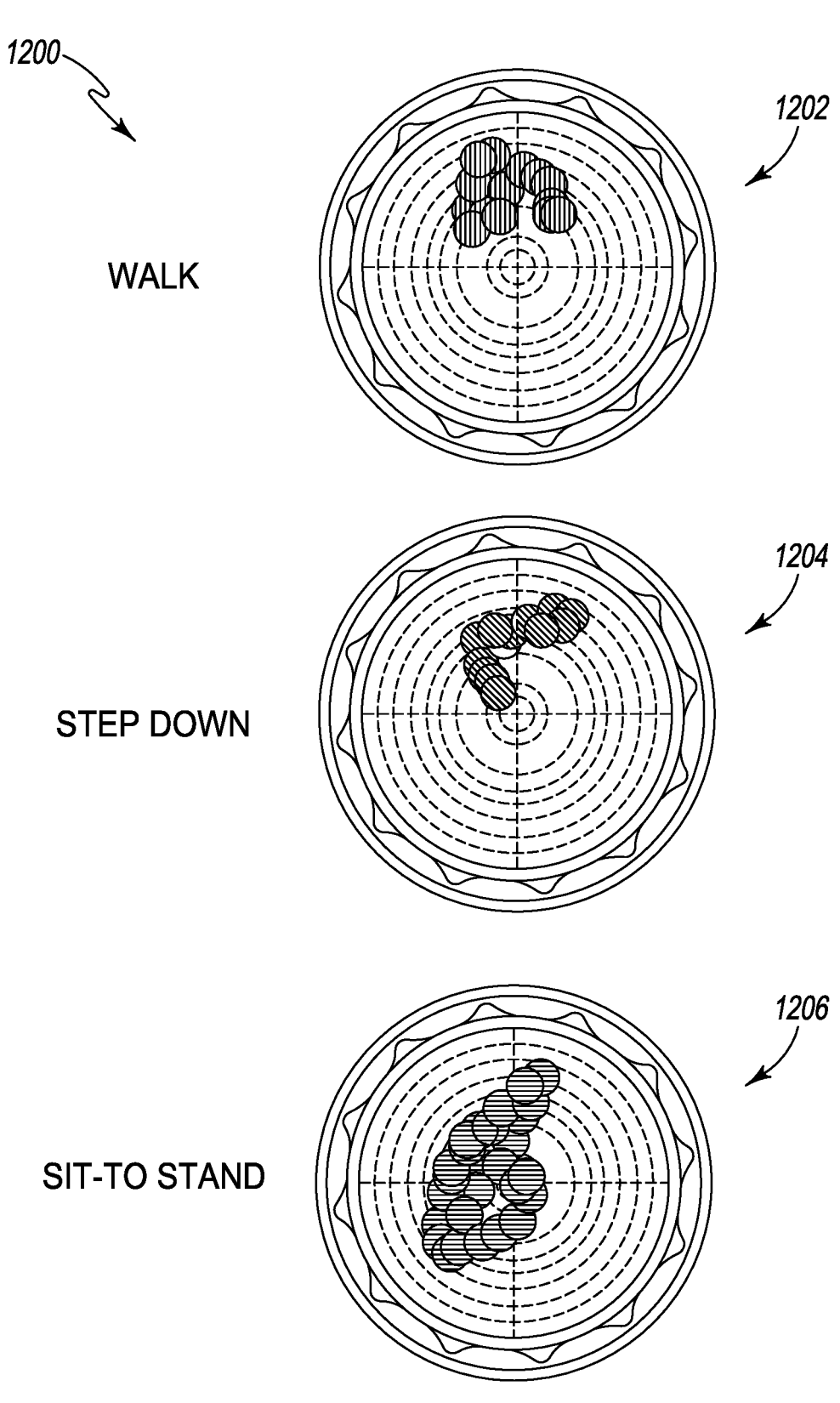
FIG. 12 is an illustrative screen image that may be displayed during the performance of the method of FIGS. 6A-6D showing contact points between the femoral prosthesis and the acetabular cup of the hip prosthesis of FIG. 1 during the performance of corresponding activities-of-daily-living (ADL)

Subsequently, in block 706, the analysis device 402 determines the set of contact points between the femoral head 118 of the femoral prosthesis 102 and the cup liner 122 of the acetabular cup 104 using the updated ADL mechanics model with the selected orientation of the acetabular cup (e.g., the initial cup orientation selected in block 704 for the first iteration of block 706) as an input to the updated ADL mechanics model. To do so, in block 708, the analysis device 402 determines a sub-set of contact points for each ADL activity. That is, for each ADL activity of interest (e.g., walking, step down, sit-to-stand motion), a separate sub-set of contact points is determined using the updated ADL mechanics model with the present orientation of the acetabular cup 104 as an input to the updated ADL mechanics model. For example, as shown in FIG. 12, a set of contact points 1200 may include a sub-set of contact points 1202 generated by the ADL mechanics model for the ADL activity of the patient walking, a sub-set of contact points 1204 generated by the ADL mechanics model for the ADL activity of the patient stepping down (e.g., stepping down a stairs), and a sub-set of contact points 1206 generated by the ADL mechanics model for the ADL activity of the patient moving from a sitting position to a standing position. Of course, it should be appreciated that additional or other ADL activities may be used in other embodiments. Furthermore, in other embodiments, the mechanics model may not be based on a prescribed range of motion of the patient's hip joint rather than a particular ADL or set of ADLs. That is, the kinematics of loading of the patient' hip joint may be used unrelated to a particular ADL. Regardless, it should be appreciated that such additional or other ADL activities and/or kinematics will modify the parameters of the ADL mechanics model based on the corresponding sample set of contact points from the pool of test subjects performing the additional or other ADL activity. It should be appreciated that although the ADL mechanics model is described in regard to FIG. 12 as separately generating the sub-sets 1202, 1204, and 1206, the ADL mechanics model may be configured to generate the sub-sets 120, 1024, 1206 as a single calculation or equation.

Furthermore, it should be appreciated that the femur and/or acetabulum 200 of the patient is in motion throughout the movement of the corresponding ADL activity. As such, the point of contact between the femoral head 118 on the acetabular liner 122 typically exhibits constant movement during the performance of the ADL activity. To provide clarity to the contact plot, the contact points are discretized such that the resulting set of contact points is sufficient to properly define the motion of the contact point throughout the ADL activity. To do so, in block 710 of FIG. 7, each ADL activity is temporally discretized and a separate contact point of the corresponding sub-set of contact points is determined for each temporal period. In this way, the ADL mechanics model is formulated to produce a contact point for each temporal period of each ADL activity. The resolution of the temporal periods may be selected based on several factors such as the ADL activities used, the set of test patients, the type of prosthesis, and/or other considerations. Of course, it should be appreciated that if the selected resolution is too low, an important movement or location of a contact point may be missed. Conversely, if the selected resolution is too high, the computation of the set of contact points may take too long to be practical. Regardless, it should be appreciated that the resolution of the temporal periods affects the development of the generic ADL mechanics model and forms an integral part of that model.

Figure 13:
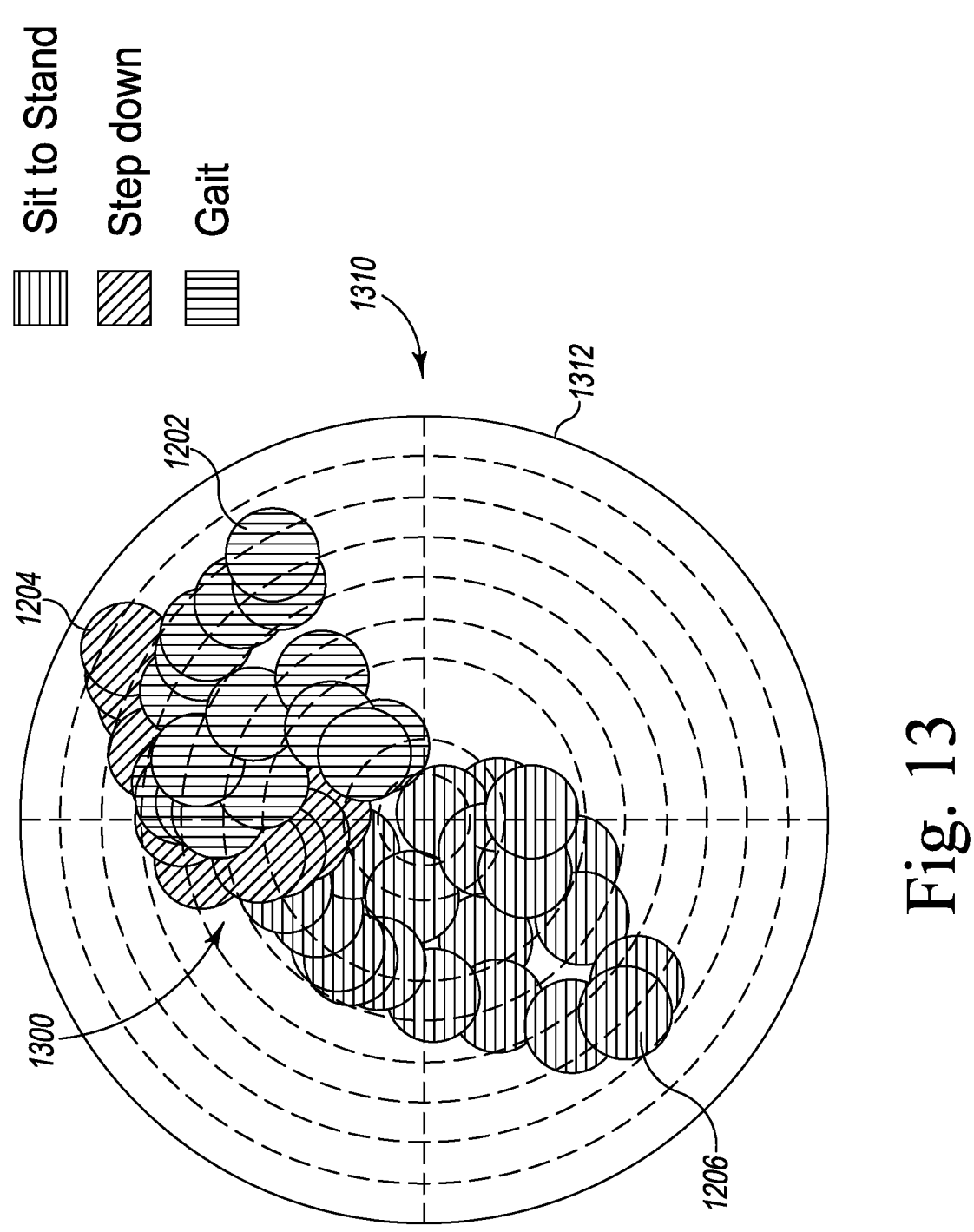
FIG. 13 is an illustrative screen image that may be displayed during the performance of the method of FIGS. 6A-6D showing a set of contact points between the femoral prosthesis and the acetabular cup of the hip prosthesis of FIG. 1 during the performance of corresponding activities-of-daily-living (ADL) and arranged on a cup liner map.

Subsequently, in block 712, the analysis device 402 generates the final set of contact points for the selected orientation of the acetabular cup 104 based on the individual sub-sets of the contact points of each ADL activity determined in block 708. To do so, the analysis device 402 may simply group the sub-sets into a single set of contact points. For example, as shown in FIG. 13, each of the sub-sets of contact points 1202, 1204, and 1206 have been grouped together to from a set of contact points 1300, which is shown in FIG. 13 as a contact plot as discussed in more detail below.

Referring again back to FIG. 7, after the set of contact points have been determined for the selected/present orientation of the acetabular cup 104, the method 700 advances to block 714 in which the analysis device 402 determines whether a set of contact points for another orientation of the acetabular cup 104 should be determined. If so, the orientation is adjusted, and the method 700 loops back to block 706 in which the analysis device 402 calculates the set of contact points between the femoral head 118 of the femoral prosthesis 102 and the cup liner 122 of the acetabular cup 104 using the updated ADL mechanics model with the new orientation of the acetabular cup 104 as an input as discussed above. The granularity at which the orientation of the acetabular cup is modified may be selected based on one or more criteria including, for example, the desired resolution of the sets of contact points, the type of hip prosthesis 100, the computation power of the analysis device 402, aspects of the patient, and/or other criteria. In the illustrative embodiment, the granularity of the acetabular cup adjustment is fixed, but may be adjustable by the orthopaedic surgeon in other embodiments.

It should be appreciated that the ADL mechanics model has been described above in regard to FIG. 7 as iteratively calculating the sets of contact points for each orientation in a range of orientations of the acetabular cup 104 relative to the patient's acetabulum 200. However, in other embodiments, the ADL mechanics model may be designed or formulated such that the sets of contact points for each cup orientation of the range of orientations of the acetabular cup 104 is determined as a single calculation or equation. That is, the various orientations may be "hard coded" into the ADL mechanics model, rather than iteratively adjusted as described above in regard to method 700.

Referring now to FIGS. 8A and 8B, in other embodiments, the analysis device 402 may determine the sets of contact points using a mathematical model that has been trained or otherwise designed to model the output of the ADL mechanics model. To do so, the analysis device 402 may execute a method 800 for determining the sets of contact points between the femoral prosthesis 102 and the acetabular cup 104 using a contact points mathematical model. As discussed in more detail below, the method 800 includes a mathematical model generation phase in block 802-838 in which a global pool of sets of contact points between the femoral prosthesis 102 and the acetabular cup 104 is determined for a range of varying inputs, such as a range of pelvic tilt values and acetabular cup orientations. In this way, a "universe" of sets of contact points is generated for a large number of combinations of inputs, and that "universe" of sets of contact points is then used generate the mathematical model. The method 800 also includes a contact point determination phase in blocks 840-842 in which the mathematical model is subsequently used to generate sets of contact points with the patient tilt measurements as inputs, as discussed in more detail below. It should be appreciated that the mathematical model generation phase of blocks 802-836 may be executed or performed some time prior to the execution of the contact point determination phase of blocks 840-842 and/or performed on separate compute devices/servers. That is, the mathematical model may be developed prior to the orthopaedic surgeon's use of the analysis device 402 to determine a suitable orientation of the hip prosthesis 100 for the particular patient. For example, the mathematical model may be developed by the provider of the analysis device 402 and/or a software package embodying the method 600.

The method 800 begins with block 802 in which the analysis device 402 determines the granularity of various inputs to the patient-generic ADL mechanics model. For example, in block 804, the granularity of the pelvic tilt values and, thereby, the granularity of the pelvic mobility values are determined. Additionally, in block 806 the granularity of the orientation of the acetabular cup 104 is determined. For example, in block 808, the granularity of the degree of inclination of the acetabular cup 104 relative to a patient's acetabulum 200 may be determined and, in block 810, the granularity of the degree of anteversion of the acetabular cup 104 relative to a patient's acetabulum 200 may be determined. The granularities of the pelvic tilt values and the acetabular cup orientation define the amount at which each of those values are adjusted per iteration of the ADL mechanics model (or otherwise different from each other in those embodiments in which the ADL model is designed to perform a single calculation rather than iterative calculations). As such, it should be appreciated that the granularity of the pelvic tilt values and the acetabular cup orientation adjusts the resolution of the output of the resulting mathematical model, which may define the overall performance of the mathematical model. The granularities may be selected by the orthopaedic surgeon or may be "hard coded" or otherwise preselected.

Subsequently in block 812, initial patient tilt values and an initial orientation of the acetabular cup 104 is determined or chosen. Such initial values may be pre-selected or predetermined or may be selected by the orthopaedic surgeon or other user of the analysis device 402. Regardless, the method 800 subsequently advances to block 814 in which the analysis device 402 determines the set of contact points between the femoral head 118 of the femoral prosthesis 102 and the cup liner 122 of the acetabular cup 104 using the ADL mechanics model with the selected pelvic title values, associated pelvic mobility value, the selected size and type of the hip prosthesis 100, and the selected orientation of the acetabular cup 104 as inputs to the ADL mechanics model. To do so, as discussed above in regard to block 708 of method 700, the analysis device 402 determines a sub-set of contact points for each ADL activity in block 816. Additionally, as discussed above in regard to block 710 of method 700, each ADL activity is temporally discretized and a separate contact point of the corresponding sub-set of contact points is determined for each temporal period in block 818. Subsequently, in block 820, the analysis device 402 generates the final set of contact points for the selected orientation of the acetabular cup 104 based on the individual sub-sets of the contact points of each ADL activity, as discussed above in regard to block 712 of method 700.

In block 822, the analysis device 402 stores the set of contact points generated in block 814. For example, the analysis device 402 may store the set of contact points in the data storage 412. As shown in block 824, the analysis device 402 may store the generated sets of contact points as a function of the particular patient tilt values and cup orientation used as input to the ADL mechanism model to generate the corresponding set of contact points.

Subsequently, in block 826 of FIG. 8B, the analysis device 402 determines whether an additional set of contact points are to be generated for a new combination of pelvic tilt and/or acetabular cup orientation values. If so, the method 800 advances to block 828, in which the analysis device 402 adjusts one or more of the pelvic tilt values and/or one or more of the acetabular cup orientation values (e.g., the inclination value and/or the anteversion value). The analysis device 402 adjusts those values based on the granularity of inputs determined in block 802, and the method 800 subsequently loops back to 814 of FIG. 8A to calculate a set of contact points using the adjusted pelvic tilt value(s) and/or acetabular cup orientation value(s). In this way, the analysis device 402 steps through a range of different pelvic tilt values and acetabular cup orientation values combinations such that the final sets of contact points cover a "universe" of different possible combinations.

As discussed above, it should be appreciated that the ADL mechanics model has been described above as iteratively calculating the sets of contact points for each combination of pelvic tilt and acetabular cup orientation values. However, in other embodiments, the ADL mechanics model may be designed or formulated such that the complete "universe" of different possible pelvic tilt and orientation values is determined as a single calculation or equation.

Referring back to block 826 of FIG. 8B, after the set of contact points for each combination of pelvic tilt values and acetabular cup orientation values has been determined, the method 800 advances to block 830. In block 830, the analysis device 402 generates a mathematical model based on the pool of sets of contact points generated in blocks 814-828. As discussed above, the mathematical model is a model of the generated sets of contact points, which are the result of the "universe" of pelvic tilt and acetabular cup orientation values. As such, using the measured pelvic tilt measurements of a particular patient, the mathematical model is capable of generating the corresponding group of sets of contact points between the femoral prosthesis 102 and the acetabular cup 104 for the complete range of orientations of the acetabular cup 104 of interest. Because such individual calculations have already been completed, it should be appreciated that the mathematical model may perform faster than the ADL mechanics model in the generation of the resultant sets of contact points for that particular patient. For example, mathematical model may produce the resultant set of contact points in less than five minutes, in less than three minutes, in less than one minute, in less than thirty seconds, in less than one second, and/or in less than one millisecond in some embodiments.

The mathematical model may be embodied as any type of mathematical model capable of generating the sets of contact points using the patient's pelvic tilt measurements as an input. For example, to generate the mathematical model, the analysis device 402 may perform any one or more of the techniques described in the journal article entitled "Development Of A Statistical Shape-Function Model Of the Implanted Knee For Real-Time Prediction Of Joint Mechanics" by Gibbons et al. (Gibbons K. et al. Development Of A Statistical Shape-Function Model Of the Implanted Knee For Real-Time Prediction Of Joint Mechanics, *Journal of Biomechanics* 2019; 88:55-63), the entirety of which is incorporated herein by reference.

Regardless, as shown in FIG. 8B, the analysis device 402 may generate or determine a linear response model in block 832 based on the generated sets of contact points. Additionally or alternatively, the analysis device 402 may generate or determine a response surface model in block 834, a neural network model in block 836, and/or a statistical fitting model in block 838 based on the generated sets of contact points.

After the mathematical model has been generated in block 830, the mathematical model may be subsequently used to determine or calculate the sets of contact points for the present patient using the measured patient pelvic tilt values as an input. To do so, as shown in block 832, the analysis device 402 utilizes the mathematical model to determine a set of contact points for each orientation in a range of cup orientations (i.e., the range of cup orientations used to generate the mathematical model) using the patient pelvic tilt measurements as an input. As discussed above, the range of cup orientations is "hard-coded" into the mathematical model and, as such, the illustrative mathematical model is configured to generate a pool of sets of contact points for the patient in a single calculation, rather than an iterative approach. Of course, in other embodiments, the generated mathematical model may be designed to utilize an iterative approach with regard to the range of acetabular cup orientations.

Referring now back to FIG. 6B, after the analysis device 402 has determined the sets of contact points in block 632 using either the method 700 or the method 800 discussed above, the method 600 advances to block 636 in some embodiments. In block 636, the analysis device 402 may be configured to determine an impingement-free range of motion between the femoral prosthesis 102 and the acetabular cup 104. That is, the analysis device 402 determines a range of motion between the femoral prosthesis 102 and the acetabular cup 104 that does not result in impingement of the neck 114 of the femoral prosthesis 102 and the edge of the cup liner 122 of the acetabular cup 104.

To do so, in block 638, the analysis device 402 may determine the impingement-free range of motion between the femoral prosthesis 102 and the acetabular cup 104 based on three-dimensional models of the femoral prosthesis 102 and of the acetabular cup 104. It should be appreciated that such three-dimensional models may be based on the type and size of the particular femoral prosthesis 102 and the acetabular cup 104 selected by the orthopaedic surgeon.

Additionally, in some embodiments in block 640, the analysis device 402 may determine the impingement-free range of motion for a range of different orientations of the femoral prosthesis 102 relative to the patient's femur and for a range of different orientations of the acetabular cup 104 relative to the patient's acetabulum 200.

Figure 14:
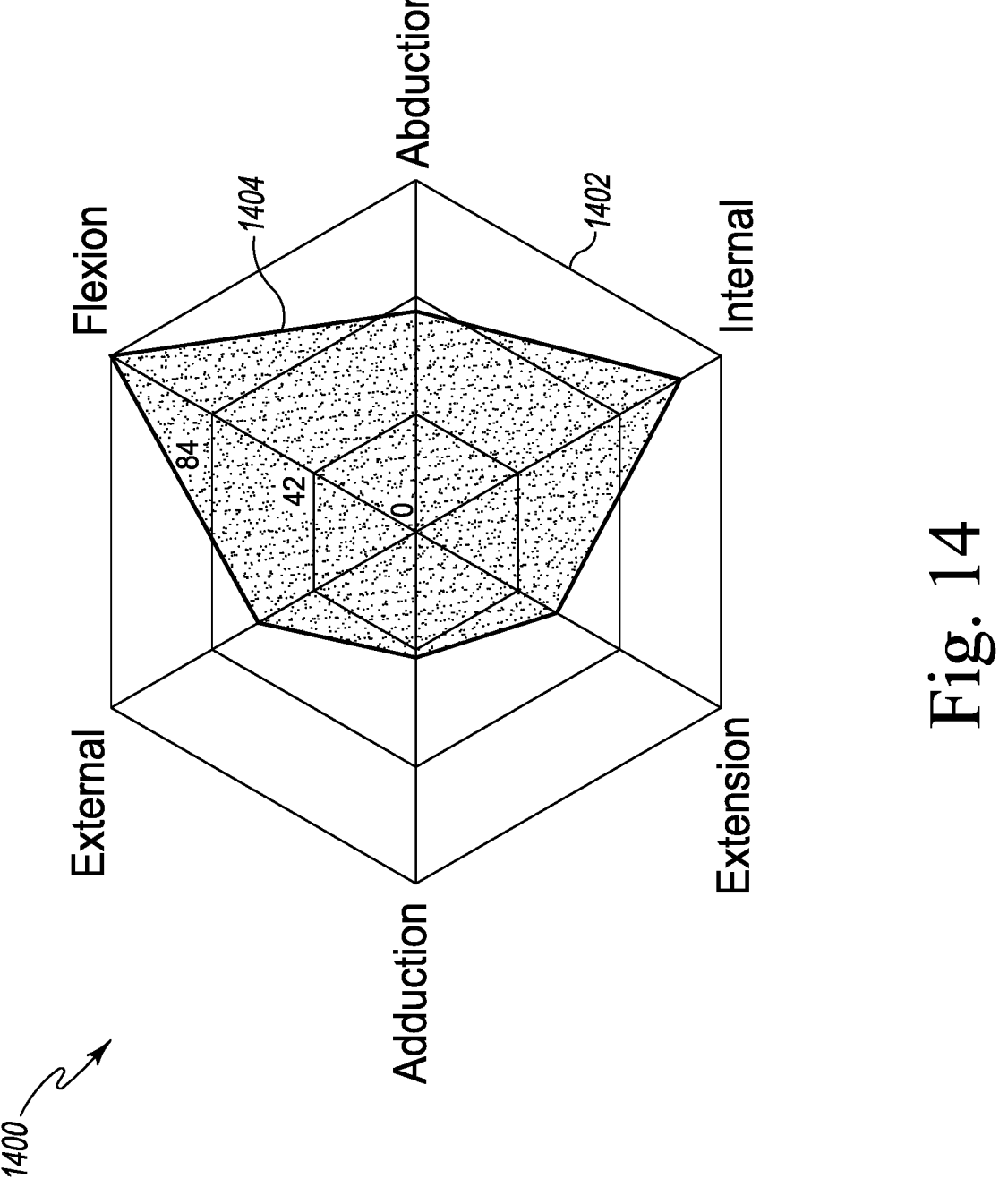
FIG. 14 is an illustrative screen image that may be displayed during the performance of the method of FIGS. 6A-6D showing a graphical representation of an impingement-free range of motion between the femoral prosthesis and the acetabular cup of the hip prosthesis of FIG. 1 such that the area of the graphical representation is indicative of the impingement-free range of motion.

For example, as shown in FIG. 14, the analysis device 402 may determine a graphical representation 1400 of the impingement-free range of motion between the femoral prosthesis 102 and the acetabular cup 104. The illustrative graphical representation 1400 shows the degrees of flexion, abduction, internal rotation, extension, adduction, and external rotation achievable with the hip prosthesis 100, given an orientation of the femoral prosthesis 102 and the acetabular cup 104, that does not result in impingement between the neck 114 of the femoral prosthesis 102 and the edge of the cup liner 122 of the acetabular cup 104. In the illustrative embodiment, the graphical representation 1400 includes a degree chart 1402 having concentric hexagons that each define a particular degree of movement depending on the associated axis. That is, each hip joint movement has an associated point on the degree chart 1402 that defines the maximum degree of that movement before impingement of the femoral prosthesis 102 and the acetabular cup 104 occurs. For example, in the embodiment of FIG. 14, the analysis device 402 has determined the patient's hip can be flexed to a degree of about 126 degree before impingement occurs, whereas the patient's hip can be extended only to about 60 degrees before impingement occurs. Additionally, the analysis device 402 has determined the patient's hip can be internally rotated to a degree of about 112 degrees before impingement occurs, whereas the patient's hip can be externally rotated to about 63 degrees before impingement occurs. Furthermore, the analysis device 402 has determined the patient's hip can be moved to about 80 degrees of abduction before impingement occurs, whereas the patient's hip can be moved to about 48 degrees of adduction before impingement occurs. A range-of-motion boundary 1404 is defined around each corresponding maximum degree of movement, and the area of the range-of-motion boundary 1404 provides a visualization of the range of impingement-free motion achievable by the hip prosthesis 100 with the selected orientation of the acetabular cup 104. As such, in the illustrative embodiment, the area bounded by the range-of-motion boundary 1404 is indicative of the impingement-free range of motion of the hip prosthesis 100. Of course, in other embodiments, other criteria may be used to determine the impingement-free range of motion of the hip prosthesis 100 for the particular patient. Additionally, in other embodiments, bone-on-bone impingement may also be determined an analyzed.

Referring back to FIG. 6B, after the analysis device as determined the impingement-free range of motion of the hip prosthesis 100, the method 600 advances to block 642. In block 642, the analysis device 402 identifies a set of acceptable orientations of the acetabular cup 104 from the generated sets of contact points, which include a set of contact points for each cup orientation in a range of cup orientations as discussed above. To do so, in the illustrative embodiment, the analysis device 402 determines, in block 644, an initial set of cup orientations based on the pool of sets of contact points determined in block 632. Generally, the initial set of cup orientations includes each orientation of the acetabular cup 104 that corresponds to a different set of contact points generated in block 632 (i.e., the cup orientation that was used to generate the corresponding set of contact points).

In block 646, the analysis device 402 identifies those orientations of the acetabular cup 104 that result in edge loading of the cup liner 122 of the acetabular cup 104. To do so, the analysis device 402 determines whether any contact point results in edge loading based on the distance of each contact point of the corresponding set of contact points relative to the edge of the cup liner 122. For example, as shown in FIG. 13, the analysis device 402 may analyze the distance of each contact point of the set of contact points 1300 from an edge boundary 1312 indicative of the inner (distal) edge of the cup liner 122 and forms the outer boundary of a two-dimensional cup liner map 1310. If any portion of a contact point lies on or over the edge boundary 1312 of the cup liner map 1310 (which corresponds to the edge of the cup liner 122) or lies within a reference threshold distance of the edge boundary 1312, the orientation of the acetabular cup 104 corresponding to that set of contact points is deemed to result in edge loading of the acetabular cup 104 by the femoral prosthesis 192.

The reference threshold distance from the edge boundary 1312 for a contact point to be considered an "edge loading contact point," and the corresponding orientation of the acetabular cup 104 to result in edge loading, may be fixed or identical across sizes of the acetabular cup 104 or may be relative to the size of the acetabular cup 104. For example, in an illustrative embodiment, the analysis device 402 may determine that a contact point is an "edge loading contact point" if that contact point is within an arc length of 1.5 millimeters or less of the inner (distal) edge of the cup liner 122 (indicated as edge boundary 1312 in FIG. 13). In another embodiment, the analysis device 402 may determine that a contact point is an "edge loading contact point" if that contact point is within an arc length of 1.0 millimeters or less of the inner (distal) edge of the cup liner 122. In a further embodiment, the analysis device 402 may determine that a contact point is an "edge loading contact point" if that contact point is within an arc length of 0.5 millimeters or less of the inner (distal) edge of the cup liner 122. Additionally or alternatively, in other embodiments, the reference distance for a contact point to be considered an "edge loading contact point" may be relative to the size of the acetabular cup 104. For example, the reference distance from the inner (distal) edge of the cup liner 122 to consider a contact point as edge loading may be selected such that a ratio of the distance from the inner (distal) edge of cup liner 122 to the inner diameter of cup liner 122 is in the range of 0.034 to 0.067, in the range of 0.044 to 0.0577, or about 0.047. Regardless, it should be appreciated that by increasing the reference distance, the confidence of the identification of all contact points that result in edge loading of the acetabular cup 104 may be increased.

Figure 18:
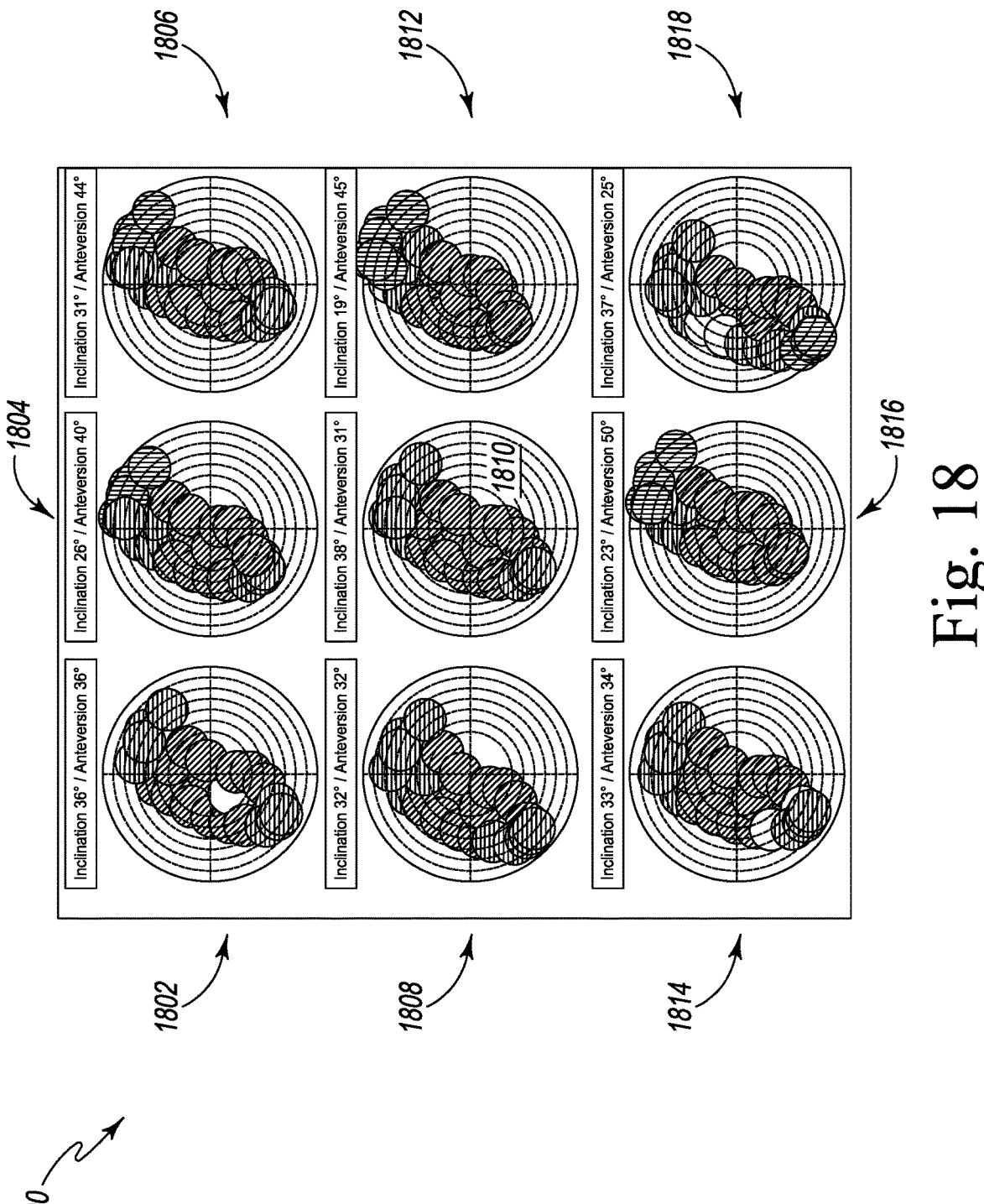
FIG. 18 is an illustrative screen image that may be displayed during the performance of the method of FIGS. 6A-6D showing a number of contact plots with each having contact indicators corresponding to contact points between the femoral prosthesis and the acetabular cup of the hip prosthesis of FIG. 1 and corresponding to a different orientation of the acetabular cup relative to an acetabulum of the patient.

Several sample contact plots having edge loading are shown in FIG. 18 and described in more detail below. As shown, each of contact plots 1804, 1806, 1812, 1816, and 1818 have at least one contact point that lies on, over, or within a reference threshold of the corresponding edge boundary 1312 of the cup liner map 1310. As such, each of the orientations of the acetabular cup 104 corresponding to each contact plot 1804, 1806, 1812, 1816, and 1818 is deemed to result in edge loading of the acetabular cup 104 and, in some embodiments, may be highlighted in the corresponding contact plot using a suitable methodology, such as a change in the color of the corresponding contact indicator (e.g., a red color).

Referring back to FIG. 6B, after the analysis device 402 has identified those cup orientations resulting in edge loading of the acetabular cup 104, the analysis device 402 separates those edge-loading cup orientations from the initial set of cup orientations in block 648. As such, the resulting set of acceptable cup orientations includes the original set of cup orientations, each corresponding to a separate generated set of contact points, minus those cup orientations determined to result in edge loading of the acetabular cup 104. Additionally, in some embodiments in block 650, the analysis device 402 may also remove those cup orientations that were determined to result in impingent of the femoral prosthesis 102 on the acetabular cup 104 in block 636.

Figure 6C:
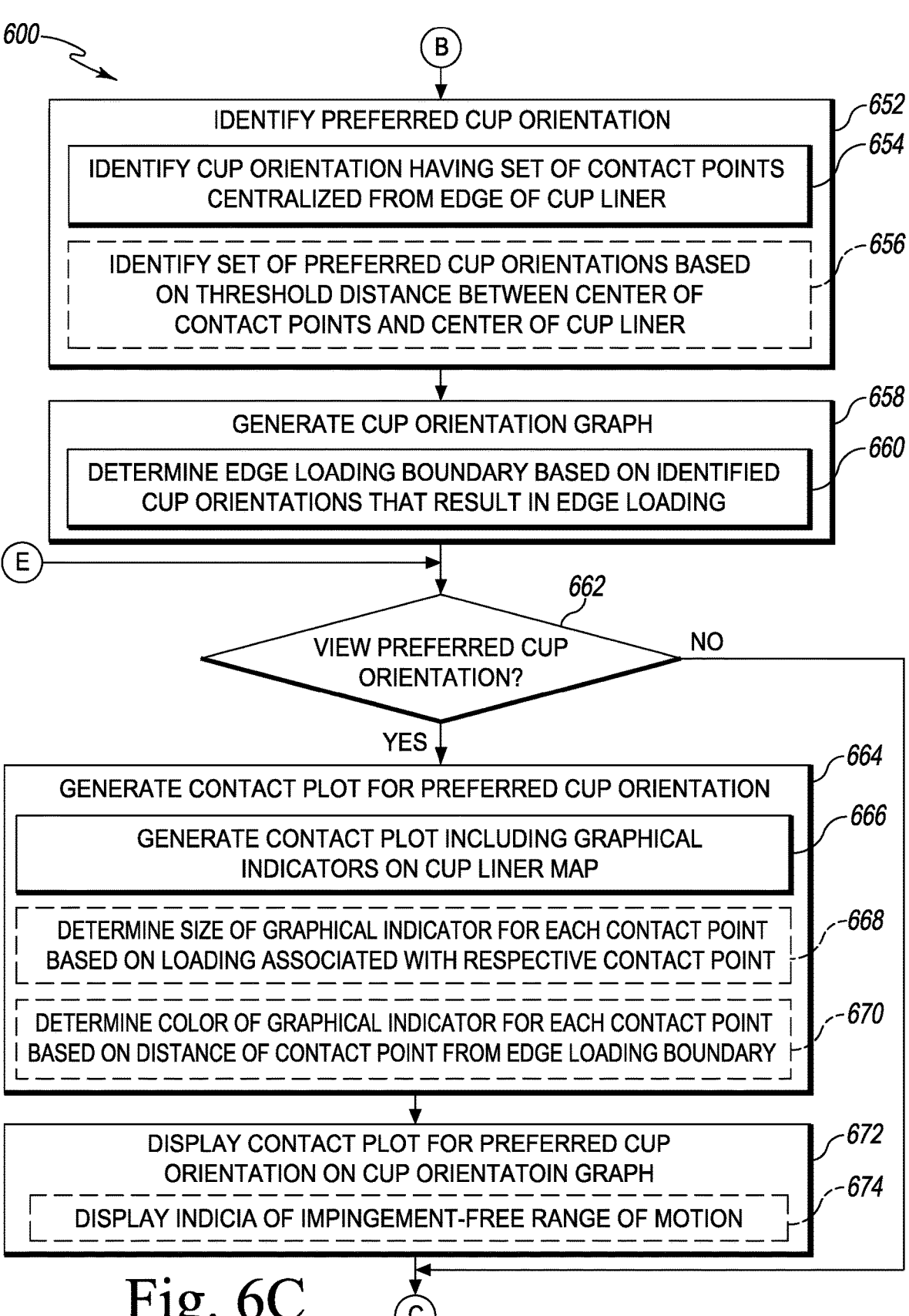

After the analysis device 402 has determined the set of acceptable cup orientations in block 642, the method 600 advances to block 652 of FIG. 6C. In block 652, the analysis device 402 identifies one or more preferred orientations of the acetabular cup 104 relative to the patient's acetabulum 200. Of course, it should be appreciated that the preferred cup orientation(s) may or may not be the "optimized" cup orientation depending on the selection criteria. In the illustrative embodiment, the analysis device 402 determines the preferred cup orientations from the set of acceptable cup orientations determined in block 642 based on the degree of centralization on the acetabular cup liner 122 of the set of contact points corresponding to each acceptable cup orientation in block 654. To do so, the analysis device 402 may utilize any suitable methodology to determine the amount of centralization of the set of contact points.

Figure 15:
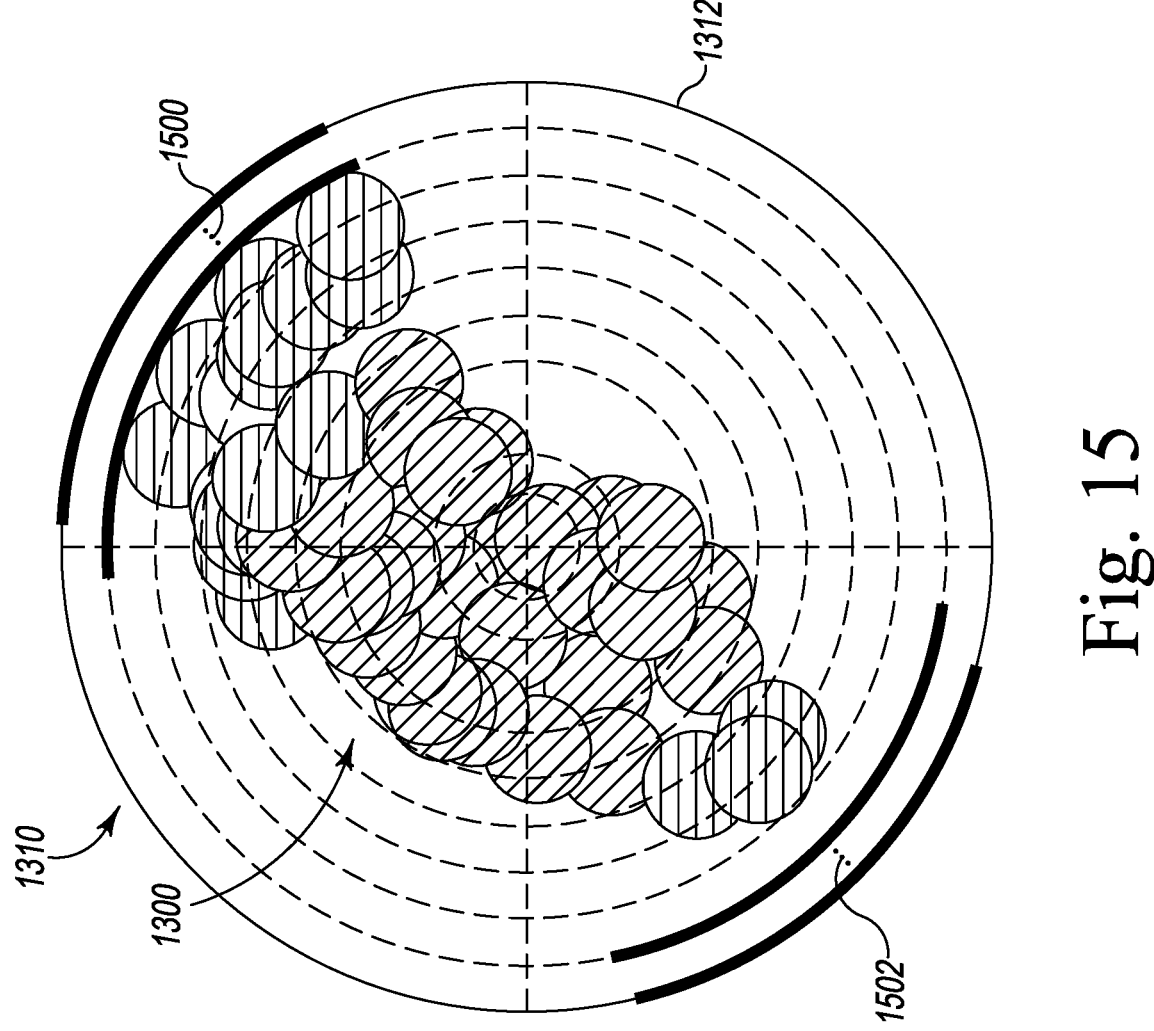
FIG. 15 is an illustrative screen image that may be displayed during the performance of the method of FIGS. 6A-6D showing determined distances between the outmost contact points of a set of contact points and an edge boundary indicative of the edge of the cup liner of the hip prosthesis of FIG. 1, which a modification to the color (or hashing) of the contact points as those contact points near the edge boundary.

For example, in the illustrative embodiment, the analysis device 402 determines the preferred orientation of the acetabular cup 104 based on the distance between the outer most contact points (i.e., those contact points closet to the edge boundary 1312 of the cup liner map 1310) and the edge boundary 1312. For example, as shown in FIG. 15, the analysis device 402 may be configured to determine a pair of distances 1500, 1502 defined between the outmost contact points of the set of contact points 1300 and the edge boundary 1312 of the cup liner map 1310. The closer those distances 1500, 1502 match, the more centralized the set of contact points 1300 are relative to a center of the cup liner 122 (as indicated by the cup liner map 1310). Additionally, in some embodiments, the analysis device 402 may be configured to provide further indications on those contact points 1300 that are near the edge boundary 1312 (e.g., within a reference threshold distance). For example, the analysis device 402 may alternate the color (e.g., change to the color red) of those contact points 1300 that are over, touching, and/or within a reference distance of the edge boundary 1312.

Of course, in other embodiments, other methods for determining the centralization of the set of contact points 1300 may be used. For example, in some embodiments in block 656, the analysis device 402 may determine a center of mass of the set of contact points 1300 and determine the centralization of that set of contact points 1300 based on the distance between the determined center of mass and the center of the cup liner 122 (as indicated by the cup liner map 1310). If that distance is below a reference threshold distance, the analysis device 402 may determine that the acetabular cup orientation associated with that set of contact points is a preferred acetabular cup orientation. In still other embodiments, the analysis device 402 may determine an average distance from the edge boundary 1312 of the cup liner map 1310 for the set of contact points. In doing so, the analysis device 402 may apply a weighting factor to some contact points to reduce the effect of outliers.

Figure 16:
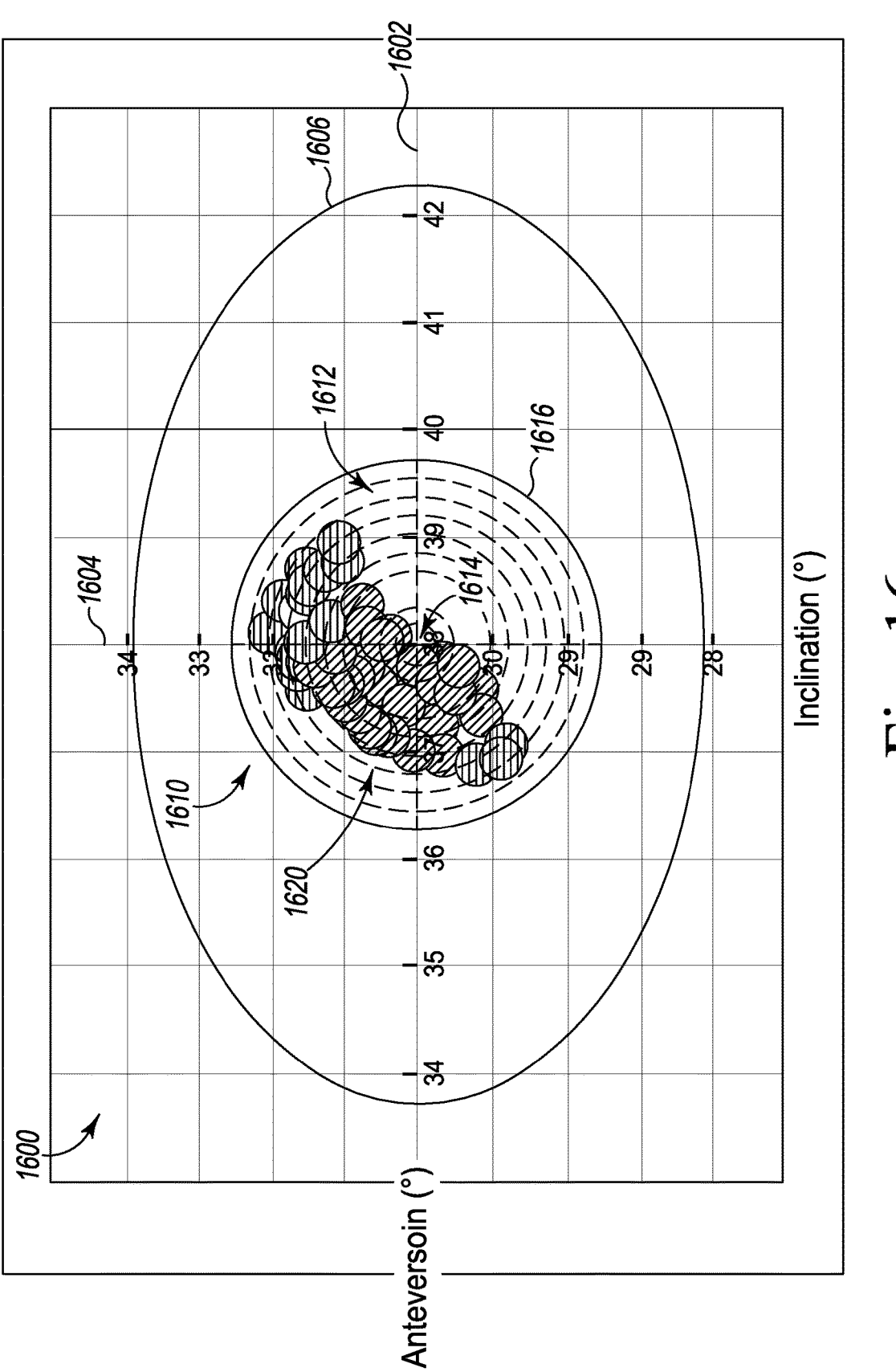
FIG. 16 is an illustrative screen image that may be displayed during the performance of the method of FIGS. 6A-6D showing a cup orientation graph including a contact plot having contact indicators corresponding to contact points between the femoral prosthesis and the acetabular cup of the hip prosthesis of FIG. 1 and an edge loading boundary that corresponds to contact points that result in edge loading of the acetabular cup.

Regardless, after the analysis device 402 has determined the set of acceptable acetabular cup orientations in block 642 and the preferred acetabular cup orientation(s) in block 652, the method 600 advances to block 658. In block 658, the analysis device 402 generates a cup orientation graph. An illustrative cup orientation graph 1600 is shown in FIG. 16 and includes an abscissa axis 1602 of degrees of anteversion of the acetabular cup 104 and an ordinate axis 1604 of degrees of inclination of the acetabular cup 104 relative to the patient's acetabulum 200.

Figure 17:
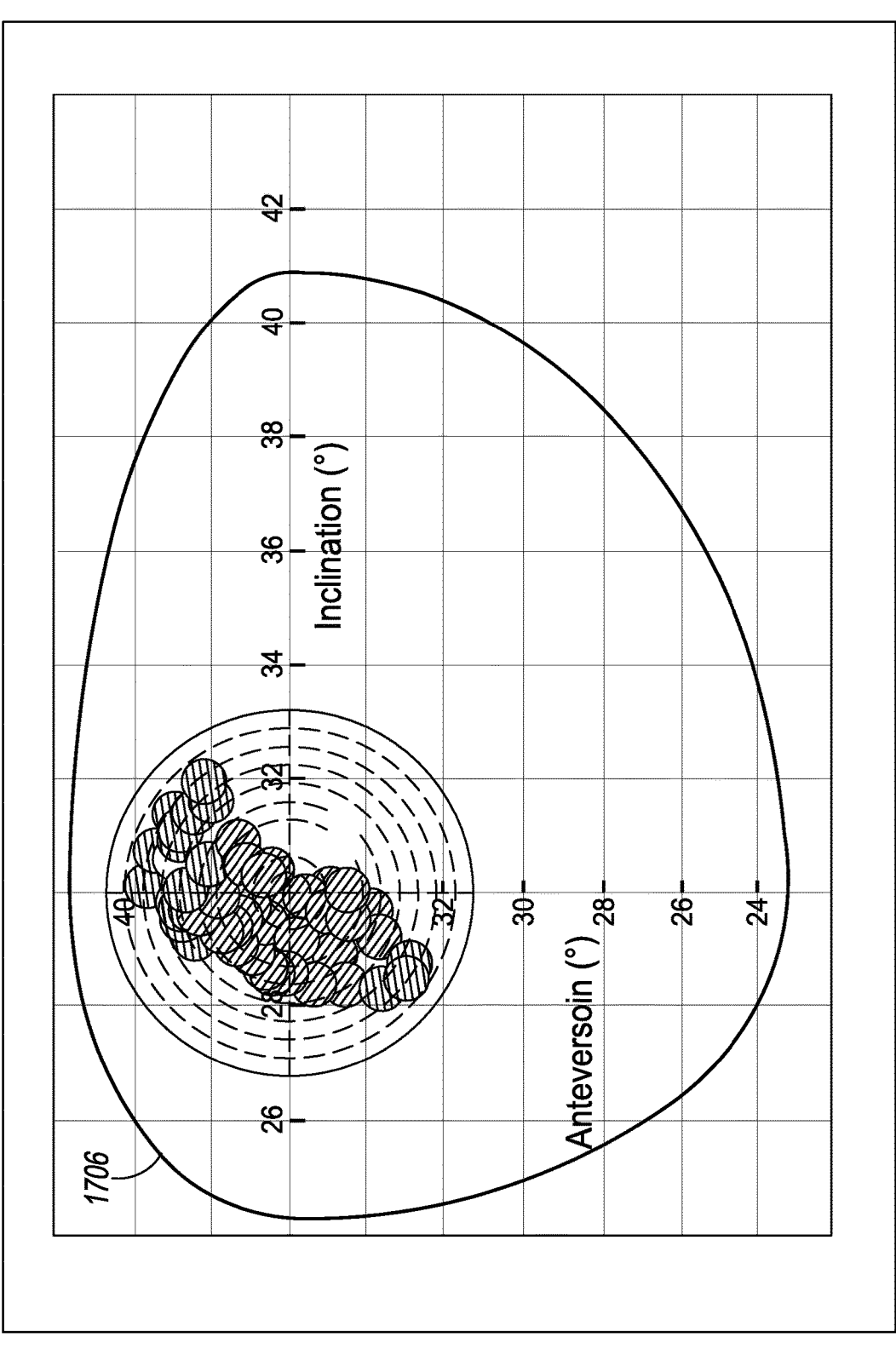
FIG. 17 is an illustrative screen image that may be displayed during the performance of the method of FIGS. 6A-6D showing another embodiment of a cup orientation graph including a contact plot having contact indicators corresponding to contact points between the femoral prosthesis and the acetabular cup of the hip prosthesis of FIG. 1 and an edge loading boundary that corresponds to the cup orientations that result in edge loading of the acetabular cup.

Referring back to FIG. 6C, as part of the generation of the cup orientation graph 1500, the analysis device 402 may also determine, in block 660, an edge loading boundary 1606 of orientation values that result in edge loading of the acetabular cup 104 based on the set of acetabular cup orientations that were determined to result in edge loading in block 646. That is, the analysis device 402 generates a boundary defining acetabular cup orientations (i.e., degrees of inclination and anteversion) outside of which results in edge loading of the acetabular cup 104. An illustrative edge loading boundary 1606 is shown in FIG. 16, which has a generally oval or elliptical shape. Of course, it should be appreciated that the edge loading boundary 1606, when initially determined based on the defined edge-loading cup orientations, may have a "noisy" or erratic shape depending on the location of those edge-loading cup orientations. As such, the analysis device 402 may employee some amount of data smoothing, such as spline fitting, to generate the final shape of the edge loading boundary 1606. Additionally, it should be appreciated that the edge loading boundary 1606 may not be a perfect ellipse in some embodiments, depending on the location of the edge-loading cup orientations. For example, as shown in FIG. 17, the edge loading boundary 1706 may have a more irregular shape, although still substantially oval.

Referring now back to FIG. 6C, after the analysis device 402 has generated the cup orientation graph, the analysis device 402 may determine whether the orthopaedic surgeon (or other user of the analysis device 402) desires to view the contact plot for the preferred cup orientation in block 662. If so, the analysis device 402 generates a contact plot for the set of contact points associated with the preferred cup orientation in block 664. To do so, in block 666, the analysis device 402 generates a contact plot including a cup liner map and a graphical contact indicator for each contact point of the corresponding set of contact points, each of which is located on the cup liner map in a position indicative of the location of the corresponding contact point relative to the cup liner 122 of the acetabular cup 104. An illustrative contact plot 1610 is shown in FIG. 16 and includes a cup liner map 1612 positioned on the cup orientation graph 1600. The cup liner map 1612 is illustratively embodied as a group of concentric circular boundaries emanating from a center 1614 of the cup liner map 1612, which corresponds to the center of the cup liner 122 of the acetabular cup 104, to an edge boundary 1616, which corresponds to the edge of the cup liner 122. The group of concentric circular boundaries provides a visual indication of the location of the contact points relative to the center 1514 and the edge boundary 1516 of the cup liner map 1512. Each contact point of the corresponding set of contact points is represented by a corresponding graphical contact indicator 1620. The contact indicators 1620 of the contact plot 1610 are illustratively embodied as circles. However, in other embodiments, the contact indicators 1620 may be embodied as any suitable visual indicator capable of providing an indication to the orthopaedic surgeon of the location of the corresponding contact point on the cup liner 122 of the acetabular cup 104.

In some embodiments, the contact indicators 1620 may provide information in addition to the location of the corresponding contact point on the cup liner 122 of the acetabular cup 104. For example, referring back to block 668 of FIG. 6C, the analysis device 402 may determine a size of each graphical contact indicator 1620 corresponding to a contact point of the set of contact points of the preferred cup orientation. For example, in embodiments in which the contact indicators 1620 are embodied as circles, the analysis device 402 may determine the radius or diameter of each corresponding circle. Regardless, the size of the contact indicator 1620 may be based on, and indicative of, the loading of the hip prosthesis 100 at the corresponding contact point. The loading experienced by the hip prosthesis 100 is determined as part of the ADL mechanics model and/or the mathematical model used to generate the set of contact points and, in the illustrative embodiment, is indicated by the size of the corresponding contact indicator 1620 (e.g., a larger contact indicator means a larger amount of loading occurred at the corresponding contact point).

Additionally, the analysis device 402 may determine a color of each graphical contact indicator 1620 in block 670. In the illustrative embodiment, the color of each contact indicator 1620 is based on, and indicative of, a distance of the corresponding contact point from the edge of the cup liner 122, which is indicated on the contact plot 1610 by the edge boundary 1616. As such, contact indicators 1620 closer to the edge boundary 1616 will have different colors (e.g., a more blue color) than contact indicators 1620 located more toward the center 1614 of the contact map 1610 (e.g., a more green color). Additionally, a special color, such as red, may be used for those contact indicators 1620 lying on or over the edge boundary 1616 as shown in FIG. 18 with regard to contact plots 1804, 1806, 1812, 1816, and 1818.

After the analysis device 402 has generated the contact plot in block 664, the method 600 advances to block 672 in which the analysis device 402 displays the contact plot for the preferred orientation of the acetabular cup 104 on the display 416. Additionally, in some embodiments, the analysis device 402 may display the graphical representation 1400 of the impingement-free range of motion of the between the femoral prosthesis 102 and the acetabular cup 104 as determined in block 636 and shown in FIG. 14.

Figure 6D:
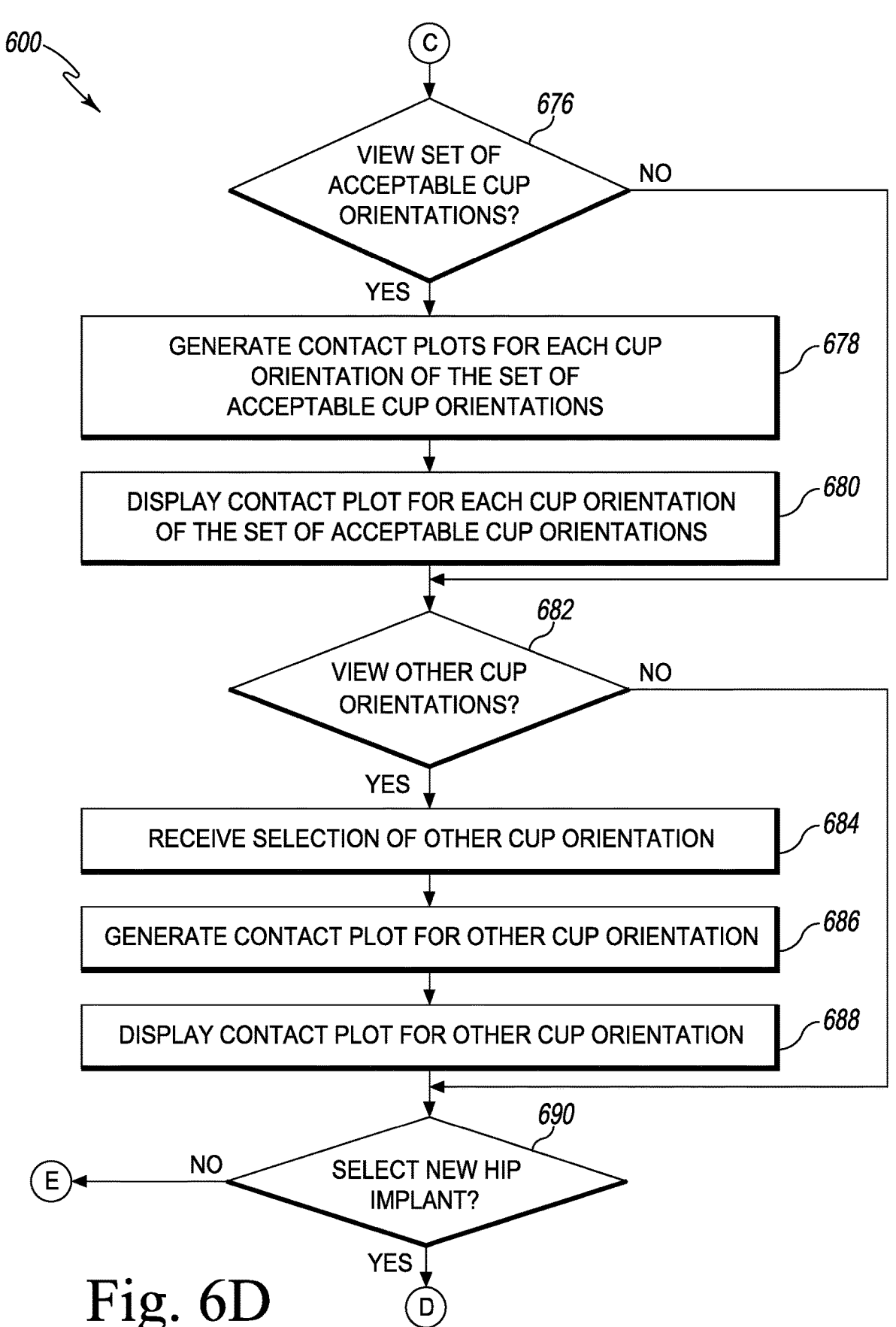

After the analysis device 402 has displayed the contact plot 1610 for the preferred cup orientation or if the orthopaedic surgeon decides not to view the determined preferred cup orientation in block 662, the method 600 advances to block 676 of FIG. 6D. In block 676, the analysis device 402 may determine whether the orthopaedic surgeon (or other user of the analysis device 402) desires to view the contact plots for the set of acceptable acetabular cup orientations as determined previously in block 642. If so, in block 678, the analysis device generates a contact plot for each acetabular cup orientation of the set of acceptable cup orientations (i.e., for each set of contact points that do not result in edge loading of the acetabular cup 104). Each of those contact plots are similar to the contact plot 1610 shown in FIG. 16 and described above in regard to block 664.

Figure 19:
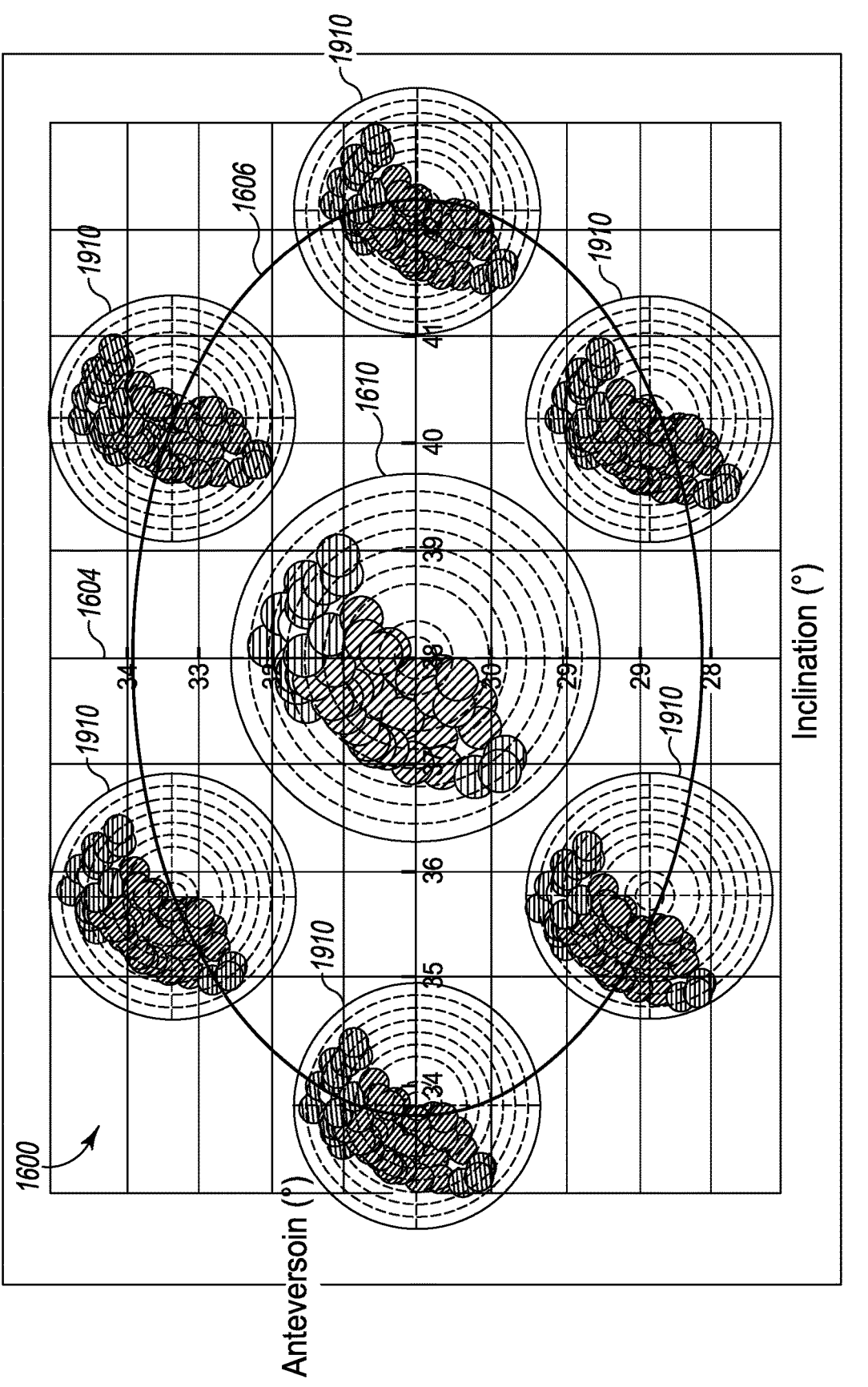
FIG. 19 is an illustrative screen image that may be displayed during the performance of the method of FIGS. 6A-6D showing a cup orientation graph including a number of contact plots with each corresponding to a different orientation of the acetabular cup relative to an acetabulum of the patient and having contact indicators corresponding to contact points between the femoral prosthesis and the acetabular cup of the hip prosthesis of FIG. 1 and an edge loading boundary that corresponds to sets of contact points that result in edge loading of the acetabular cup.

Subsequently, in block 680, the analysis device 402 may display the generated contact plots on the display 416. For example, as shown in FIG. 19, the analysis device 402 may display the preferred contact plot 1610 in the center of the cup orientation graph 1600 and the other contact plots 1910 of the remaining acceptable cup orientations (or a sub-set of those contact plots 1910) on the edge loading boundary 1606. The preferred contact plot 1610 may be based on criteria in addition to the "centralization" of the contact points on the cup liner 122, such as the orthopaedic surgeon's preference, a particular surgical technique that is to be used, and/or other considerations. Additionally, it should be appreciated that the contact plots 1910 displayed on the edge loading boundary 1606 are indicative of values of the anteversion and/or inclination of the orientation of the acetabular cup 104, beyond which result in edge loading of the acetabular cup 104 (i.e., is greater or lesser depending on the location of the corresponding contact plot 1812). That is, as shown in FIG. 19, none of the contact plots 1910 includes a contact indicator lying on or beyond the edge loading boundary 1606 of the corresponding cup liner map 1612. Of course, in other embodiments, the analysis device 402 may display additional or other contact plots 1910 on the cup orientation graph 1600.

After the analysis device 402 has displayed the contact plots for the acceptable cup orientations or if the orthopaedic surgeon decides not to view the acceptable cup orientations in block 676, the method 600 advances to block 682. In block 682, the analysis device 402 may determine whether the orthopaedic surgeon (or other user of the analysis device 402) desires to view contact plots for any other acetabular cup orientations, which may include those that result in edge loading of the acetabular up 104 and/or those exhibiting impingement between the femoral prosthesis 102 and the acetabular cup 104. If so, in block 684, the analysis device 402 receives a selection of the other acetabular cup orientation. For example, the orthopaedic surgeon may select the desired cup orientation or enter particular degrees of anteversion and inclination to select the corresponding acetabular cup orientation. In any case, in block 686, the analysis device 402 generates a contact plot for the selected acetabular cup orientation as discussed above. Additionally, in block 688, the analysis device 402 displays the generated contact graph on the display 416 as discussed above.

After the analysis device 402 has displayed the contact plot for the selected cup orientation or if the orthopaedic surgeon decides not to view another cup orientation in block 682, the method 600 advances to block 690. In block 690, the analysis device 402 determines whether the orthopaedic surgeon would like to analyze the position of another hip prosthesis. For example, the orthopaedic surgeon may select a completely different type of hip prosthesis or select a different size of the present type of the hip prosthesis. If so, the method 600 loops back to block 630 in which the analysis device 402 determines the type and size of the new hip prosthesis as discussed above. However, if not, the method 600 loops back to block 662 in which the analysis device 402 again determines whether the orthopaedic surgeon desires to view the preferred cup orientation.

Figure 9B:
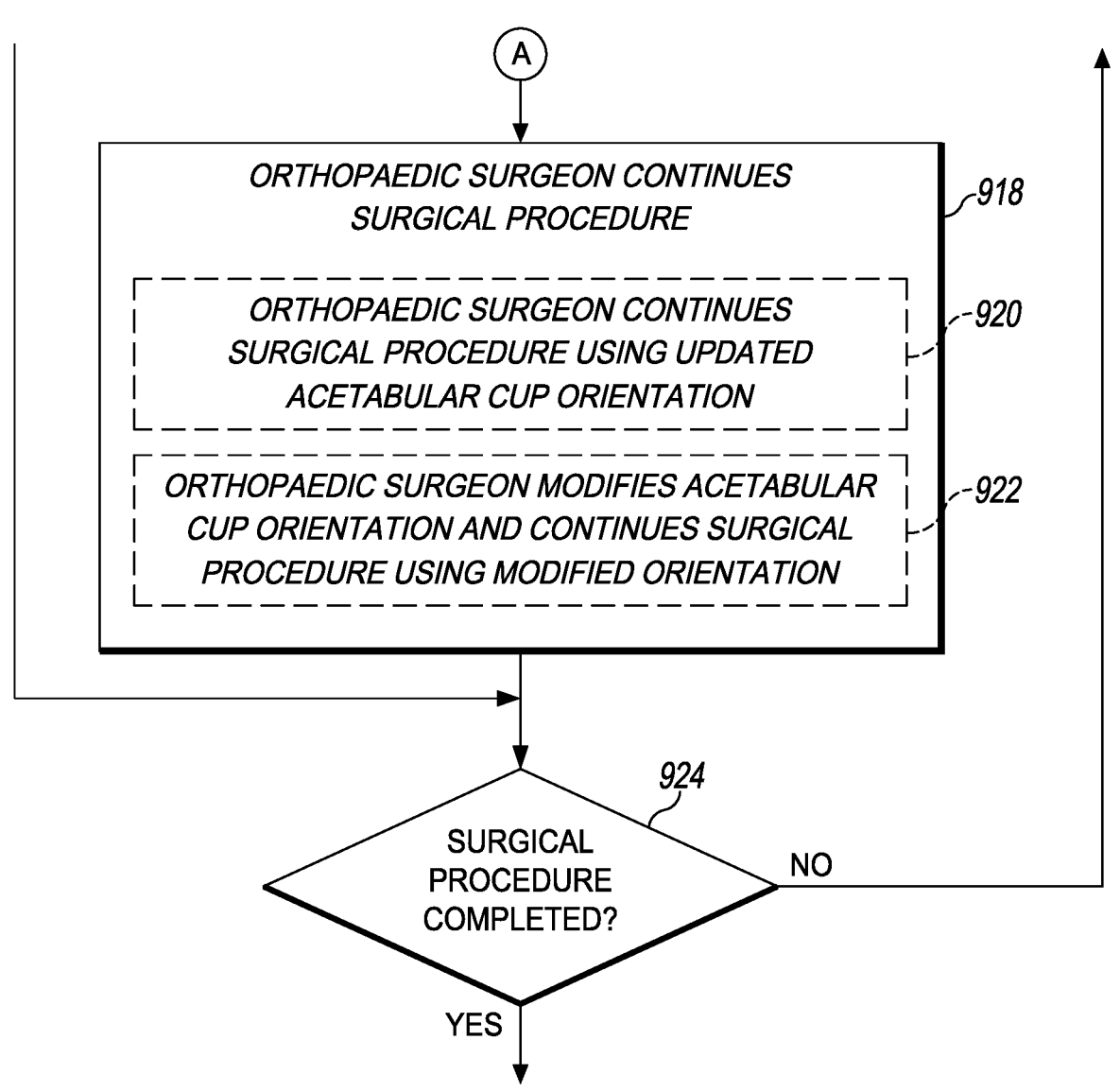

Referring now to FIGS. 9A and 9B, in some embodiments, the analysis device 402 may also execute a method 900 for intra-operatively monitoring the positioning of the hip prosthesis 100 during the performance of the orthopaedic surgical procedure to implant the hip prosthesis 100 in the patient. For example, the method 900, or portions thereof, may be embodied as a set of executable instructions stored on the analysis device 402 and executable by the analysis device 402. As such, it should be appreciated that the operations of the method 900 may be performed by one or more components of the analysis device 402 and/or devices communicatively coupled to the analysis device 402.

The method 902 begins with block 902 in which the analysis device 402 pre-operatively determines a planned or desired orientation of the acetabular cup relative to the patient's acetabulum 200. To do so, the analysis device 402 may execute method 600 described above in regard to FIG. 6. As such, it should be appreciated that while the method 600 may be used pre-operatively to pre-plan the desired orientation of the acetabular cup 104, the method 900 may be executed during the orthopaedic surgical procedure itself to monitor and/or adjust the actual, present orientation of the acetabular cup 104.

Subsequently, in block 904, the analysis device 402 determines whether the orthopaedic surgeon desires to monitor the positioning of the hip prosthesis 100 (e.g., the orientation of the acetabular cup 104) while performing the associated orthopaedic surgical procedure. If so, the method 900 advances to block 906 in which the analysis device 402 determines the present orientation of the acetabular cup 104 relative to the patient's acetabulum 200. To do so, the analysis device 402 may determine the present orientation of the acetabular cup 104 based on medical images of the patient's acetabulum 200 generated and obtained during the performance of the orthopaedic surgical procedure. For example, the imaging device 404 of the system 400 may be configured to generate medical images of the patient's acetabulum 200 during the orthopaedic surgical procedure and transmit or otherwise provide those medical images to the analysis device 402. Alternatively, in embodiments in which the system 400 includes the surgical tracking system 408, the analysis device 402 may be determine the preset orientation of the acetabular cup 104 based on surgical navigation data provided by the surgical tracking system 408 in block 910.

Regardless, after the analysis device 402 has determined the present orientation of the acetabular cup 104 in block 906, the method 900 advances to block 912 in which the analysis device 402 generates a contact plot for the determined present orientation of the acetabular cup 104. To do so, the analysis device 402 may use the methodology described in detail above in regard to block 664 of method 600. Of course, should the present orientation of the acetabular cup 104 not be included in the range of cup orientations for which a set of contact points was determined in block 632 of method 600, the analysis device 402 may also determine the associated set of contact points for the present orientation of the acetabular cup 104 using the methodology described above in regard to block 632. Alternatively, in other embodiments, the analysis device 402 simply select a cup orientation in the range of orientations for which a set of contact points was determined in block 632 that is closest to the determined present orientation of the acetabular cup 104. In some embodiments, the analysis device 402 may also determine the impingement-free range of motion between the femoral prosthesis 102 and the acetabular cup 104 as discussed above in regard to block 636 of method 600 of FIG. 6A-6D.

In block 914, the analysis device 402 displays the contact plot for the present orientation of the acetabular cup 104. To do so, the analysis device 402 may use the methodology described above in regard to block 672 of method 600 in regard the displaying of the contact plot for a preferred cup orientation. For example, in some embodiments, the analysis device 402 may display the contact plot for the present orientation of the acetabular cup 104 on the cup orientation graph 1600 as shown and described above in regard to FIG. 16. Additionally, in block 914, the analysis device 402 may display indicia of the impingement-free range of motion determined in block 912.

Additionally, in some embodiments in block 916, the analysis device 402 may be configured to determine a difference between the pre-operative, planned orientation of the acetabular cup 104 and the determined present orientation of the acetabular cup 104. For example, the analysis device 402 may display a difference in the inclination and anteversion values of the two cup orientations or show the contact plots for each of the pre-operative and intra-operative cup orientations.

Figure 20:
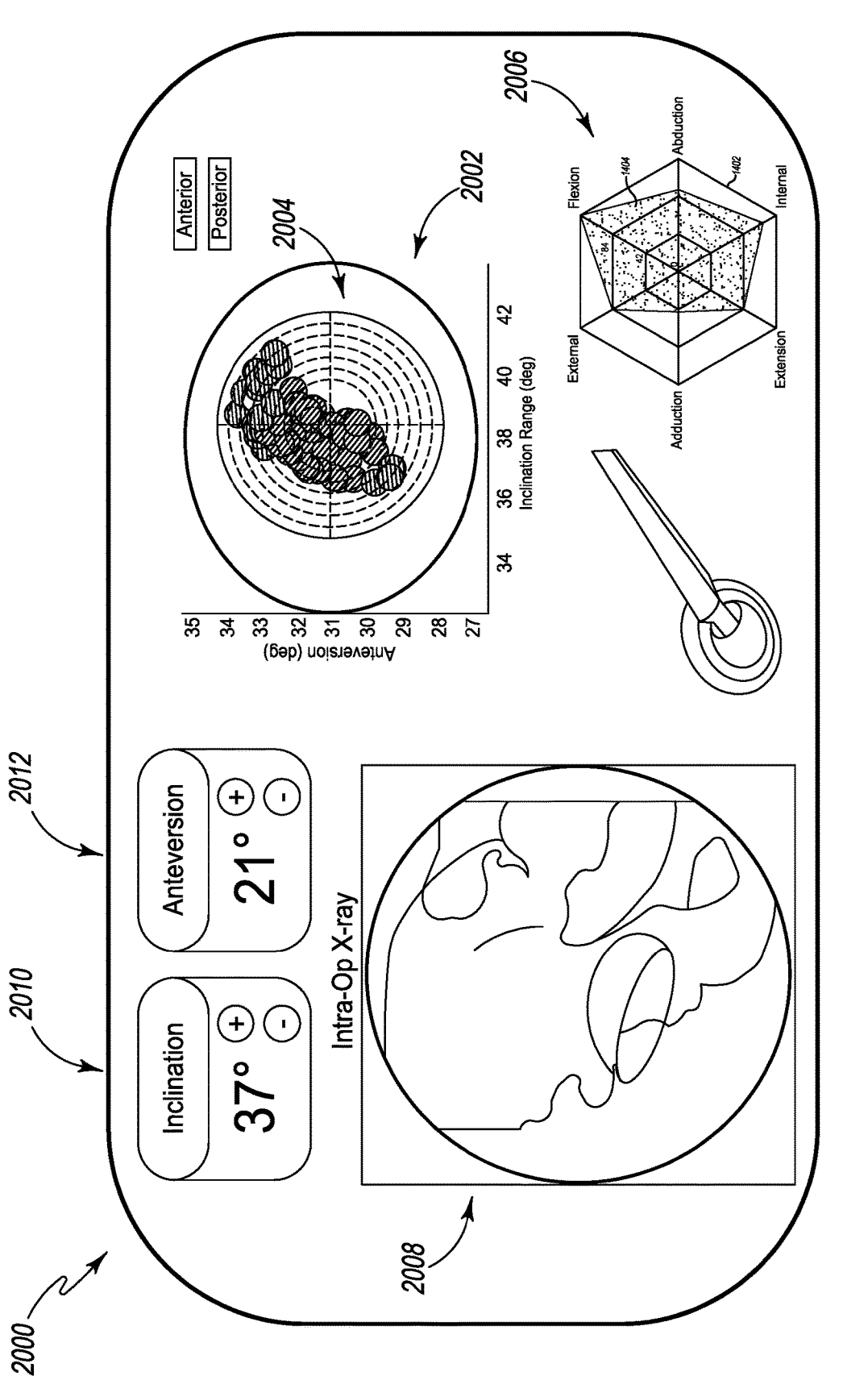
FIG. 20 is an illustrative screen image that may be displayed during the performance of the method of FIGS. 9A and 9B showing a measured orientation of the acetabular cup of the hip prosthesis of FIG. 1, a contact plot having contact indicators corresponding to contact points between the femoral prosthesis and the acetabular cup of the hip prosthesis of FIG. 1 at the measured orientation of the acetabular cup, and a graphical representation illustrating an impingement-free range of motion between the femoral prosthesis and the acetabular cup of the hip prosthesis of FIG. 1.

Furthermore, in some embodiments as shown in FIG. 20, the analysis device 402 may display the contact plot for the present orientation of the acetabular cup 104 on a graphical user interface (GUI) 200. The illustrative GUI 2000 includes a cup orientation graph 2002 on which a contact plot 2004 of the present (i.e., the measured) orientation of the acetabular cup 104 is displayed. Additionally, the GUI 2000 includes a graphical representation 2006 of the impingement-free range of motion between the femoral prosthesis 102 and the acetabular cup 104 at the present orientation. The GUI 2000 also illustratively includes a copy of the intra-operative medical image from which the present orientation of the acetabular cup 104 was determined in block 906 of FIG. 9A. Additionally, in some embodiments, the GUI 2000 may include cup orientation controls, such as an inclination control 2010 and an anteversion control 2012. In use, the orthopaedic surgeon may adjust one or both of the controls 2010, 012 to review the contact plot for a modified orientation of the acetabular cup 104. In this way, the orthopaedic surgeon can conduct a number of "what if" scenarios with regard to the orientation of the acetabular cup 104.

Referring back to FIG. 9A, after the analysis device 402 has displayed the contact plot for the present orientation of the acetabular cup 104, the method 900 advances to block 918 of FIG. 9B. In block 918, the orthopaedic surgeon continues the orthopaedic surgical procedure based on the displayed contact plot associated with the present orientation of the acetabular cup 104. For example, should the orthopaedic surgeon determine that the contact plot is satisfactory, the orthopaedic surgeon may continue the orthopaedic surgical procedure using the present orientation of the acetabular cup 104 in block 920. However, should the orthopaedic surgeon determine that the contact plot is not satisfactory, the orthopaedic surgeon may modify or adjust the present orientation of the acetabular cup 104 and continue the orthopaedic surgical procedure using a new orientation of the acetabular cup 104 in block 922. For example, in some embodiments, the orthopaedic surgeon may adjust the present orientation of the acetabular cup 104 to better match the pre-operatively planned orientation.

In either case, the method 900 advances to block 924 in which the analysis device 402 determines if the orthopaedic surgeon has completed the orthopaedic surgical procedure. If not, the method 900 loops back to block 906 in which the analysis device 402 again determines the present orientation of the acetabular cup 104, which may or may not have been adjusted by the orthopaedic surgeon in block 918. In this way, the analysis device 402 provides an opportunity to the orthopaedic surgeon to pre-plan an orientation of the acetabular cup 104 based on a predicted performance of the hip prosthesis 100 at that pre-planned orientation and to further monitor and, if desired, adjust the actual orientation of the acetabular cup 104 intra-operatively to better achieve an actual performance of the hip prosthesis 100 for the patient.

Figure 21C:
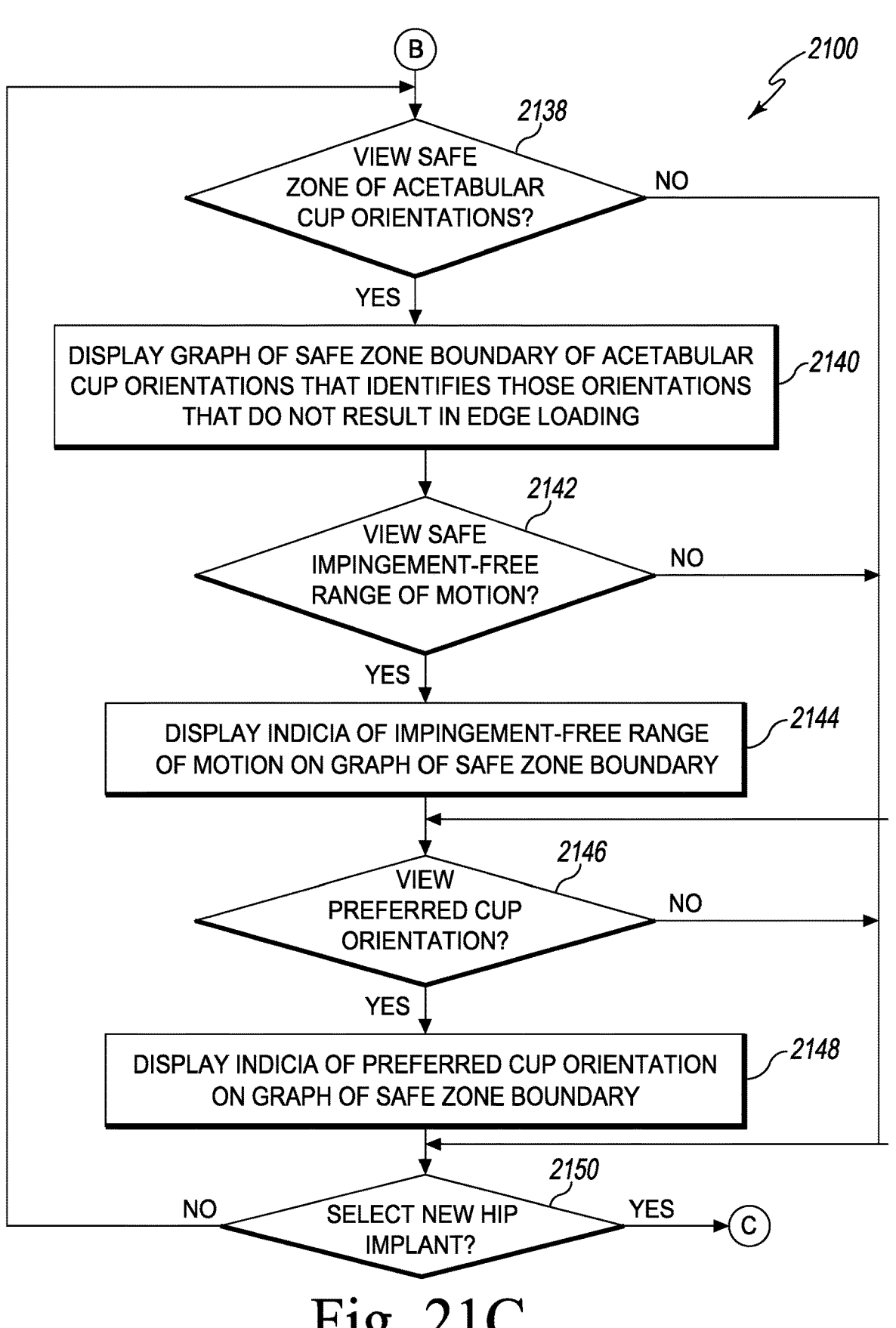

Referring now to FIGS. 21A-21C, in another embodiment, the hip prosthesis positioning analysis device 402 (and/or the positioning analysis server 502 of FIG. 5) may be configured to execute a method 2100 for determining a positioning of the hip prosthesis 100 in the boney anatomy of the patient using an activity-generic mechanics model. That is, as discussed in more detail below, the method 2100 uses a mathematical model, which is determined based on a stationary mechanics model indicative of the loading of the acetabular cup 104 by the femoral prosthesis 102 while the patient is positioned in static, functional positions, to determine a safe zone boundary of orientations of the acetabular cup 104 that do not result in edge loading of the acetabular cup 104 by the femoral prosthesis 102.

Similar to method 600 described above, the method 2100, or portions thereof, may be embodied as a set of executable instructions stored on the analysis device 402 and executable by the analysis device 402. As such, it should be appreciated that the operations of the method 2100 may be performed by one or more components of the analysis device 402 and/or devices communicatively coupled to the analysis device 402.

The method 2100 begins with block 2102 in which the analysis device 402 determines whether to analyze the positioning of the hip prosthesis 100 relative to the patient's boney anatomy (e.g., the orientation of the acetabular cup 104 relative to the patient's acetabulum 200). For example, the analysis device 402 may await instruction or input from the orthopaedic surgeon prior to begin the method 2100.

If so, the method 2100 advances to block 2104 in which the analysis device 402 acquires or receives a set of medical images of the patient's hip joint on which the orthopaedic surgery is to be performed from the imaging device 404 while the patient is positioned in static, functional positions. That is, in the illustrative embodiment, the patient is positioned in a sitting position and a standing position, which represent two "worst-case" or "boundary" positions of the patient's hip. However, in other embodiments, additional static, functional positions of the patient's hip may be used.

The medical images are embodied as images of the patient's hip joint with the hip joint positioned in various functional positions. The analysis device 402 may receive any type and number of suitable medical images that facilitate the determination of pelvic tilt measurements of the patient as discussed in more detail below. For example, as discussed above, the medical images are illustratively embodied as two-dimensional X-ray images, but may be embodied as other types of two-dimensional medical images and/or three-dimensional medical images in other embodiments.

In the illustrative embodiment, the analysis device 402 receives three different medical images including a standing anterior-posterior medical image in block 2106, a sagittal standing medical image in block 2108, and a sagittal seated-with-fully-flexed-hip medical image in block 2110. As discussed above in regard to method 600, the anterior-posterior medical image may be embodied as a medical image of the patient's hip joint taken from a coronal plane anterior to the patient while the patient is standing. Additionally, the sagittal standing medical image may be embodied as a medical image of the patient's hip joint taken from a sagittal plane of the patient while the patient is standing.

After the analysis device 402 acquires the medical images in block 2104 of FIG. 21A, the analysis device 402 determines a pelvic mobility of the patient based on the received medical images in block 2112. As discussed above, the pelvic mobility is indicative of a range of motion of the patient's pelvis and is determined based on pelvic tilt measurements of the patient. As such, the analysis device 402 initially determines the pelvic tilt measurements of the patient's hip from the medical images. To do so, in block 2114, the analysis device 402 may identify particular ana-tomical landmarks of the patient's boney anatomy. In particular, the analysis device 402 identifies anatomical landmarks on the patient's relevant femur and acetabulum 200. Again, the anatomical landmarks may be embodied as any anatomical landmark that facilitates or improves the determination of the pelvic tilt measurements of the patient. The particular landmarks used may depend on various factors such as the patient's bony anatomy, the size and type of hip prosthesis 100, and/or other factors. For example, in the illustrative embodiment, the identified anatomical landmarks includes the medial and lateral anterior superior iliac spine, the pubic symphysis, the center of the hip joint, and the mid-point of the femoral shaft of the relevant femur. Similar to block 618 and 620 of method 600 discussed above, the analysis device 402 may identify the relevant anatomical landmarks based on manually annotated medical images received from the orthopaedic surgeon in block 2116 and/or may be configured to automatically and/or autonomously identify the anatomical landmarks on the patient's bony anatomy in the medical image(s) in block 2118.

After the anatomical landmarks have been identified, in block 2120, the analysis device 402 calculates the pelvic tilt measurements of the patient's hip based on the identified landmarks and using the medical images received in block 2104 as discussed above in regard to block 626 of method 600. Additionally, after the analysis device 402 has determined the various pelvic tilt measurements in block 2120, the analysis device 402 determines the patient's pelvic mobility based on the pelvic tilt measurements in block 2122 as discussed above in regard to block 628 of method 600.

Subsequently, in block 2124 of FIG. 21B, the analysis device 402 determines the type and size of the femoral prosthesis 102 and the acetabular cup 104 of the hip prosthesis 100 that is to be implanted into the patient. For example, the orthopaedic surgeon may select the type and size from a menu of available types and sizes or otherwise provide those selections to the analysis device 402.

In block 2126, the analysis device 402 determines a safe zone boundary that defines those orientations of the acetabular cup 104, relative to the acetabulum of the patient shown in the set of medical images, that do not result in edge loading of the cup liner 122 of the acetabular cup 104 by the femoral head 118 of the femoral prosthesis 102. To do so, in block 2128, the analysis device 402 determines the safe zone boundary based on loading of the acetabular cup 104 by the femoral prosthesis 102 while the patient is positioned in each of the functional positions (e.g., standing and sitting). As discussed above, the "loading" of the acetabular cup may be determined based on, or otherwise identified by, a set of contact points on the cup liner 122 of the acetabular cup 104 by the femoral head 118 of the femoral prosthesis 102 at each of the function positions of the patient (e.g., standing and sitting). As such, the safe zone boundary identifies those orientations of the acetabular cup 104 at which the corresponding set of contact points on the cup liner 122 do not contact, or otherwise occur on, the edge of the acetabular cup 104 (or within a reference distance of the edge of the acetabular cup 104).

In the illustrative embodiment, as shown in block 2130, the analysis device 402 utilizes a mathematical model indicative of the contact points between the femoral head 118 of the femoral prosthesis 102 and the cup liner 122 of the acetabular cup 104 for a range of orientations of the acetabular cup 104 relative to the acetabulum of the patient. As discussed above in regard to the method 800 of FIGS. 8A and 8B, the mathematical model used in block 2130 may be embodied as any type of mathematical model that has been trained or otherwise designed to model the output of a stationary mechanics model that is indicative of the loading (i.e., the set(s) of contact points) of the acetabular cup 104 by the femoral prosthesis 102 while the patient is positioned in each of the functional positions (e.g., standing and sitting).

To facilitate the use of the mathematical model of block 2130, the analysis device 402 may be configured to generate the mathematical model prior to execution of the method 2100. To do so, the analysis device 402 may execute a method 2200 for generating a mathematical model indicative of loading of the acetabular cup 104 by the femoral prosthesis 102 at each functional position of the patient using a stationary mechanics model. The method 2200 is similar to the method 800 described above and includes the determination of a global pool of sets of contact points between the femoral prosthesis 102 and the acetabular cup 104 for a range of varying inputs, such as a range of pelvic tilt values and acetabular cup orientations. In this way, a "universe" of sets of contact points is generated for a large number of combinations of inputs, and that "universe" of sets of contact points is then used to generate the mathematical model.

The method 2200 begins with block 2202 in which the analysis device 402 determines the granularity of various inputs to the stationary mechanics model. For example, in block 2204, the granularity of the pelvic tilt values and, thereby, the granularity of the pelvic mobility values are determined. Additionally, in block 2206 the granularity of the orientation of the acetabular cup 104 is determined. For example, as discussed above in regard to method 800, the granularity of the degree of inclination and anteversion of the acetabular cup 104 may be determined. Again, it should be appreciated that the granularities of the pelvic tilt values and the acetabular cup orientation define the amount at which each of those values are adjusted per iteration of the stationary mechanics model. As such, it should be appreciated that the granularity of the pelvic tilt values and the acetabular cup orientation adjusts the resolution of the output of the resulting mathematical model, which may define the overall performance of the mathematical model. The granularities may be selected by the orthopaedic surgeon or may be "hard coded" or otherwise preselected.

Subsequently in block 2208, initial patient tilt values and an initial orientation of the acetabular cup 104 is determined or chosen. Such initial values may be pre-selected or pre-determined or may be selected by the orthopaedic surgeon or other user of the analysis device 402. Regardless, the method 2200 subsequently advances to block 2210 in which the analysis device 402 determines the set of contact points between the femoral head 118 of the femoral prosthesis 102 and the cup liner 122 of the acetabular cup 104 using the stationary mechanics model with the selected pelvic title values, associated pelvic mobility value, the selected size and type of the hip prosthesis 100, and the selected orientation of the acetabular cup 104 as inputs to the stationary mechanics model. To do so, in block 2212, the analysis device 402 determines a sub-set of contact points between the femoral prosthesis 102 and the acetabular cup 104 for each static, functional position of the patient (e.g., standing and sitting). The sub-set of contact points may include a single contact point or a group of contact points for the corresponding static, functional position of the patient at the selected orientation of the acetabular cup 104 and pelvic title values. Regardless, in block 2214, the analysis device 402 generates the final set of contact points for the selected orientation of the acetabular cup 104 based on the individual sub-sets of the contact points of each static, functional position.

As discussed above and similar to the ADL mechanics model discussed above, the stationary mechanics model may be embodied as any type of model capable of generating data indicative of the loading (i.e., the set(s) of contact points) of the acetabular cup 104 by the femoral prosthesis 102 while the patient is positioned in each of the functional positions (e.g., standing and sitting). For example, the stationary mechanics model may be embodied as a mathematical equation or set of equations having inputs (e.g., the pelvic tilt measurements, the type and size of the femoral prosthesis 102 and the acetabular cup 104, and the range of orientations of the acetabular cup 104) that define coefficients of the mathematical equation(s). In the illustrative embodiment, for example, the stationary mechanics model is based on the Hertzian contact model for sphere-on-sphere contact and enables calculations of contact area and contact stress between the femoral head 118 of the femoral prosthesis 102 and the cup liner 122 of the acetabular cup 104. In doing so, the stationary mechanics model may use, or otherwise rely on, on several mathematical equations including:

$$a = \sqrt[3]{\frac{3F\left[\dfrac{1-v_1^2}{E_1} + \dfrac{1-v_2^2}{E_2}\right]}{4\left(\dfrac{1}{R_1} + \dfrac{1}{R_2}\right)}} \qquad \text{Equation (1)}$$

$$P_{max} = \frac{3F}{2\pi a^2} \qquad \text{Equation (2)}$$

In equation (1), the contact area, a, between the femoral head 118 of the femoral prosthesis 102 and the cup liner 122 of the acetabular cup 104 can be solved in which R1 is the radius of the "sphere" of the femoral head 118, R2 is the radius of the "sphere" of the cup liner 122, E1 is the moduli elasticity of the "sphere" of the femoral head 118, E2 is the moduli elasticity of the "sphere" of the cup liner 122, v1 and v2 are the Poisson's ratios, and F is the applied force. Similarly, in equation (2), the maximum contact pressure, Pmax, using the same variables as equation (1) defined above. It should be appreciated that modifications to equations (1) and (2) may be modified and/or other equations used in the stationary mechanics model to the loading (i.e., the set(s) of contact points) of the acetabular cup 104 by the femoral prosthesis 102.

In block 2216, the analysis device 402 stores the set of contact points generated in block 2210. For example, the analysis device 402 may store the set of contact points in the data storage 412. In some embodiments, as discussed above in regard to method 800, the analysis device 402 may store the generated sets of contact points as a function of the particular patient tilt values and cup orientation used as input to the stationary mechanics model to generate the corresponding set of contact points.

Figure 22B:
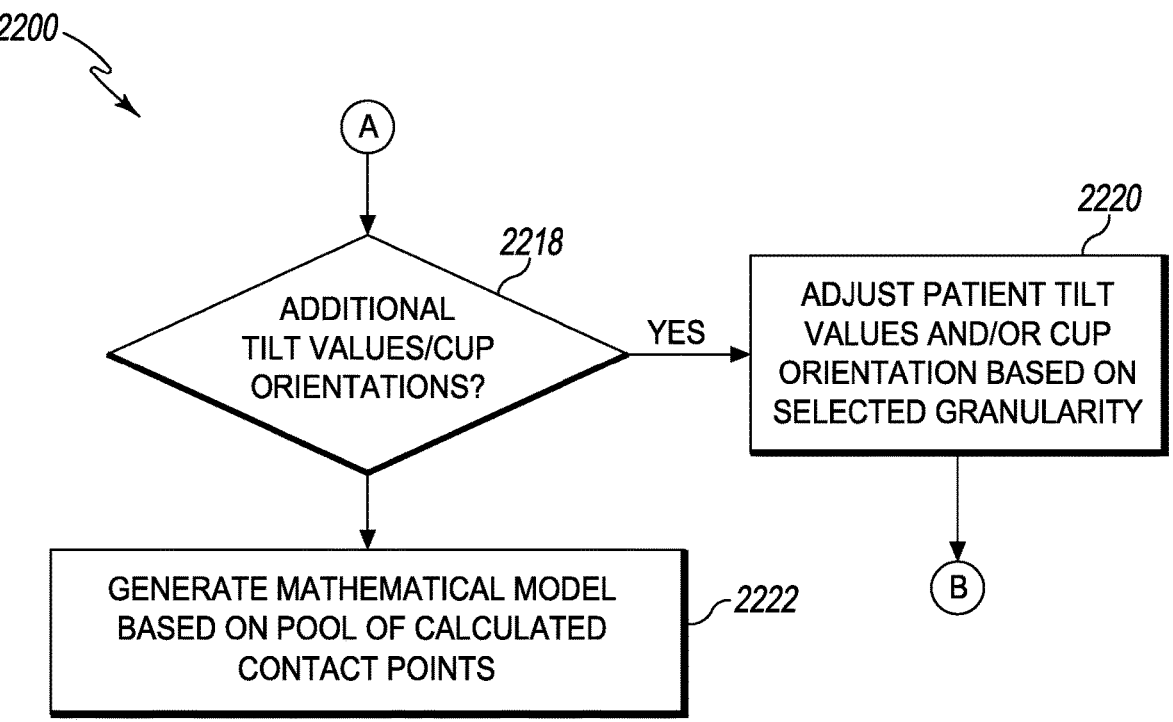

Subsequently, in block 2218 of FIG. 22B, the analysis device 402 determines whether an additional set of contact points are to be generated for a new combination of pelvic tilt and/or acetabular cup orientation values. If so, the method 2200 advances to block 2218, in which the analysis device 402 adjusts one or more of the pelvic tilt values and/or one or more of the acetabular cup orientation values (e.g., the inclination value and/or the anteversion value). The analysis device 402 adjusts those values based on the granularity of inputs determined in block 2202, and the method 2200 subsequently loops back to 2210 of FIG. 22A to calculate a set of contact points using the adjusted pelvic tilt value(s) and/or acetabular cup orientation value(s). In this way, the analysis device 402 steps through a range of different pelvic tilt values and acetabular cup orientation values combinations such that the final sets of contact points cover a "universe" of different possible combinations.

Similar to the ADL mechanics model described above, it should be appreciated that the stationary mechanics model has been described as iteratively calculating the sets of contact points for each combination of pelvic tilt and acetabular cup orientation values. However, in other embodiments, the stationary mechanics model may be designed or formulated such that the complete "universe" of different possible pelvic tilt and orientation values is determined as a single calculation or equation.

Referring back to block 2218, after the set of contact points for each combination of pelvic tilt values and acetabular cup orientation values has been determined, the method 2200 advances to block 2222. In block 2222, the analysis device 402 generates a mathematical model based on the pool of sets of contact points generated in block 2210. As discussed above, the mathematical model is a model of the generated sets of contact points, which are the result of the "universe" of pelvic tilt and acetabular cup orientation values. As such, using the measured pelvic tilt measurements of a particular patient, the mathematical model is capable of generating the corresponding group of sets of contact points between the femoral prosthesis 102 and the acetabular cup 104 for the complete range of orientations of the acetabular cup 104 of interest and for each of the static, functional positions of the patient (e.g., standing and sitting). Because such individual calculations have already been completed, it should be appreciated that the mathematical model may perform faster than the stationary mechanics model in the generation of the resultant sets of contact points for that particular patient. For example, mathematical model may produce the resultant set of contact points in less than five minutes, in less than three minutes, in less than one minute, in less than thirty seconds, in less than one second, and/or in less than one millisecond in some embodiments.

As discussed above, the mathematical model generated in block 2222 may be embodied as any type of mathematical model capable of generating the sets of contact points using the patient's pelvic tilt measurements as an input. For example, to generate the mathematical model, the analysis device 402 may perform any one or more of the techniques described in the journal article entitled "Development Of A Statistical Shape-Function Model Of the Implanted Knee For Real-Time Prediction Of Joint Mechanics" by Gibbons et al. (Gibbons K. et al. Development Of A Statistical Shape-Function Model Of the Implanted Knee For Real-Time Prediction Of Joint Mechanics, *Journal of Biomechanics* 2019; 88:55-63), the entirety of which is incorporated herein by reference.

As discussed above, the mathematical model be embodied as a linear response model, a response surface model, a neural network model, and/or a statistical fitting model based on the generated sets of contact points. Additionally, as discussed above, the investigated range of cup orientations is "hard-coded" into the mathematical model and, as such, the illustrative mathematical model is configured to generate a pool of sets of contact points for the patient in a single calculation, rather than an iterative approach. In other embodiments, the generated mathematical model may be designed to utilize an iterative approach with regard to the range of acetabular cup orientations.

After the mathematical model has been generated in block 2222, the mathematical model may be subsequently used in the determination of the safe zone boundary in block 2130 of method 2100 of FIG. 21B. To do so, the analysis device 402 may execute a method 2300 for determining the safe zone boundary using the generated mathematical model as shown in FIG. 23. The method 2300 begins with block 2302 in which the patient tilt measurements determined in block 2120 (and/or the pelvic mobility determined in block 2122) are used as inputs to the mathematical model, which produces a set of contact points between the femoral head 118 of the femoral prosthesis 102 and the cup liner 122 of the acetabular cup 104. Again, as discussed above, the set of contact points generated by the mathematical model in block 2302 includes contact points for the range of orientations of the acetabular cup 104 and for each static, functional position of the patient (e.g., sitting and standing).

Subsequently, in block 2304, the analysis device 402 determines or otherwise identifies the subset of "acceptable" orientations of the acetabular cup 104 (i.e., those cup orientations that do not result in edge loading of the cup liner 122 of the acetabular cup 104). To do so, in block 2306, the analysis device 402 initially determines the subset of orientations of the acetabular cup 104 that do result in edge loading. That is, the analysis device 402 determines whether any contact point of the set of contact points determined via the mathematical model in block 2302 results in edge loading. In the illustrative embodiment, as discussed above in regard to FIG. 13, the analysis device 402 may determine the subset of orientations of the acetabular cup 104 that result in edge loading based on the distance of each contact point of the corresponding set of contact points relative to the edge of the cup liner 122.

Again, as discussed above, the reference threshold distance from the inner (distal) edge of the cup liner 122 for a contact point to be considered an "edge loading contact point," and the corresponding orientation of the acetabular cup 104 to result in edge loading, may be fixed or identical across sizes of the acetabular cup 104 or may be relative to the size of the acetabular cup 104. For example, in an illustrative embodiment, the analysis device 402 may determine that a contact point is an "edge loading contact point" if that contact point is within an arc length of 1.5 millimeters or less of the inner (distal) edge of the cup liner 122 (indicated as edge boundary 1312 in FIG. 13). In another embodiment, the analysis device 402 may determine that a contact point is an "edge loading contact point" if that contact point is within an arc length of 1.0 millimeters or less of the inner (distal) edge of the cup liner 122. In a further embodiment, the analysis device 402 may determine that a contact point is an "edge loading contact point" if that contact point is within an arc length of 0.5 millimeters or less of the inner (distal) edge of the cup liner 122. Additionally or alternatively, in other embodiments, the reference distance for a contact point to be considered an "edge loading contact point" may be relative to the size of the acetabular cup 104. For example, the reference distance from the inner (distal) edge of the cup liner 122 to consider a contact point as edge loading may be selected such that a ratio of the distance from the inner (distal) edge of cup liner 122 to the inner diameter of cup liner 122 is in the range of 0.034 to 0.067, in the range of 0.044 to 0.0577, or about 0.047. Regardless, it should be appreciated that by increasing the reference distance, the confidence of the identification of all contact points that result in edge loading of the acetabular cup 104 may be increased.

In other embodiments, however, other methodologies may be used to determine those contact points resulting in edge loading. Regardless, if any contact points are determined to result in edge loading, the analysis device 402 identifies the orientations of the acetabular cup 104 associated with those edge-loading contact points as cup orientations that result in edge loading of the acetabular cup 104.

Subsequently, in block 2308, the analysis device 402 determines the subset of orientations of the acetabular cup 104 that do not result in edge loading of the cup liner 122 of the acetabular cup 104 based on the identified cup orientations of block 2306. That is, the analysis device 402 may identify all other cup orientations, except those identified in block 2306, as "acceptable" cup orientations that do not result in edge loading in block 2308.

After the analysis device 402 has identified the "acceptable" cup orientations (i.e., those that do not result in edge loading of the acetabular cup 104) in block 2304, the analysis device 402 may identify one or more preferred orientations of the acetabular cup 104 from the "acceptable" cup orientations in block 2310, in some embodiments. As discussed above, it should be appreciated that the preferred cup orientation(s) may or may not be the "optimized" cup orientation depending on the selection criteria. To do so, the analysis device 402 may utilize any suitable methodology for identifying the preferred cup orientation(s) such as those described above in regard to block 652 of method 600 of FIG. 6.

After the analysis device 402 has determined the set of acceptable acetabular cup orientations in block 2304 and the preferred acetabular cup orientation(s) in block 2310, the method 2300 advances to block 2312. In block 2312, the analysis device 402 determines an edge loading boundary of orientation values that result in edge loading of the acetabular cup 104 based on the set of acetabular cup orientations that were determined to result in edge loading in block 2306. That is, as discussed above in regard to edge loading boundary 1606 of FIG. 16, the analysis device 402 generates a boundary defining acetabular cup orientations (i.e., degrees of inclination and anteversion) outside of which results in edge loading of the acetabular cup 104. Again, it should be appreciated that the edge loading boundary 1606, when initially determined based on the defined edge-loading cup orientations, may have a "noisy" or erratic shape depending on the location of those edge-loading cup orientations. As such, the analysis device 402 may employee some amount of data smoothing, such as spline fitting, to generate the final shape of the edge loading boundary. Additionally, it should be appreciated that the edge loading boundary may or may not be a simplistic geometrical shape. For example, as described in more detail below in regard to FIG. 29, the edge loading boundary (and safe zone boundary) may an irregular shape.

Subsequently, in block 2314, the analysis device 402 determines the safe zone boundary based on the edge loading boundary determined in block 2312. In some embodiments, the safe zone boundary is set to be identical to the edge loading boundary (i.e., each may have congruent boundaries with each other). However, in other embodiments, the safe zone boundary may be a reduction of the edge loading boundary. That is, the safe zone boundary may be internally offset from the edge loading boundary so as to provide an additional amount of tolerance in acetabular cup orientations.

Referring now back to block 2126 of FIG. 21B, after the analysis device 402 has determined the safe zone boundary, the method 2100 advances to block 2132 in which the analysis device 402 determines the impingement-free range of motion between the femoral prosthesis 102 (e.g., the femoral neck 114 of the stem 110 of the femoral prosthesis 102) and the cup liner 122 of the acetabular cup 104. To do so, in the illustrative embodiment in block 2134, the analysis device 402 determines the femoral prosthesis impingement-free range of motion based on three-dimensional models of the type and size of the acetabular cup 104 and the femoral prosthesis 102 determined in block 2124.

Similar to the analysis of the contact points between the femoral head 118 of the femoral prosthesis 102 and the cup liner 122 of the acetabular cup 104 discussed above, it should be appreciated that the "run-time" analysis of the impingement-free range of motion between the femoral prosthesis 102 and the acetabular cup 104 based on three-dimensional models of the particular protheses may be time intensive. As such, in the illustrative embodiment as shown in block 2136, the analysis device 402 utilizes a mathematical model indicative of the impingement-free range of motion between femoral neck 114 of the femoral prosthesis and the cup liner 122 of the acetabular cup 104 for each static, functional position of the patient (e.g., standing and sitting). The mathematical model used in block 2136 may be embodied as any type of mathematical model that has been trained or otherwise designed to model the impingement-free range of motion of the three-dimensional models corresponding to the selected type and size of the femoral prosthesis 102 and the acetabular cup 104 (as well as other hip prosthesis as discuss ed below) while the patient is positioned in each of the functional positions.

To facilitate the use of the mathematical model of block 2136, the analysis device 402 may be configured to generate the mathematical model prior to execution of the method 2100. To do so, the analysis device 402 may execute a method 2400 for generating a mathematical model indicative of the impingement-free range of motion between the femoral prosthesis 102 and the acetabular cup 104 at each functional position of the patient using three-dimensional models of hip prostheses. As described in detail below, the method 2400 includes the determination of the impingement-free range of motion of global pool of hip prostheses for a range of varying inputs, including a range of different orientations of the acetabular cup 104 and geometric measurements of the analyzed hip prosthesis (which correlates to or otherwise estimates the various types and sizes of hip protheses). In this way, the impingement-free range of motion can be determined for a range of different hip prostheses and acetabular cup orientations.

The method 2400 begins with block 2204 in which the analysis device 402 may obtain three-dimensional models of the set of hip prostheses for which the impingement-free range of motion is to be investigated. It should be appreciated, however, that such a set of three-dimensional models may be overly large and burdensome. As such, in the illustrative embodiments, a three-dimensional model of an initial hip prosthesis may be obtained in block 2402, which is then modified to simulate hip prostheses of different types and sizes by adjusting various geometric measurements of the hip prosthesis as discussed below.

In block 2404, the analysis device 402 determines the set of geometric measurements of the hip prostheses to be used as input to the mathematical model. As discussed above, the geometric measurements may be used in some embodiments of method 2400 to adjust the initial three-dimensional model of the hip prosthesis to simulate hip prostheses of different types and sizes. In the illustrative embodiment, the geometric measurements include an inner diameter measurement of the acetabular cup (e.g., an inner diameter measurement of the cup liner), an outer diameter measurement of the acetabular cup, a proximal-distal distance measurement from the medial edge of the cup liner of the acetabular cup to the center of rotation of the femoral head of the femoral prosthesis, a proximal-distal distance measurement from the lateral edge of the cup liner of the acetabular cup to the center of rotation of the femoral head of the femoral prosthesis, and the neck angle of the femoral stem of the femoral prosthesis (e.g., relative to the longitudinal angle of the stem). It should be appreciated that the inner and outer diameters of the acetabular cup provides an estimation of the size of the acetabular cup and femoral prosthesis, and the proximal-distal distance measurements provide an estimation of the type of acetabular cup (e.g., lipped or "augmented" versus non-lipped). The geometric measurements to be used as inputs may be pre-selected (e.g., "hard coded") or selected by a user during the execution of the method 2400.

In embodiments in which three-dimensional models of each hip prostheses to be analyzed is obtained in block 2402, the analysis device 402 may analyze each of the three-dimensional models in block 2406 to determine the actual geometric measurements of those hip prostheses, rather than adjusting the geometric measurements of an initial three-dimensional model to simulate or estimate the different types and sizes of hip prostheses as in the illustrative embodiment. In such embodiments, the analysis device 402 may store the determined geometric measurements in block 2408. For example, the analysis device 402 may store the set of determined geometric measurements in the data storage 412.

After input geometric measurements have been determined or selected in block 2404, the method 2400 advances to block 2410 in which the analysis device 402 determines the granularity of various input parameters to the mathematical model. For example, in block 2412, the granularity of the orientation of the acetabular cup 104 is determined. As discussed above, the granularity of the degree of inclination and anteversion of the acetabular cup 104 may be determined. Additionally, in block 2414, the granularity of the stem version of the femoral stem of the femoral prosthesis is determined. Further, in block 2416, the granularity of the geometric measurements determined in block 2404 is determined. In doing so, each geometric measurement may have the same or different granularity relative to each other. Again, it should be appreciated that the granularities of the acetabular cup orientation, the stem version, and the geometric measurements define the amount at which each of those values are adjusted per iteration of the impingement-free range of motion analysis. As such, it should be appreciated that the determined granularities adjust the resolution of the output of the resulting mathematical model, which may define the overall performance of the mathematical model. The granularities may be selected by the orthopaedic surgeon/user or may be "hard coded" or otherwise preselected.

Figure 24A:
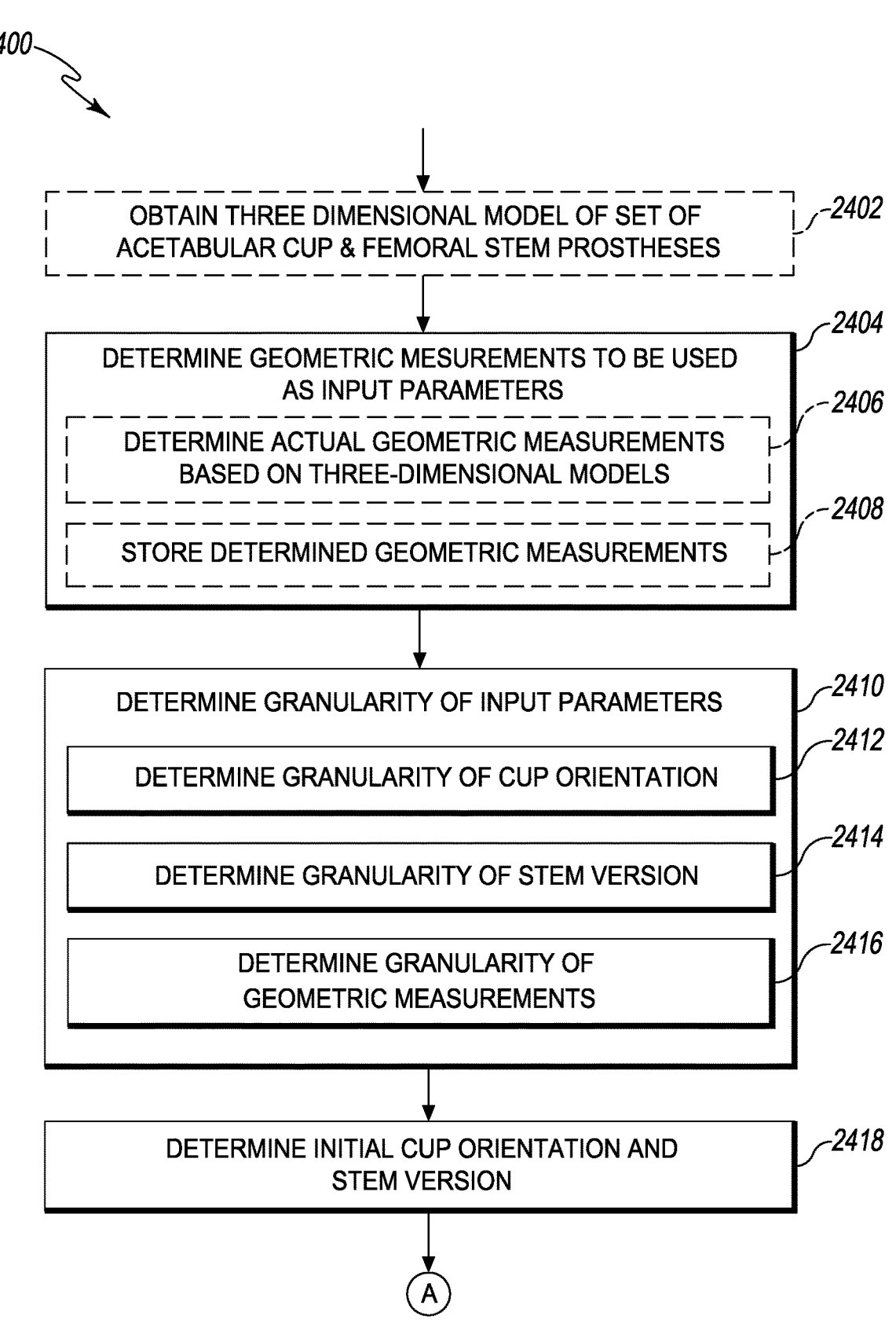
FIG. 24A-24B are flow chart diagrams of an embodiment of a method for generating a mathematical model indicative of an impingement-free range of motion of a femoral stem of the femoral prosthesis of the hip prosthesis of FIG. 1.
Figure 24B:
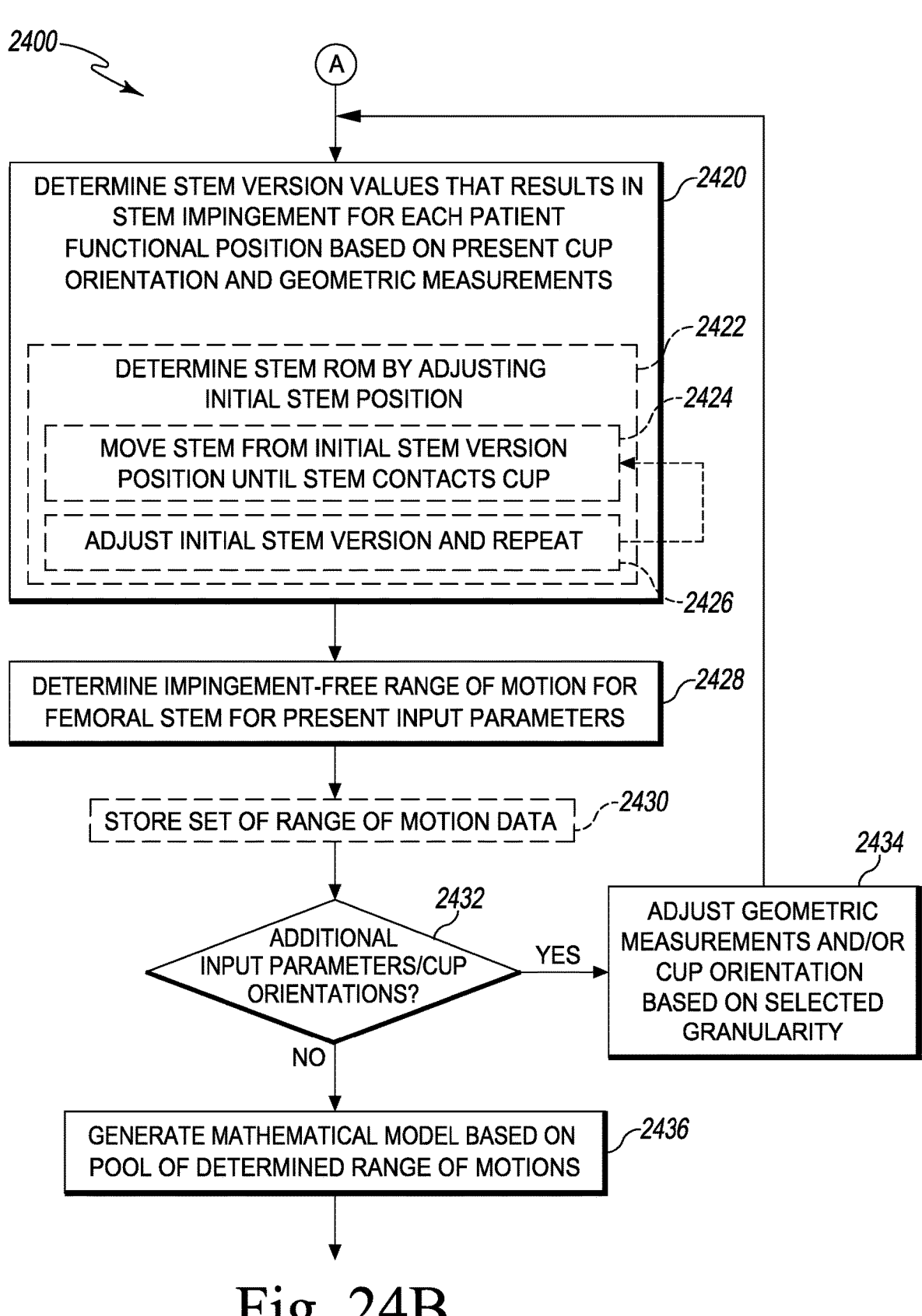

Subsequently in block 2418, an initial orientation of the acetabular cup and stem version is determined or chosen. Such initial values may be pre-selected or pre-determined or may be selected by the orthopaedic surgeon or other user of the analysis device 402. Regardless, the method 2400 subsequently advances to block 2420 of FIG. 24B in which the analysis device 402 determines a set of stem version values that result in stem impingement of the stem of the femoral prosthesis on the edge of the acetabular cup for each functional position of the patient (e.g., standing and sitting) based on the present cup orientation and geometric measurements.

To do so, in the illustrative embodiment, the analysis device 402 analyzes the range of motion of the three-dimensional model of the hip prosthesis having the present geometric measurements, which may be an original three-dimensional model of the corresponding physical hip prosthesis or a three-dimensional model that has been modified or morphed based on the present geometric measurements to simulate a hip prosthesis having the present geometric measurements. In doing so, the analysis device 402 may utilize any methodology to analyze and determine the impingement-free range of motion of the three-dimensional model. For example, the analysis device 402 may perform any one or more of the techniques described in the journal article entitled "Effect Of Intraoperative Treatment Options On Hip Join Stability Following Total Hip Arthroplasty" by Myers et al. (Myers C. et al. Effect of Intraoperative Treatment Options on Hip Join Stability Following Total Hip Arthroplasty, *Journal of Orthopaedic Research* 2021; 1-10) and/or the journal article entitled "Impingement In Total Hip Replacement: Mechanisms and Consequences" by Brown et al. (Brown T. et al. Impingement In Total Hip Replacement: Mechanisms and Consequences, *Current Orthopaedics* 2008; 22:376-391), the entirety of both of which is incorporated herein by reference.

In the illustrative embodiment, in block 2422, the analysis device 402 may determine the impingement-free range of motion of the femoral stem by adjusting the initial stem version position of the femoral stem. To do so, in block 2424, the analysis device 402 may move the three-dimensional model of the femoral prosthesis of the analyzed hip prosthesis from an initial stem version position to a final stem version position at which the femoral stem of the three-dimensional model of the femoral prosthesis contacts the three-dimensional model of the acetabular cup (e.g., contacts a rim of the cup liner) having the present cup orientation. In this way, the analysis device 402 determines the range of stem version values that do result in impingement for the present orientation of the acetabular cup.

Figure 28:
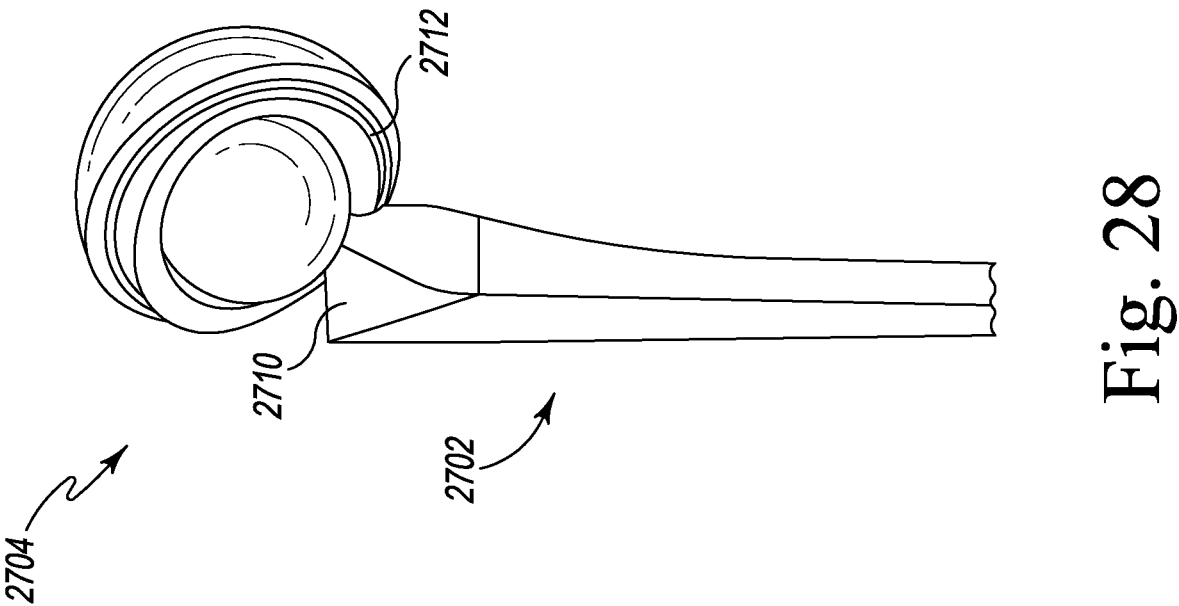
FIG. 28 is a simplified model of the acetabular cup and femoral prosthesis of the hip prosthesis of FIG. 27 with the femoral stem of the femoral prosthesis moved to a final stem version position in which the neck of the femoral stem is in contact with the cup liner of the acetabular cup of the hip prosthesis of FIG. 1.
Figure 27:
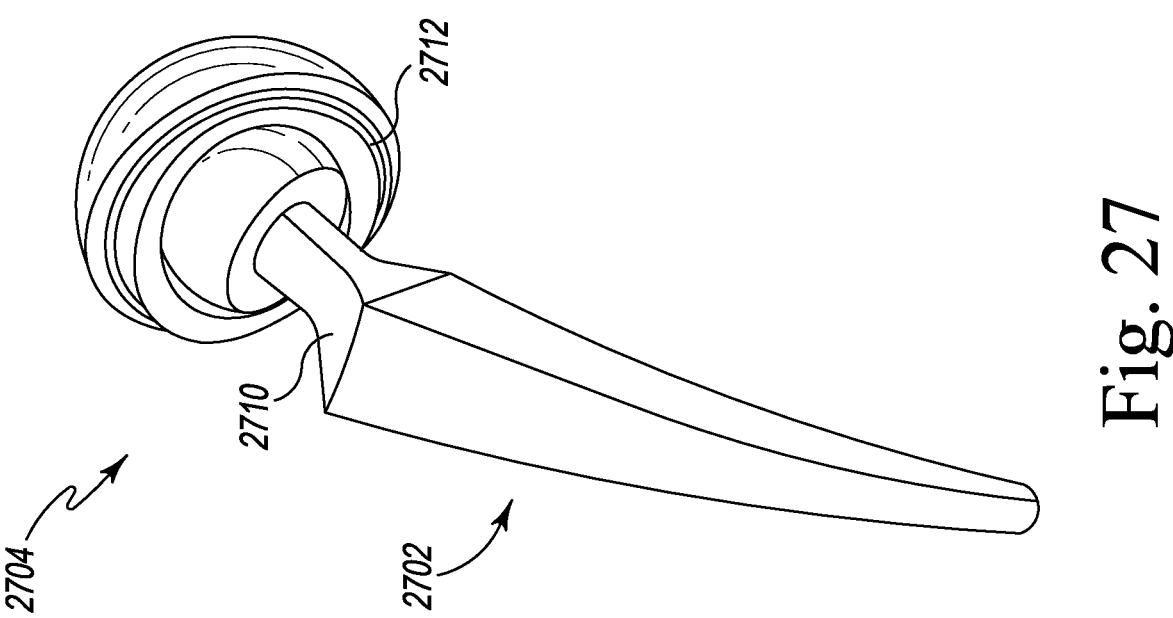
FIG. 27 is a simplified model of the acetabular cup and femoral prosthesis of the hip prosthesis of FIG. 1 with the femoral stem of the femoral prosthesis positioned in an initial stem version position in which a neck of the femoral stem is not in contact with the cup liner of the acetabular cup of the hip prosthesis of FIG. 1.

For example, as shown in FIG. 27, a three-dimensional model 2702 of a femoral prosthesis having the present geometric measurements (e.g., the present neck angle) is positioned in an initial stem version position at which a neck 2710 of the three-dimensional model 2702 of the femoral prosthesis is not in contact with a lip or rim 2712 of a three-dimensional model 2704 of an acetabular cup having the present geometric measurements (e.g., the present inner and outer diameters and proximal-distal distance measurements from the medial and lateral edges of the cup liner of the acetabular cup to the center of rotation of the femoral head of the femoral prosthesis). As shown in FIG. 28, the three-dimensional model 2702 of a femoral prosthesis is subsequently moved by changing its version to a final stem version position at which the neck 2710 of the three-dimensional model 2702 of the femoral prosthesis has contacted the lip or rim 2712 of the three-dimensional model 2704 of an acetabular cup. Again, in this way, the analysis device 402 determines the range of stem version values that do result in impingement for the present orientation of the acetabular cup. Referring back to block 2424 of FIG. 24B, once the femoral stem of the three-dimensional model is so positioned, the analysis device 402 adjusts the initial stem version position of the femoral stem of the three-dimensional model of the femoral prosthesis in block 2426 and repeats block 2424 to thereby determine a range of stem version values that do result in impingement for a particular acetabular cup orientation.

Once the impingement-free range of motion is determined for the set of stem version values that result in stem impingement for each functional position of the patient (e.g., standing and sitting) based on the present cup orientation and geometric measurements, the method 2400 advances to block 2428. In block 2428, the analysis device 402 determines the impingement-free range of motion based for the present input parameters (e.g., cup orientation and geometric measurements) based on those stem version values determined to result in stem impingement in block 2420. Additionally, in some embodiments, the analysis device 402 may store determined impingement-free range of motion in block 2430. For example, the analysis device 402 may store the set of contact points in the data storage 412.

Subsequently, in block 2432, the analysis device 402 determines whether an additional impingement-free range of motion is to be determined for a new combination of geometric measurements and/or orientation values. If so, the method 2400 advances to block 2434, in which the analysis device 402 adjusts one or more of the geometric measurements (e.g., the inner cup diameter, the outer cup diameter, the proximal-distal distance measurements from the medial and lateral edges of the cup liner, and/or the neck angle) and/or one or more of the acetabular cup orientation values (e.g., the inclination value and/or the anteversion value). The analysis device 402 adjusts those values based on the granularity of inputs determined in block 2410, and the method 2400 subsequently loops back to 2420 to determine a set of stem version values that result in stem impingement for each functional position of the patient (e.g., standing and sitting) based on the updated cup orientation and/or geometric measurements. In this way, the analysis device 402 steps through a range of different geometric measurements (which approximates a range of different types and sizes of hip prostheses) and acetabular cup orientation values combinations such that the final sets of impingement-free range of motion cover a "universe" of different possible combinations.

Referring back to block 2432, after the impingement-free range of motion has been determined for each combination of geometric measurements and acetabular cup orientation values, the method 2400 advances to block 2436. In block 2436, the analysis device 402 generates a mathematical model based on the pool of impingement-free ranges of motion generated in block 2438. As discussed above, the mathematical model is a model of an impingement-free range of motion of a range of hip prostheses implanted at a range of acetabular cup orientation values while the patient is positioned in each of the stationary, functional positions (e.g., sitting and standing). In the illustrative embodiment, because the impingement-free range of motion for the family of hip prostheses (as defined by the range of geometric measurements) across the range of acetabular cup orientations has been determined, the mathematical model may perform faster than "run-time" evaluation of three-dimensional models of a particular hip prostheses. Similar to the mathematical model generated in block 2222 of method 2200, the mathematical model of block 2436 may be embodied as any type of mathematical model capable of generating data indicative of an impingement-free range of motion using geometric measurements of a hip prosthesis as an input. For example, as discussed above, the mathematical model be embodied as a linear response model, a response surface model, a neural network model, and/or a statistical fitting model based on the generated sets of contact points. Additionally, as discussed above, the investigated range of cup orientations is "hard-coded" into the mathematical model and, as such, the illustrative mathematical model is configured to generate a pool of impingement-free range of motion values for the patient in a single calculation, rather than an iterative approach. Of course, in other embodiments, the generated mathematical model may be designed to utilize an iterative approach with regard to the range of acetabular cup orientations.

Figure 25:
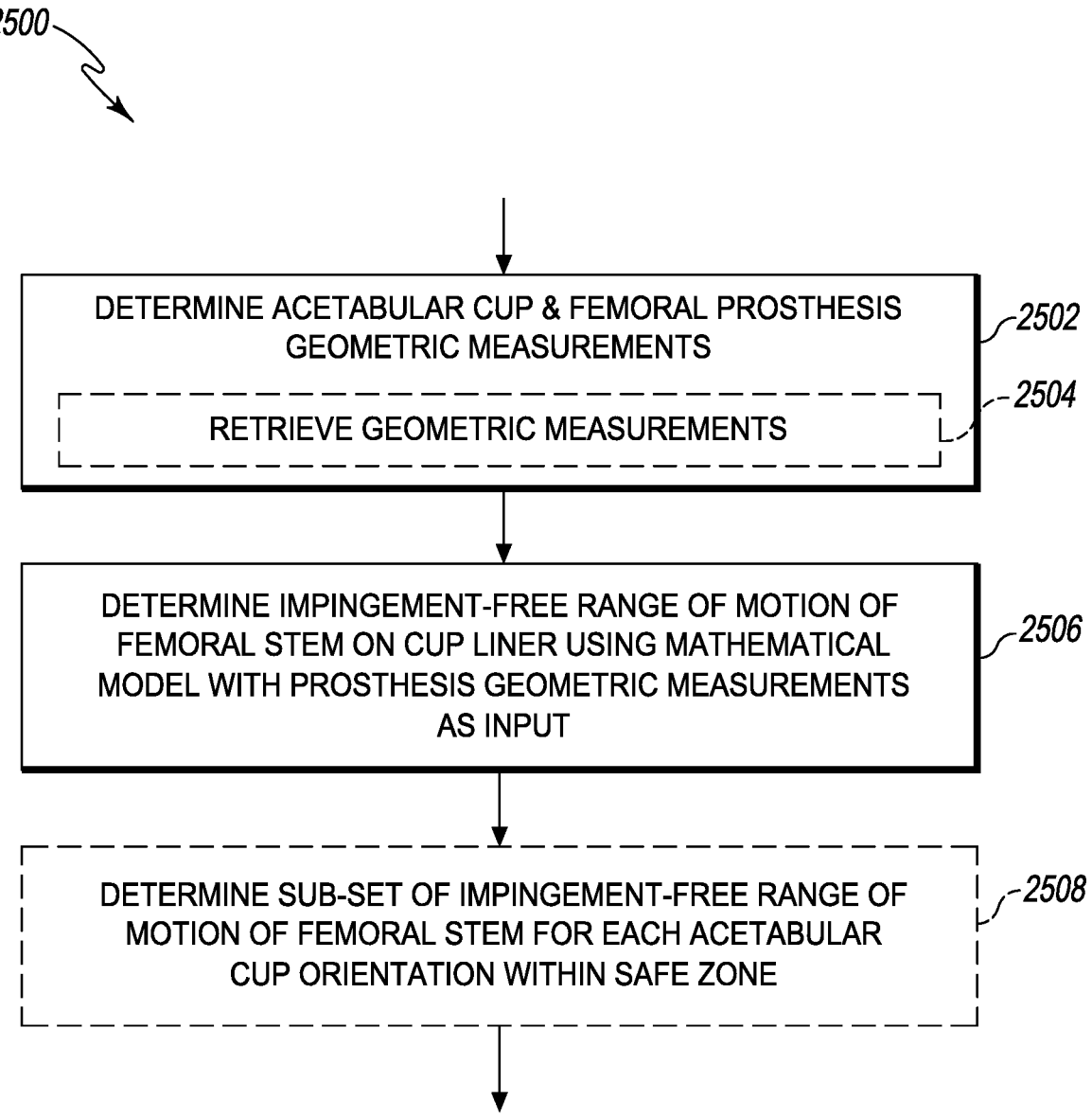
FIG. 25 is a flow chart diagram of an embodiment of a method for determining an impingement-free range of motion of the femoral stem of the femoral prosthesis of the hip prosthesis of FIG. 1 using the mathematical model generated by the method of FIGS. 24A-24B.

After the mathematical model has been generated in block 2442, the mathematical model may be subsequently used in the determination of the impingement-free range of motion in block 2136 of method 2100 of FIG. 21B. To do so, the analysis device 402 may execute a method 2500 for determining an impingement-free range of motion of the femoral stem 110 of the femoral prostheses 102 and the acetabular cup 104 using the generated mathematic model as shown in FIG. 25. The method 2500 begins with block 2502 in which the geometric measurements of the acetabular cup 104 and femoral prosthesis 102 to be used in the orthopaedic surgical procedure are determined. As discussed above, the geometric measurements determined in block 2502 illustratively include an inner diameter measurement of the acetabular cup 104 (i.e., of the cup liner 122), an outer diameter measurement of the acetabular cup 104, a proximal-distal distance measurement from the medial edge of the cup liner 122 of the acetabular cup 104 to the center of rotation of the femoral head 118 of the femoral prosthesis 102, a proximal-distal distance measurement from the lateral edge of the cup liner 122 of the acetabular cup 104 to the center of rotation of the femoral head 118 of the femoral prosthesis 102, and the neck angle of the femoral stem 110 of the femoral prosthesis 102 (e.g., relative to the longitudinal angle of the stem 110). In some embodiments, the analysis device 402 may retrieve those geometric measurements from a database based on the type and size of the hip prostheses determined in block 2124 of method 2100. Alternatively, in other embodiments, the orthopaedic surgeon or user may manually enter the geometric measurements. In still other embodiments, the geometric measurements may be determined based on three-dimensional models of the selected hip prosthesis 100 (i.e., the femoral prothesis 102 and the acetabular cup 104).

After the geometric measurements of the hip prosthesis 100 has been determined in block 2502, the method 2500 advances to block 2506 in which the analysis device 402 determines the impingement-free range of motion values of the femoral stem 110 of the femoral prosthesis 102, relative to the cup liner 122 of the acetabular cup 104, using the mathematical model generated in block 2442 of method 2400 with the geometric measurements as input to that mathematical model. Again, as discussed above, impingement-free range of motion values generated by the mathematical model in block 2506 includes a set of impingement-free range of motion values for the range of orientations of the acetabular cup 104 and for each static, functional position of the patient (e.g., sitting and standing).

In some embodiments, the impingement-free range of motion determined in block 2506 may be limited to those acetabular cup orientations that have been previously determined to not result in edge loading of the acetabular cup 104 in block 2304 of method 2300. That is, in block 2506, the impingement-free range of motion may be determined for only those orientations of the acetabular cup 104 that lie within the safe zone boundary as determined in block 2314 of method 2300. Alternatively, in embodiments in which the impingement-free range of motion is determined for a range of acetabular cup orientations that includes orientations outside of the safe zone boundary, the analysis device 402 may determine a sub-set of calculated impingement-free ranges of motion corresponding to those acetabular cup orientations falling within the safe zone boundary in block 2508.

Figure 29:
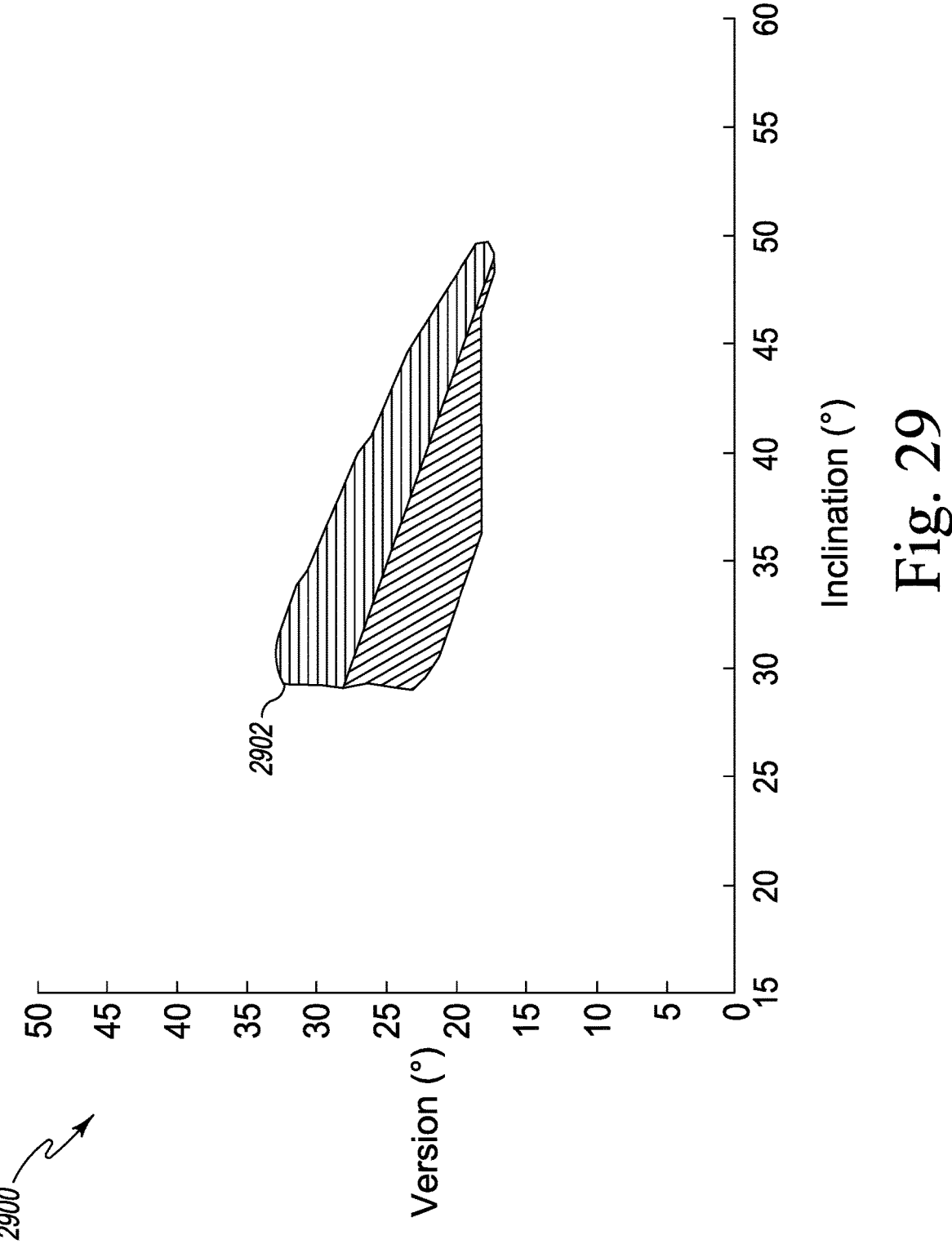
FIG. 29 is an illustrative screen image that may be displayed during the performance of the method of FIGS. 21A-21C showing a graphical representation of the safe zone boundary of acetabular cup orientations as determined by the method of FIG. 23.

Referring now back to block 2132 of FIG. 21B, after the analysis device 402 has determined the impingement-free range of motion values, the method 2100 advances to block 2138 of FIG. 21C in which the analysis device 402 determines whether the orthopedic surgeon or other user desires to view the safe zone boundary of "acceptable" acetabular cup orientations. If so, the method 2100 advances to block 2140 in which the analysis device 402 displays a graph of the safe zone boundary of acetabular cup orientations, which identifies those cup orientations that do not result in edge loading. For example, in the illustrative embodiment, the analysis device 402 displays a graph 2900 of the safe zone boundary 2902 as shown in FIG. 29. As shown by graph 2900, those acetabular cup orientations (i.e., combinations of inclination and version values) that fall within the safe zone boundary 2902 have been determined to not result in edge loading of the acetabular cup 104 by the femoral prosthesis at each of the stationary, functional positions of the patient (e.g., standing and sitting). In some embodiments, those acetabular cup orientations falling within the safe zone boundary 2902 may be further identified as relating to particular functional positions of the patient (e.g., via different coloring or shading).

Referring back to FIG. 21C, after the analysis device 402 has displayed the graph of the safe zone boundary in block 2140, the method 2100 advances to block 2142 in which the analysis device 402 determines whether the orthopedic surgeon or other user desires to view the impingement-free range of motion for each of the "acceptable" acetabular cup orientations. If so, the method 2100 advances to block 2144 in which the analysis device 402 displays indicia of the impingement-free range of motion on the graph of the safe zone boundary. For example, in the illustrative embodiment shown in FIG. 30, the analysis device 402 may display a "heat map" 3000 of the impingement range of motion values within the safe zone boundary 2902. In this way, the safe zone boundary 2902 provides three-dimensional data to the orthopaedic surgeon or user showing sets of acetabular cup orientations that do not result in edge loading and for which the impingement-free range of motion exceeds certain threshold values (e.g., 5°, 10°, 15°, 25°, 35° in FIG. 30). The orthopaedic surgeon may determine a planned or desired orientation of the acetabular cup 104 based on the displayed information. The impingement-free range(s) of motion may be displayed within the safe zone boundary 2902 in any manner suitable for conveying such data. For example, in the illustrative embodiments, different coloring is used for the different ranges.

Figure 30:
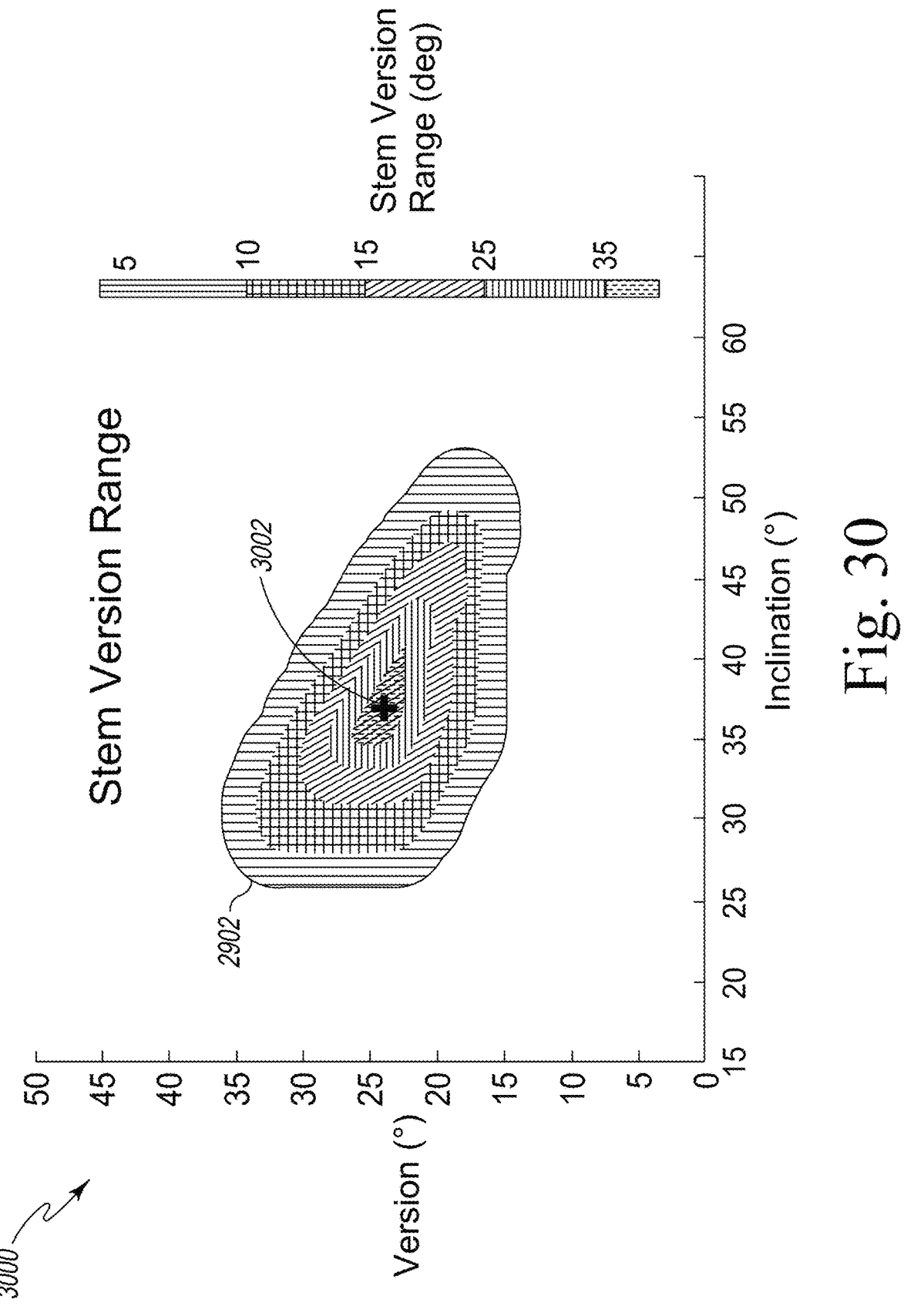
FIG. 30 is an illustrative screen image that may be displayed during the performance of the method of FIGS. 21A-21C showing a graphical representation of the impingement-free range of motion, as determined by the method of FIG. 25, overlaid on the graph of the safe zone boundary shown in FIG. 29.

Referring back to FIG. 21C, after the analysis device 402 has displayed the indicia of the impingement free range(s) of motion in block 2144, the method 2100 advances to block 2146 in which the analysis device determines whether the orthopedic surgeon or other user desires to view the preferred orientation of the acetabular cup 104 as determined in block 2310 of method 2300 in some embodiments. If so, the method 2100 advances to block 2148 in which the analysis device 402 displays indicia of the preferred cup orientation(s) on the graph of safe zone boundary. For example, as shown in FIG. 30, the analysis device 402 may display the heat map 3000 with a mark 3002 or other indication within the safe zone boundary 2902 to provide a visual indication of the determined preferred acetabular cup orientation.

Referring again back to FIG. 21C, if the orthopedic surgeon or user determines not to view the preferred orientation of the acetabular cup 104 in block 2146 or to not view the safe zone boundary in block 2138, the method 2100 advances to block 2150 in which the analysis device 402 determines whether the orthopaedic surgeon would like to analyze the positioning of another hip prosthesis. For example, the orthopaedic surgeon may select a completely different type of hip prosthesis or select a different size of the present type of the hip prosthesis. If so, the method 2100 loops back to block 2124 of FIG. 21B in which the analysis device 402 determines the type and size of the new hip prosthesis as discussed above. However, if not, the method 2100 loops back to block 2138 in which the analysis device 402 again determines whether the orthopaedic surgeon desires to view the safe zone boundary of the presently selected hip prosthesis.

Figure 26B:
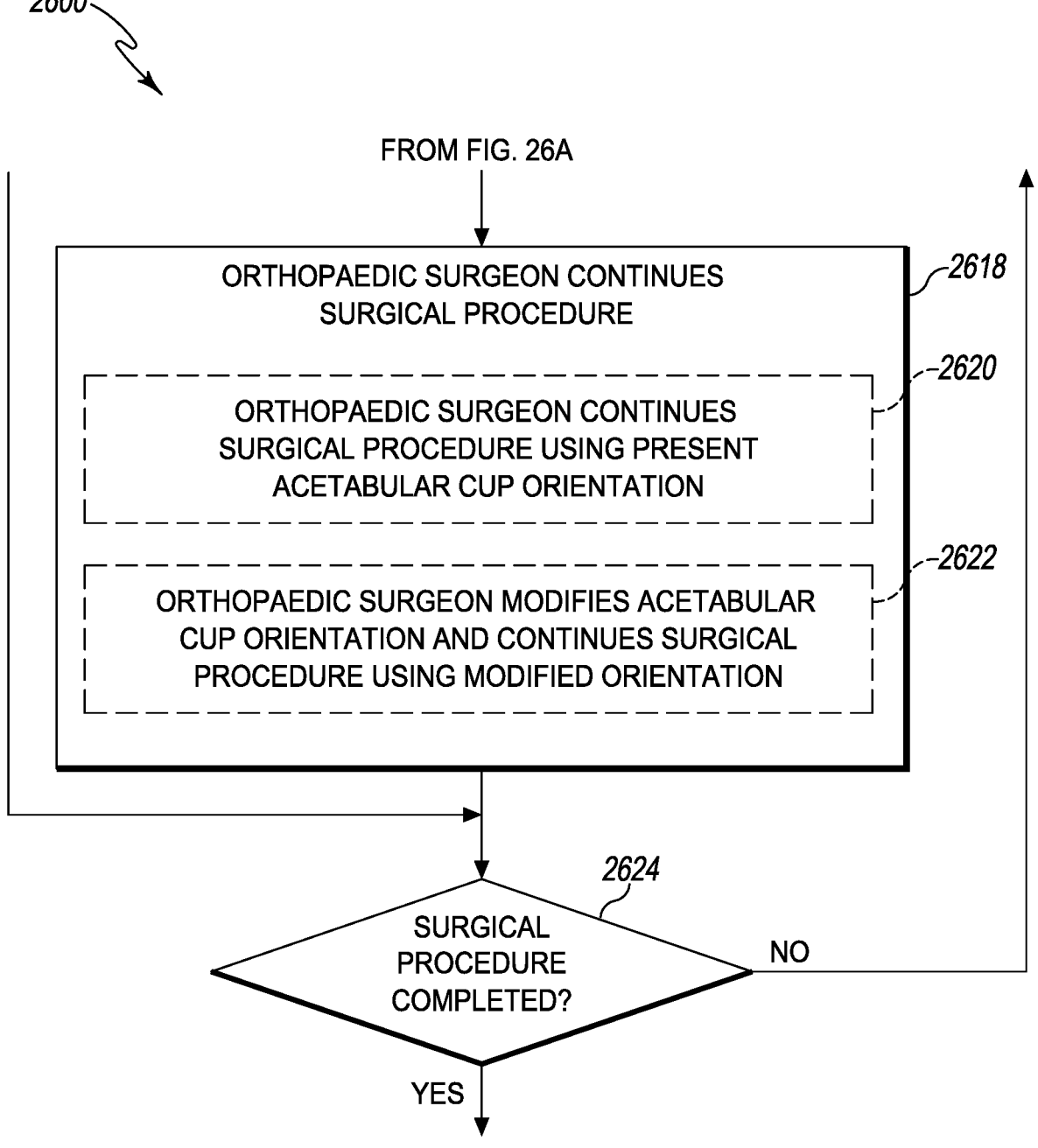

Referring now to FIGS. 26A and 26B, in some embodiments, the analysis device 402 may also execute a method 2600 for intra-operatively monitoring the positioning of the hip prosthesis 100 during the performance of the orthopaedic surgical procedure to implant the hip prosthesis 100 in the patient. For example, the method 2600, or portions thereof, may be embodied as a set of executable instructions stored on the analysis device 402 and executable by the analysis device 402. As such, it should be appreciated that the operations of the method 2600 may be performed by one or more components of the analysis device 402 and/or devices communicatively coupled to the analysis device 402.

The method 2600 begins with block 2602 in which the analysis device 402 pre-operatively determines a planned or desired orientation of the acetabular cup relative to the patient's acetabulum 200. To do so, the analysis device 402 may execute method 2200 described above in regard to FIG. 22 (or the method 600 described above in regard to FIG. 6). As such, it should be appreciated that while the method 2200 may be used pre-operatively to pre-plan the desired orientation of the acetabular cup 104, the method 2600 may be executed during the orthopaedic surgical procedure itself to monitor and/or adjust the actual, present orientation of the acetabular cup 104.

Subsequently, in block 2604, the analysis device 402 determines whether the orthopaedic surgeon desires to monitor the positioning of the hip prosthesis 100 (e.g., the orientation of the acetabular cup 104) while performing the associated orthopaedic surgical procedure. If so, the method 2600 advances to block 2606 in which the analysis device 402 determines the present orientation of the acetabular cup 104 relative to the patient's acetabulum 200. To do so, the analysis device 402 may determine the present orientation of the acetabular cup 104 based on medical images of the patient's acetabulum 200 generated and obtained during the performance of the orthopaedic surgical procedure. For example, the imaging device 404 of the system 400 may be configured to generate medical images of the patient's acetabulum 200 during the orthopaedic surgical procedure and transmit or otherwise provide those medical images to the analysis device 402. Alternatively, in embodiments in which the system 400 includes the surgical tracking system 408, the analysis device 402 may be determine the preset orientation of the acetabular cup 104 based on surgical navigation data provided by the surgical tracking system.

Subsequently, in block 2608, the analysis device 402 displays a graphical user interface to the orthopaedic surgeon. In doing so, the analysis device 402 may display the graph of the safe zone boundary of acetabular cup orientations on the graphical user interface in block 2610. Additionally, in block 2612, the analysis device 402 may display indicia of the impingement-free range of motion on the graph of the safe zone boundary. Furthermore, in some embodiments in block 2614, the analysis device 402 may display indicia of the present acetabular cup orientation, as determined in block 2606, on the graph of the safe zone boundary. Additionally, in block 2616, the analysis device 402 may display indica of the preferred acetabular cup orientation(s) on the graph of the safe zone boundary.

Figure 31:
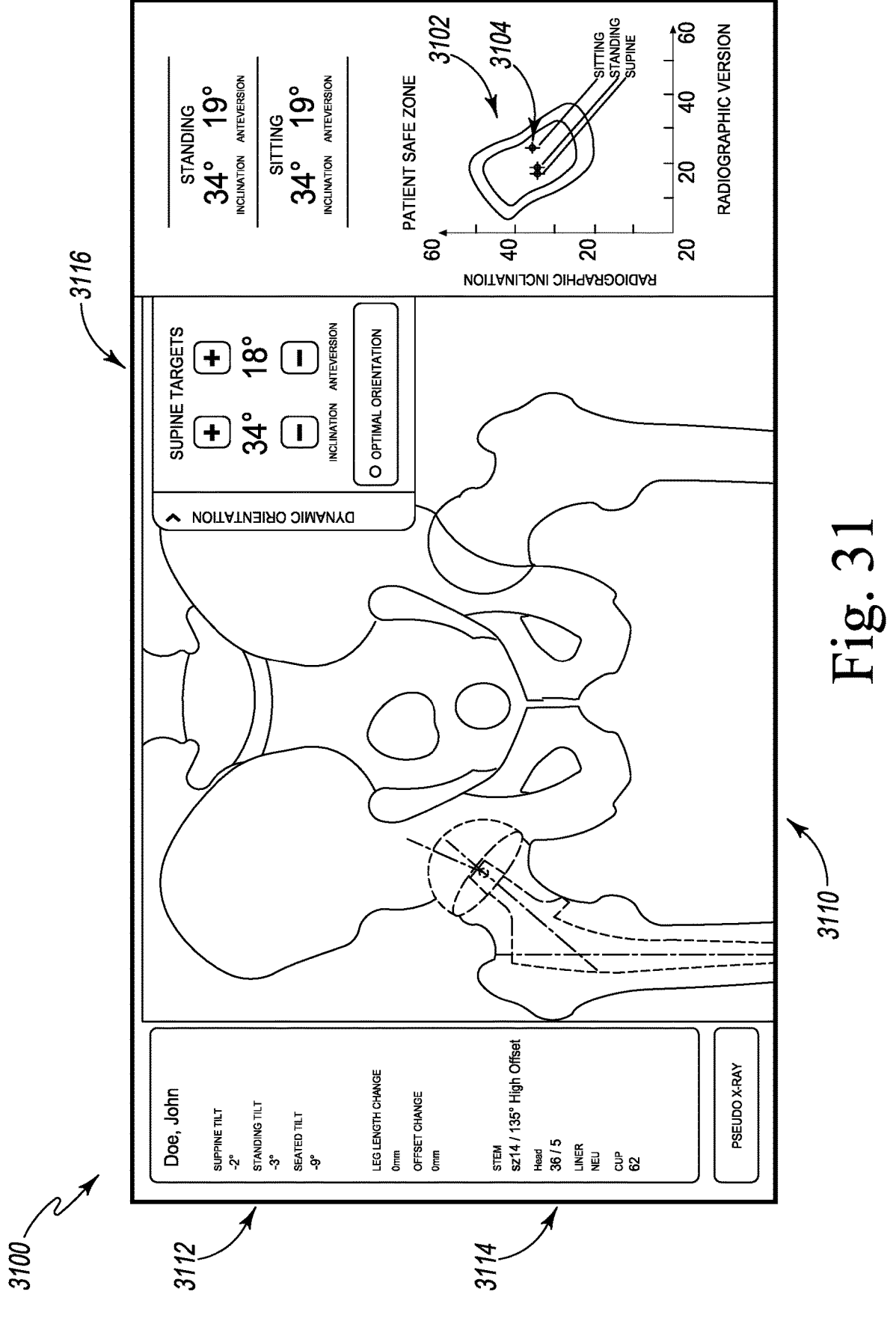
FIG. 31 is an illustrative screen image that may be displayed during the performance of the method of FIG. 26 showing a graphical representation of the hip prosthesis of FIG. 1 on a medical image of a patient, a graphical representation of the safe zone boundary determined by the method of FIG. 23, a graphical representation of the impingement-free range of motion determined by the method of FIG. 25, and indicia of the present orientation of the acetabular cup of the hip prosthesis of FIG. 1 shown on the graphical representation of the safe zone boundary.

For example, an illustrative graphical user interface 3100 is shown in FIG. 31. The graphical user interface 3100 includes a graph 3102 of the safe zone boundary, which may also include indica of the impingement-free range of motion included within the graph 3102 similar to the graph 3000 of FIG. 30. Additionally, the graphical user interface 3100 includes indica 3104 indicative of the present acetabular cup orientation and may, in some embodiments, include further indicia of the preferred acetabular up orientation(s) (although not shown in FIG. 31 for clarity of the figure). The graphical user interface 3100 may include additional information useful to the orthopaedic surgeon in some embodiments, such as, a medical image 3110 of the patient's relevant boney anatomy, the pelvic tilt measurements 3112 of the patient, the geometrical measurements 3114 of the selected orthopaedic prosthesis, and/or a menu 3116 of the preferred or "target" acetabular cup orientations. It should be appreciated, however, that additional or other information may be displayed on the graphical user interface 3100 in other embodiments.

Referring back to FIG. 26, after the analysis device 402 has displayed the graphical user interface including indica of the safe zone boundary and impingement-free range of motion, the method 2600 advances to block 2618 of FIG. 26B. In block 2618, the orthopaedic surgeon continues the orthopaedic surgical procedure based on the displayed safe zone boundary associated with the present orientation of the acetabular cup 104. For example, should the orthopaedic surgeon determine that the acetabular cup orientation relative to the safe zone boundary (and/or impingement-free range of motion) is satisfactory, the orthopaedic surgeon may continue the orthopaedic surgical procedure using the present orientation of the acetabular cup 104 in block 2620. However, should the orthopaedic surgeon determine that the acetabular cup orientation relative to the safe zone boundary (and/or impingement-free range of motion) is not satisfactory, the orthopaedic surgeon may modify or adjust the present orientation of the acetabular cup 104 and continue the orthopaedic surgical procedure using a new orientation of the acetabular cup 104 in block 2622. For example, in some embodiments, the orthopaedic surgeon may adjust the present orientation of the acetabular cup 104 to better match the pre-operatively planned orientation.

In either case, the method 2600 advances to block 2624 in which the analysis device 402 determines if the orthopaedic surgeon has completed the orthopaedic surgical procedure. If not, the method 2600 loops back to block 2604 of FIG. 26A in which the analysis device 402 again determines the present orientation of the acetabular cup 104, which may or may not have been adjusted by the orthopaedic surgeon in block 2622. In this way, the analysis device 402 provides an opportunity to the orthopaedic surgeon to pre-plan an orientation of the acetabular cup 104 based on a predicted performance of the hip prosthesis 100 at that pre-planned orientation and to further monitor and, if desired, adjust the actual orientation of the acetabular cup 104 intra-operatively to better achieve an actual performance of the hip prosthesis 100 for the patient.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. A system for determining a position of a hip prosthesis in a patient, the hip prosthesis having a femoral prosthesis and an acetabular cup, the system comprising:

one or more processors; and one or more memory communicatively coupled to the one or more processors and including instructions that, in response to execution by the one or more processors, cause the system to:

acquire a set of medical images of a hip of the patient;

determine pelvic tilt measurements of a pelvis of the patient based on the set of medical images, wherein the pelvic tilt measurements are indicative of a range of motion of the hip of the patient between different functional positions;

determine a set of contact points between a femoral head of the femoral prosthesis and a cup liner of the acetabular cup with a generic activities-of-daily-living (ADL) mechanics model, using a type and size of the femoral prosthesis and the acetabular cup, the pelvic tilt measurements, and an orientation of the acetabular cup relative to an acetabulum of the patient as inputs to the generic ADL mechanics model, wherein the generic ADL mechanics model is indicative of mechanical motion of a hip exhibited during performance of a set of ADL;

generate a contact plot based on the set of contact points, wherein the contact plot includes an indicia for each contact point in the set of contact points and for an edge of the cup liner;

receive a surgeon's selection of a planned orientation for the acetabular cup relative to the acetabulum of the patient in response to the contact plot; and provide guidance to the surgeon to implant the acetabular cup in the acetabulum of the patient at the planned orientation selected by the surgeon.

2. The system of claim 1, wherein the set of medical images includes an anterior-posterior medical image of the hip of the patient while the patient is standing, a sagittal medical image of the hip of the patient while the patient is standing, a sagittal medical image of the hip of the patient while the patient is seated and fully bent over at the waist, and a sagittal medical image of the hip of the patient while the patient is standing with a contralateral leg in a flexed position and the back extended, and wherein to determine the pelvic tilt measurements of the pelvis of the patient comprises to identify a plurality of anatomical landmarks of the hip of the patient based on the set of medical images.

3. The system of claim 1, wherein the plurality of instructions, in response to execution by the one or more processors, further cause the system to determine a pelvic mobility of the hip of the patient based on the pelvic tilt measurements, wherein to determine the set of contact points comprises to determine the set of contact points with the generic ADL mechanics model using the type and size of the femoral prosthesis and the acetabular cup, the pelvic tilt measurements, the pelvic mobility, and the orientation of the acetabular cup as inputs to the generic ADL mechanics model.

4. The system of claim 1, wherein to determine the set of contact points comprises to:

determine a plurality of sets of contact points between the femoral head of the femoral prosthesis and the cup liner of the acetabular cup with the generic ADL mechanics model using the type and size of the femoral prosthesis and the acetabular cup, a plurality of sets of pelvic tilt values, and a plurality of orientations of the acetabular cup relative to the acetabulum of the patient as inputs to the generic ADL mechanics model, wherein each set of contact points of the plurality of sets of contact points corresponds to (i) a different orientation of the acetabular cup of the plurality of orientations of the acetabular cup and (ii) a different set of pelvic tilt values of the plurality of sets of pelvic tilt values used as inputs to the generic ADL mechanics model; and generate a mathematical model based on the plurality of sets of contact points, wherein the mathematical model is a model of the plurality of sets of contact points and is configured to produce a resultant set of contact points between the femoral head of the femoral prosthesis and the cup liner of the acetabular cup using a set of pelvic tilt measurements as input, wherein to determine the set of contact points comprises to determine the set of contact points using the mathematical model with the pelvic tilt measurements as an input to the mathematical model.

5. The system of claim 1, wherein to determine the set of contact points comprises to determine a subset of contact points of the set of contact points for each ADL activity of the set of ADL, wherein the set of contact points comprises the subset of contact points for each corresponding ADL activity, wherein to determine the subset of contact points for each ADL activity comprises to:

temporally discretize each ADL activity into a plurality of temporal periods;

determine an angle between a femur of the patient and the acetabulum of the patient during each temporal period of the plurality of temporal periods based on the pelvic tilt measurements; and determine a contact point between the femoral head of the femoral prosthesis and the cup liner of the acetabular cup for each temporal period of the plurality of temporal periods with the generic ADL mechanics model using the type and size of the femoral prosthesis and the acetabular cup, the pelvic tilt measurements, the orientation of the acetabular cup, and the determined angle for the corresponding temporal period as inputs to the generic ADL mechanics model.

6. The system of claim 1, wherein the plurality of instructions, in response to execution by the one or more processors, further cause the system to determine an impingement-free range of motion of the femoral prosthesis and the acetabular cup based on (i) a three-dimensional model of the femoral prosthesis and a three-dimensional model of the acetabular cup and (ii) a plurality of orientations of the femoral prosthesis relative to a femur of the patient and a plurality of orientations of the acetabular cup relative to the acetabulum of the patient, and wherein the plurality of instructions, in response to execution by the one or more processors, further cause the system to display the contact plot and indicia of the impingement-free range of motion.

7. The system of claim 1, wherein to determine the set of contact points comprises to determine a plurality of sets of contact points between the femoral head of the femoral prosthesis and the cup liner of the acetabular cup with the generic ADL mechanics model, wherein each set of contact points of the plurality of sets of contact points corresponds to a different orientation of the acetabular cup relative to the acetabulum of the patient used as an input to the generic ADL mechanics model, and wherein the plurality of instructions, in response to execution by the one or more processors, further cause the system to identify a sub-group of the plurality of sets of contact points that are predicted to result in edge loading of the acetabular cup based on a distance between at least one contact point of a corresponding set of contact points of the sub-group and the edge of the cup liner of the acetabular cup being within a reference threshold distance.

8. The system of claim 7, wherein the plurality of instructions, in response to execution by the one or more processors, further cause the system to:

determine an edge loading boundary based on the different orientations of the acetabular cup corresponding to the sub-group of the plurality of sets of contact points that are predicted to result in edge loading of the acetabular cup; and display an indicia of the edge loading boundary.

9. The system of claim 1, wherein to determine the set of contact points comprises to determine a plurality of sets of contact points between the femoral head of the femoral prosthesis and the cup liner of the acetabular cup with the generic ADL mechanics model, wherein each set of contact points of the plurality of sets of contact points corresponds to a different orientation of the acetabular cup relative to the acetabulum of the patient used as an input to the generic ADL mechanics model, wherein the plurality of instructions, in response to execution by the one or more processors, further cause the system to:

determine a distance between at least one outermost contact point of each set of contact points and the edge of the cup liner of the acetabular cup; and identify a preferred orientation of the acetabular cup based on the determined distances.

10. A method for determining a position of a hip prosthesis in a patient, the hip prosthesis having a femoral prosthesis and an acetabular cup, the method comprising:

acquiring a set of medical images of a hip of the patient;

operating a computer system to determine pelvic tilt measurements of a pelvis of the patient based on the set of medical images, wherein the pelvic tilt measurements are indicative of a range of motion of the hip of the patient between different functional positions;

operating the computer system to determine a set of contact points between a femoral head of the femoral prosthesis and a cup liner of the acetabular cup with a generic activities-of-daily-living (ADL) mechanics model, using a type and size of the femoral prosthesis and the acetabular cup, the pelvic tilt measurements, and an orientation of the acetabular cup relative to an acetabulum of the patient as inputs to the generic ADL mechanics model, wherein the generic ADL mechanics model is indicative of mechanical motion of a patient-generic hip exhibited during performance of a set of ADL;

operating the computer system to generate a contact plot based on the set of contact points, wherein the contact plot includes an indicia for each contact point in the set of contact points and for an edge of the cup liner;

selecting a planned orientation for the acetabular cup relative to the acetabulum of the patient in response to the contact plot; and implanting the acetabular cup in the acetabulum of the patient at the planned orientation.

11. The method of claim 10, further comprising operating the computer system to determine a pelvic mobility of the hip of the patient based on the pelvic tilt measurements, wherein operating the computer system to determine the set of contact points comprises operating the computer system to determine the set of contact points with the generic ADL mechanics model using the type and size of the femoral prosthesis and the acetabular cup, the pelvic tilt measurements, the pelvic mobility, and the orientation of the acetabular cup as inputs to the generic ADL mechanics model.

12. The method of claim 10, wherein operating the computer system to determine the set of contact points comprises:

operating the computer system to determine a plurality of sets of contact points between the femoral head of the femoral prosthesis and the cup liner of the acetabular cup with the generic ADL mechanics model using the type and size of the femoral prosthesis and the acetabular cup, a plurality of sets of pelvic tilt values, and a plurality of orientations of the acetabular cup relative to the acetabulum of the patient as inputs to the generic ADL mechanics model, wherein each set of contact points of the plurality of sets of contact points corresponds to (i) a different orientation of the acetabular cup of the plurality of orientations of the acetabular cup and (ii) a different set of pelvic tilt values of the plurality of sets of pelvic tilt values used as inputs to the generic ADL mechanics model; and operating the computer system to generate a mathematical model based on the plurality of sets of contact points, wherein the mathematical model is a model of the plurality of sets of contact points and is configured to produce a resultant set of contact points between the femoral head of the femoral prosthesis and the cup liner of the acetabular cup using a set of pelvic tilt measurements as input, wherein operating the computer system to determine the set of contact points comprises operating the computer system to determine the set of contact points using the mathematical model with the pelvic tilt measurements as an input to the mathematical model.

13. The method of claim 10, wherein operating the computer system to determine the set of contact points comprises operating the computer system to determine a subset of contact points of the set of contact points for each ADL activity of the set of ADL, wherein the set of contact points comprises the subset of contact points for each corresponding ADL activity, and wherein operating the computer system to determine the subset of contact points for each ADL activity comprises:

operating the computer system to temporally discretize each ADL activity into a plurality of temporal periods;

operating the computer system to determine an angle between a femur of the patient and the acetabulum of the patient during each temporal period of the plurality of temporal periods based on the pelvic tilt measurements; and operating the computer system to determine a contact point between the femoral head of the femoral prosthesis and the cup liner of the acetabular cup for each temporal period of the plurality of temporal periods with the generic ADL mechanics model using the type and size of the femoral prosthesis and the acetabular cup, the pelvic tilt measurements, the orientation of the acetabular cup, and the determined angle for the corresponding temporal period as inputs to the generic ADL mechanics model.

14. The method of claim 10, further comprising operating the computer system to determine an impingement-free range of motion of the femoral prosthesis and the acetabular cup based on (i) a three-dimensional model of the femoral prosthesis and a three-dimensional model of the acetabular cup and (ii) a plurality of orientations of the femoral prosthesis relative to a femur of the patient and a plurality of orientations of the acetabular cup relative to the acetabulum of the patient, wherein the computer system causes the contact plot and indicia of the impingement-free range of motion to be displayed.

15. The method of claim 10, wherein operating the computer system to determine the set of contact points comprises operating the computer system to determine a plurality of sets of contact points between the femoral head of the femoral prosthesis and the cup liner of the acetabular cup with the generic ADL mechanics model, wherein each set of contact points of the plurality of sets of contact points corresponds to a different orientation of the acetabular cup relative to the acetabulum of the patient used as an input to the generic ADL mechanics model, and further comprising operating the computer system to identify a sub-group of the plurality of sets of contact points that are predicted to result in edge loading of the acetabular cup based on a distance between at least one contact point of a corresponding set of contact points of the sub-group and the edge of the cup liner of the acetabular cup being within a reference threshold distance.

16. The method of claim 15, further comprising operating the computer system to determine an edge loading boundary based on the different orientations of the acetabular cup corresponding to the sub-group of the plurality of sets of contact points that are predicted to result in edge loading of the acetabular cup, wherein the computer system causes an indicia of the edge loading boundary to be displayed.

17. The method of claim 10, wherein operating the computer system to determine the set of contact points comprises operating the computer system to determine a plurality of sets of contact points between the femoral head of the femoral prosthesis and the cup liner of the acetabular cup with the generic ADL mechanics model, wherein each set of contact points of the plurality of sets of contact points corresponds to a different orientation of the acetabular cup relative to the acetabulum of the patient used as an input to
the generic ADL mechanics model, and further comprising:

operating computer system to determine a distance
between at least one outermost contact point of each set
of contact points and the edge of the cup liner of the
acetabular cup; and operating the computer system to identify a preferred
orientation of the acetabular cup based on the deter-
mined distances.

18. A method of performing an orthopaedic surgical
procedure on a hip of a patient to implant a hip prosthesis
having a femoral prosthesis and an acetabular cup, the
method comprising:

operating a computer system to (i) determine a plurality of
sets of contact points between a femoral head of the
femoral prosthesis and a cup liner of the acetabular cup
with a generic activities-of-daily-living (ADL)
mechanics model, using a type and a size of the femoral
prosthesis, a type and a size of the acetabular cup,
pelvic tilt measurements of the patient, and a plurality
of possible orientations of the acetabular cup relative to
the acetabulum of the patient as inputs to the generic
ADL mechanics model, wherein the generic ADL
mechanics model is indicative of mechanical motion of
a patient-generic hip exhibited during performance of a
set of ADL, and wherein each set of contact points of
the plurality of sets of contact points corresponds to a
different possible orientation of the acetabular cup of
the plurality of possible orientations of the acetabular cup used as an input to the generic ADL mechanics
model and (ii) identify a sub-group of the plurality of
sets of contact points that are predicted to result in edge
loading of the acetabular cup based on a distance
between at least one contact point of a corresponding
set of contact points of the sub-group and an edge of the
cup liner of the acetabular cup being within a reference
threshold distance;

selecting a planned orientation for the acetabular cup
relative to the acetabulum of the patient from among
the plurality of possible orientations of the acetabular
cup not corresponding to one of the sub-group of the
plurality of sets of contact points that are predicted to
result in edge loading of the acetabular cup; and performing the orthopaedic surgical procedure on the hip
of a patient to implant the acetabular cup in the acetabu-
lum of the patient at the planned orientation.

19. The method of claim 18, wherein selecting the
planned orientation for the acetabular cup is performed
pre-operatively to the orthopaedic surgical procedure.

20. The method of claim 18, further comprising operating
the computer system, during the orthopaedic surgical pro-
cedure, to (i) determine an actual orientation of the acetabu-
lar cup positioned in the acetabulum of the patient and (ii)
display a contact plot including indicia for each contact
point in one of the plurality of sets of contact points that
corresponds with the actual orientation of the acetabular cup.

* * * * *